US007572949B2

(12) United States Patent
Blackwell et al.

(10) Patent No.: US 7,572,949 B2
(45) Date of Patent: Aug. 11, 2009

(54) SKN-1 AND GSK-3 GENES AND PROTEINS

(75) Inventors: T. Keith Blackwell, Waban, MA (US); Jae Hyung An, Seoul (KR)

(73) Assignee: Immune Disease Institute, Inc., Boston, MA (US)

( * ) Notice: Subject to any disclaimer, the term of this patent is extended or adjusted under 35 U.S.C. 154(b) by 150 days.

(21) Appl. No.: 10/560,563

(22) PCT Filed: Jun. 14, 2004

(86) PCT No.: PCT/US2004/019046

§ 371 (c)(1), (2), (4) Date: Feb. 15, 2007

(87) PCT Pub. No.: WO2005/049790

PCT Pub. Date: Jun. 2, 2005

(65) Prior Publication Data

US 2008/0141385 A1 Jun. 12, 2008

Related U.S. Application Data

(60) Provisional application No. 60/478,185, filed on Jun. 13, 2003.

(51) Int. Cl.
*A01K 67/00* (2006.01)
*A01K 67/033* (2006.01)
*A61K 49/00* (2006.01)

(52) U.S. Cl. ................................ 800/13; 800/8; 424/9.2

(58) Field of Classification Search ..................... 800/8, 800/13

See application file for complete search history.

(56) References Cited

OTHER PUBLICATIONS

Bhat et al., "Structural insights and biological effects of glycogen synthase kinase 3-specific inhibitor AR-A014418," *J. Biol. Chem.*, 278:45937-45945 (2003).

Blackwell et al., "Formation of a monomeric DNA binding domain by Skn-1 bZIP and homeodomain elements," *Science*, 266:621-628 (1994).

Bowerman et al., "skn-1, a maternally expressed gene required to specify the fate of ventral blastomeres in the early *C. elegans* embryo," *Cell*, 68:1061-1075 (1992).

Bowerman et al., "The maternal gene skn-1 encodes a protein that is distributed unequally in early *C. elegans* embryos," *Cell*, 74:443-452 (1993).

*C. elegans* Sequencing Consortium, "Genome sequence of the nematode *C. elegans*: a platform for investigating biology," *Science*, 282:2012-2018 (1998).

Cohen et al., "The renaissance of GSK3," *Mol. Cell Biol.*, 2:769-776 (2001).

Delaunay et al., "A thiol peroxidase is an H2O2 receptor and redox-transducer in gene activation," *Cell*, 111:471-481 (2002).

Gaudet et al., "Regulation of organogenesis by the *Caenorhabditis elegans* FoxA protein PHA-4," *Science*, 295:821-825 (2002).

Hayes et al., "Molecular basis for the contribution of the antioxidant responsive element to cancer chemoprevention," *Cancer Letters*, 174:103-113 (2001).

Itoh et al., "Keap1 represses nuclear activation of antioxidant responsive elements by Nrf2 through binding to the amino-terminal Neh2 domain," *Genes Dev.*, 13:76-86 (1999).

MacAulay et al., "Use of lithium and SB-415286 to explore the role of glycogen synthase kinase-3 in the regulation of glucose transport and glycogen synthase," *Eur. J. Biochem.*, 270:3829-3838 (2003).

Maduro et al., "Restriction of mesendoderm to a single blastomere by the combined action of SKN-1 and a GSK-3beta homolog is mediated by MED-1 and -2 in *C. elegans*," *Mol. Cell.*, 7:475-485 (2001).

Nguyen et al., "Increased protein stability as a mechanism that enhances Nrf2-mediated transcriptional activation of the antioxidant response element. Degradation of Nrf2 by the 26 S proteasome," *J. Biol. Chem.*, 278:4536-4541 (2003).

Stein et al., "WormBase: network access to the genome and biology of *Caenorhabditis elegans*," *Nucleic Acids Research*, 29:82-86 (2001).

Sekhar et al., "Nrf2 degradation by the ubiquitin proteasome pathway is inhibited by KIAA0132, the human homolog to INrf2," *Oncogene*, 21:6829-6834 (2002).

Stewart et al., "Degradation of transcription factor Nrf2 via the ubiquitin-proteasome pathway and stabilization by cadmium," *J. Biol. Chem.*, 278:2396-2402 (2003).

Thatcher et al., "The *Caenohabditis elegans* peb-1 gene encodes a novel DNA-binding protein involved in morphogenesis of the pharynx, vulva, and hindgut," *Dev. Biol.*, 229:480-493 (2001).

Toone et al., "AP-1 transcription factors in yeast," *Curr. Opin. Genet. Div.*, 9(1):55-61 (1999).

Toone et al., "Redox control of AP-1-like factors in yeast and beyond," *Oncogene*, 20:2336-2346 (2001).

WormBase reference #F37B12.2.

WormBase reference #F39B2.3.

WormBase reference #M176.2.

WormBase reference #T19E7.

Walker et al., "A conserved transcription motif suggesting functional parallels between *Caenorhabditis elegans* SKN-1 and Cap'n'Collar-related basic leucine zipper proteins," *J. Biol. Chem.*, 275:22166-22171 (2000).

Yost et al., "GBP, an inhibitor of GSK-3, is implicated in Xenopus development and oncogenesis," *Cell*, 93:1031-1041 (1998).

*Primary Examiner*—Valarie Bertoglio
(74) *Attorney, Agent, or Firm*—Fish & Richardson P.C.

(57) ABSTRACT

The present invention relates, in part, to the *C. elegans* SKN-1 gene and protein (a transcription factor), and target genes thereof. The invention includes various therapeutic methods and screening methods for identifying antioxidants.

14 Claims, 39 Drawing Sheets

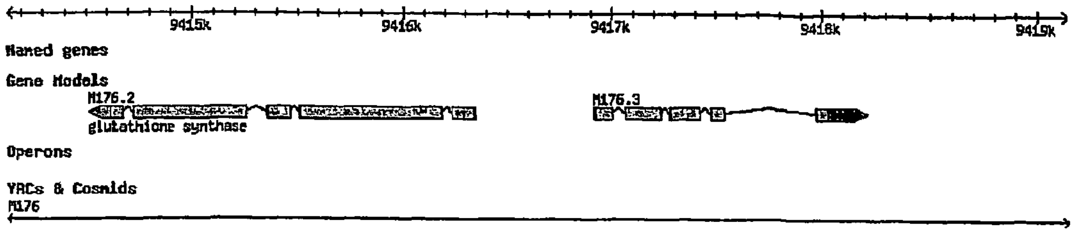

The M176.2 gene is located on chromosome II. Regulatory sequences can be found e.g., in the region between 9416340 and 9415915. An exemplary sequence of this region is as follows:

GACAATTATCGATTAATAAAAGTTTAAACAGACACGAGAAATTAAATATAAAAAATTGAATTGTTTATTT

GTTGTTTTGTGTGTAGAAAAAATAATTTTGATAGAAACAAAAAATTAGCGTAAAATAAATAGCTAGCGCAA

TACTCGTGCACGAGATGTGCGCCAGCAGCTCCTTGACGCAAAACGTGACGTTTAGCACCAAAATGATTTT
-378

TGCTCTTTGAGTTCTTTGTTTTCGGGAGCAAATTTCATGCCAATCCCTTTCTTTTTTTCAAATTTTCCTG

TTAAATTCATGTAATAACTATTATTCATGTCAATTACAACAAATAAGCATCCAAGATTTTATCATAAACT
-243

CGTTCAAACCTCCTTTTACCACTCGAAAAGCAATATCTCCGACTTCCTTCAAAGAGAAATGATGACAAAA
-169

CATAGAAACCTCACGTTATACGTTTTGTCATCACGATTTCAGTGCTCACTTTTCTCATTTCATTCTCGCT
-137

TAATTTCATTTTTGTCACTCTCGCGTCATGTTTTGCATTTTTCGAAAGCATTTATTTAAAACTGAAAAAA

TAATTCGTAATTTTTCAAGAATGGCT

FIG. 7

Exemplary M176.1 sequences:

Amino Acid Sequence

MAQKDDRILL LNAPRLPLED DKLNELTADL HDWAHANGLV MRLSTDKLSS EVCQTTPLTL LPSPFPKNVF EEAVHIQNLF
ASLYHFIAYE FDFLIDIHKN VVKTDDFTRN MVEILKKVKA QGLKQPVTLA IQRSDYMCHK DQYSAEYGLK QIEINNIASS
MGAHALRLTE WHIRVLKALN ISDDVIQRAI PENKPIPMIA EALFKAWSHF SNPAAVVLVV VENVNQNQID QRHVEYELEK
LGVPMTCIIR RNLTQCYEQL SLNDRSDLMI DGRQVAIVYF RAGYSPDHYP STKEWEARER MELSTAIKTP WIGLQVANTK
KTQQVLSEDG VLERFIGKPR EARDIRASFA GMWALENTDE VTMKVVAGAQ KHPEAFVLKP QTEGGAALHT GDEMVQMLRE
LPEEERGAFI LMEKLKPMII ENYLVLAKKP ITFAKAVSEL GVYGYAFGRK DAPELKTAGH LLRTKPESTA MGGVAAGHAV
VDTPFLYEFI

Spliced mRNA aaagaATGGCT CAAAAAGATG ACCGGATTTT GCTGTTGAAT GCTCCAAGGC TCCCGCTCGA AGATGATAAG CTCAACGAGC
TCACCGCTGA TCTTCACGAT TGGGCTCATG CTAATGGGCT TGTCATGCGT CTATCAACCG ACAAGTTGAG CAGCGAAGTT
TGTCAAACTA CTCCATTAAC ACTTCTTCCA TCTCCATTCC CGAAAAATGT TTTTGAAGAA GCAGTTCATA TTCAGAACCT
TTTCGCAAGT CTTTATCACT TCATAGCTTA TGAATTTGAT TTTCTAATCG ATATTCATAA AAATGTCGTG AAAACTGATG
ATTTCACACG GAATATGGTT GAGATCTTGA AGAAAGTCAA AGCCCAAGGA CTCAAGCAAC CAGTCACTCT CGCGATTCAA
CGATCTGATT ATATGTGTCA TAAGGATCAA TATTCAGCGG AATATGGACT GAAACAAATT GAAATAAACA ATATCGCCTC
GTCAATGGGA GCACATGCTC TACGGCTCAC CGAATGGCAT ATCAGAGTTC TTAAAGCGTT GAACATTTCC GATGACGTCA
TTCAAAGAGC AATTCCAGAA AACAAGCCAA TTCCAATGAT CGCTGAAGCT TTATTCAAGG CCTGGTCCCA CTTTTCGAAC
CCAGCAGCTG TGGTTCTTGT CGTTGTAGAA AACGTCAATC AAAATCAGAT TGATCAACGC CACGTGGAAT ATGAACTTGA
AAAGTTAGGA GTACCGATGA CATGTATTAT TAGAAGAAAT TTAACACAAT GCTATGAACA ATTATCATTG AATGATAGAA
GCGATTTGAT GATTGATGGG CGTCAAGTAG CAATTGTTTA CTTCAGAGCA GGATACTCAC CTGATCATTA TCCATCTACA
AAAGAATGGG AAGCACGTGA GCGTATGGAA CTTTCCACCG CTATCAAAAC TCCATGGATC GGGCTACAGG TGGCAAATAC
TAAGAAGACC CAGCAGGTTC TTTCTGAAGA TGGAGTACTC GAAAGATTCA TCGGAAAACC ACGAGAAGCT CGCGATATTC
GAGCTTCATT CGCAGGAATG TGGGCTTTGG AGAACACTGA TGAAGTGACT ATGAAAGTCG TGGCTGGAGC TCAAAAACAT
CCAGAAGCGT TTGTTCTGAA GCCACAAACT GAAGGTGGAG CCGCATTGCA CACCGGTGAT GAGATGGTTC AAATGCTCCG
AGAACTTCCG GAAGAAGAGC GTGGAGCTTT CATTTTGATG GAGAAACTGA AACCGATGAT TATTGAAAAC TACCTGGTTC
TTGCAAAGAA GCCGATCACA TTTGCTAAGG CTGTTAGTGA ACTTGGAGTG TATGGTTATG CATTTGGAAG GAAGGATGCA
CCTGAGCTTA AGACTGCTGG GCATTTGCTC CGAACGAAAC CGGAATCCAC AGCTATGGGT GGAGTAGCCG CCGGACATGC
TGTTGTCGAC ACCCCATTCC TCTACGAATT TATTTGAttt cgaacataat cagaaaactc aacaaaaatg ctgtgatatg
aaaccatttg ctatttagat ctttttgtgt ttgtaaattt aatcattgta atttattgaa tgt

FIG. 8

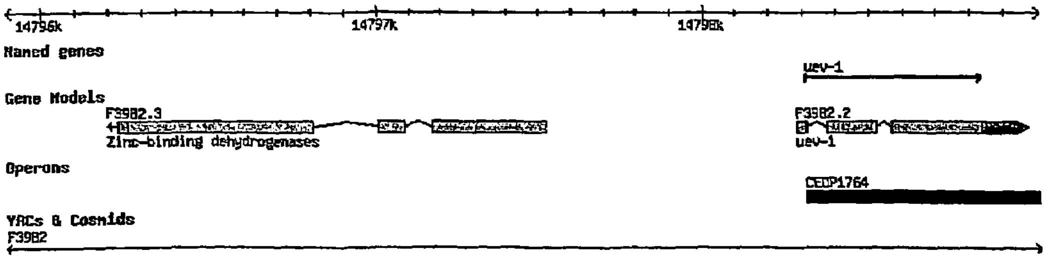

The F39B2.3 gene is located on chromosome I. Regulatory sequences can be found e.g., in the region between 14 797 521 and 14 798 310. An exemplary sequence of this region is as follows:

CATTTTGAAAGTGCCCAAGTTGCTGGAACGCTGAAAATTGAAATTATTAACAAAGAAATTTGCTTTAAAA

TCCGAAAAATCAAGAAAAAATCGATAATTTCGTCGGACAATCCGCCTGCTAGCACGGCTTGACGCTCGTT

TGCCGCGCGCTCATTCGATTTGTGTGAGTGCCCAGTGGAGCGCGTTTGCTAAGGCTAACTGTGTAGTCCT

CTCGGACAAGATCTGTGAACATTGAAATGAAACACTTGGGTTCAATAAAATCACAAGAAAATGATGACAA
-518

TTTTGTTTGCGACCGAAAAAAAATTATAAAAATTGAATATTGGTTATCATCGTTTCAATCTTTGTTTTGT
-469

ATTAAAGGCACAGCTGCTAAAAATTGTTTTTTTTTTTCAATTTTGCTAAAAGAAAATCAATTTTCTGAT

TTTTTGTTGAGTTCCCGTGCAAATCAATGTCCTAGCTTTTTAAAATTGTTTTTTGTTATGTAATTCTAAT

CAAATTTTGTCGAATTTTCAGAGATTTTCTGCTAAAACACTAAAAATAGTCTAAAAGTCGATAATTTGAT

AAACATTTACTCAAACCTTTTACGGAAAAATGAAACAAAAGTTGCAAAAATATAGTAATTTCGCAATTTT

CTGAACGCGTACTTAAAGGTACACGGTTTGATTCGGATTGGTCCCGCCACAAAGTGTTACCATAACATTT

TTCTCGCTGCGAGACCCATCCGAATAAATCCGTGCGCCTAATCAGTGCGAGTACGCATTTCATATTACTG

ATAAGTGCCATTTTTAGAACAATG

FIG. 9

Exemplary F39B2.3 sequences:

Amino Acid Sequence

MSKSICKSSM RAAVVRRFGA PDVIEAVESD MPRLEKNQVL VRNYAAGVNP VDTYIRAGQY GKLPNLPYVP GKDGAGFVEL
VGESVKNVKV GDRVWYGSEA DSTAEYVAVN RPFELPEGVS FEEGASLGVP YLTAYRALFH LAGAKTGDVI LVHGASGGVG
SALMQLAAWR NIEAVGTAGS ADGIRFVKSL GARNVYNHSD KQYVSKMKND YPGGFNHIFE MAAHTNLNTD LGLLAPRGRV
AVIGNRAETT INARQLMVTE GAVYGVALGM SSEAELLDFG INIVSFLKET EFRPLINKLY RLEQLGLAHE EIMNNKGAKG
NLVVQIEH

Spliced mRNA

ATGAGCAAAT CGATTTGCAA ATCAAGCATG CGCGCAGCTG TAGTCCGACG ATTCGGAGCA CCTGATGTCA TAGAAGCCGT
CGAGAGTGAT ATGCCCAGGC TTGAAAAAAA CCAGGTTCTC GTTCGGAATT ACGCTGCCGG TGTCAATCCA GTTGACACAT
ATATTCGTGC TGGTCAGTAT GGAAAACTAC CAAATCTTCC ATATGTACCA GGAAAAGATG GAGCCGGATT CGTCGAACTT
GTGGGAGAAA GCGTTAAAAA TGTGAAAGTC GGCGATCGAG TCTGGTATGG ATCAGAAGCG GACAGTACAG CAGAGTATGT
TGCGGTGAAT CGACCATTCG AGTTGCCGGA AGGAGTTTCG TTTGAGGAAG GAGCTTCTCT CGGAGTGCCT TATCTTACCG
CTTATCGTGC ATTGTTTCAT CTTGCTGGTG CAAAGACTGG CGACGTTATA CTTGTACACG GAGCATCTGG TGGAGTGGGA
AGTGCACTGA TGCAGCTGGC TGCCTGGAGG AACATTGAAG CTGTTGGCAC TGCTGGATCT GCTGATGGGA TCCGGTTCGT
GAAGAGTCTT GGTGCACGGA ATGTCTATAA TCATTCGGAT AAGCAATATG TGTCGAAAAT GAAAAATGAT TATCCAGGAG
GCTTCAACCA CATTTTCGAA ATGGCTGCTC ACACAAATCT GAACACGGAC CTCGGATTGC TGGCTCCACG TGGTAGAGTT
GCAGTAATTG GAAATCGCGC CGAGACCACG ATCAACGCAA GACAACTTAT GGTTACAGAA GGAGCTGTTT ACGGTGTAGC
ATTGGGAATG TCTTCCGAGG CTGAGCTCTT GGACTTTGGC ATCAACATTG TCTCATTCTT GAAGGAAACC GAGTTTCGTC
CACTTATAAA CAAATTGTAT CGTCTCGAGC AATTAGGACT GGCTCATGAG GAAATTATGA ACAACAAGGG AGCGAAAGGA
AATCTTGTAG TGCAAATCGA ACATTAAttc attattttaa cacgccattt aaaggaa

FIG. 10

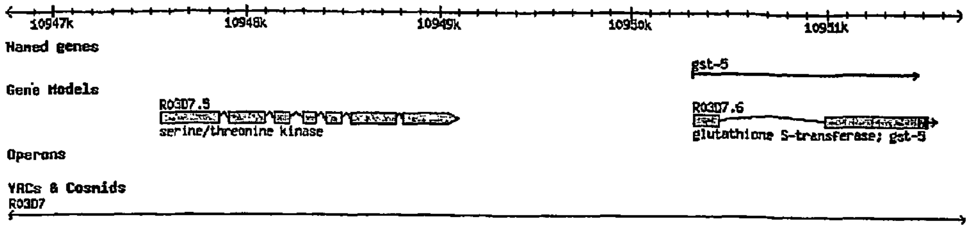

The R03D7.6 gene is located on chromosome II. Regulatory sequences can be found e.g., in the region between 10949088 and 10950317. An exemplary sequence of this region is as follows :

AGAACTTTTCGAGAAGTCTACCGTTGTAGTTTTCGAAATAGTAATTTATTTAGTGACGTTTATAAAGGTTTACATGATTT
GGTTTGGAAATTTTTTAGGAGTTTATTCATAAAAACAAAGTAACCATGGACATTCCAGAAGTCTATAGTACACGCGATCC
TACCGTACCCTTCAGTATTTCTATCAGATTGATAGCTTTCGGTAGTCAGGTACAGCCTAAAAAATTCCTGCTTGCCTTTT
TGCCTACATGTCTGCCTACCTTCAGTCATAATGCCTACATAATG
-947

ATTTTTTCCAATTGAAACTTGCAGACAGAAATTCAAATGGCAAAAAGAAACAAACACCGAAACATTAATCA

CATTTCTTTTCATATCAGTTTTCCTGTCAAAGCACATTTCTGGAGTCTGTGTGTATTTTTTTGTGTCTTTATGTGATCGG
TGTTGTGAAATTTGTAGTTGATGTTGATAACATACTTTTTTTTGAAACAAAAAGTGATTGATTAGGCTTGAATTCAGAGA
TATGTTCGTGATACTTTGCGATTCTCGAGCCAAAAACACGGTATCCGGTCTCGACACGACAACTTTTTCGCAAAATACAA
GCTGATGTGCGCCTTGAAAGAGTACTGTAATTTCAACCTTTCGTTGTTGCGGAATTTTCATAGTTTCTCGTTCAAAATAT
ATGTATTTATTAAACAAAAAACTAAAACAAAACAATTGAGAACACATAAATTGTGAAAAATCAATGAGACCACAGCAAAA
AATTTTGTATCTAGAGTACTCTTTAAAGGCGCACATCCGTTCTTATTTTCAGCAAAAATGTCGCTTCGAGACCGGGTACC
GTATTTTTTTTTGTGCAAAACTTTAGGTCTAGGTAATATTAAAAAAAAATTCCACAAAACTAGAATCTAGAGCTTTCCAT
TAAATTTTTTGATGACATTTGAAAATTCATGATGATTTTTTTCCAACAATTTCGAAATATCCCTCTTTTCACCTGGTCC
-302 -282

ACTGAATTCTCTTTCCGAAAGACCACCACAATTTCAGGGCTCCGCCCATTTCGTGGTTTGTAGCCTTCCCGACCCTACGT
TTTTGATGACAATTGTGAGAGAAGTGAGAGGTTCAGACACAAAAAGCGACGTGGTCGAATGA
-149

GTATAAATAGAGAGTGAAGTTTCCAATTTCCCTCACAATTGTTTGTTTGCAATCCACTTTCCAAAAAAACACAACTTCAA
TCAAAAATCATTATGGTT

FIG. 11

Exemplary R03D7.6 (gst-5) sequences:

Amino Acid Sequence

MVSYKLTYFN GRGAGEVSRQ IFAYAGQQYE DNRVTQEQWP ALKETCAAPF GQLPFLEVDG KKLAQSHAIA RFLAREFKLN
GKTAWEEAQV NSLADQYKDY SSEARPYFYA VMGFGPGDVE TLKKDIFLPA FEKFYGFLVN FLKASGSGFL VGDSLTWIDL
AIAQHSADLI AKGGDFSKFP ELKAHAEKIQ AIPQIKKWIE TRPVTPF

Spliced mRNA

ATGGTTTCCT ACAAGTTGAC CTACTTCAAT GGACGTGGCG CTGGAGAAGT GTCTCGTCAG ATTTTCGCCT ATGCCGGACA
ACAATACGAG GATAATAGAG TCACTCAGGA ACAATGGCCA GCATTGAAAG AAACCTGCGC TGCTCCATTC GGACAACTTC
CATTCCTCGA AGTCGACGGT AAGAAGCTTG CTCAATCCCA CGCGATTGCT CGTTTCTTGG CTCGTGAGTT CAAGCTCAAC
GGAAAAACCG CCTGGGAAGA GGCTCAAGTG AACTCTCTTG CCGATCAATA CAAGGATTAT TCAAGTGAGG CTCGTCCATA
TTTCTACGCT GTCATGGGAT TCGGTCCAGG AGACGTTGAA ACTTTGAAGA AAGACATCTT CCTTCCAGCA TTTGAAAAGT
TCTACGGATT CTTGGTCAAC TTCTTGAAGG CTTCGGGATC CGGATTCCTT GTCGGAGACT CTTTGACCTG GATTGACTTG
GCTATTGCCC AACATTCAGC TGATTTGATT GCCAAGGGAG GTGATTTCAG CAAGTTCCCA GAGCTCAAGG CTCATGCCGA
GAAGATCCAG GCGATTCCAC AAATCAAGAA ATGGATCGAG ACCCGTCCAG TCACACCATT CTAAatagct gtataaaatc
tgcaaataaa tatttttttt tttt

FIG. 12

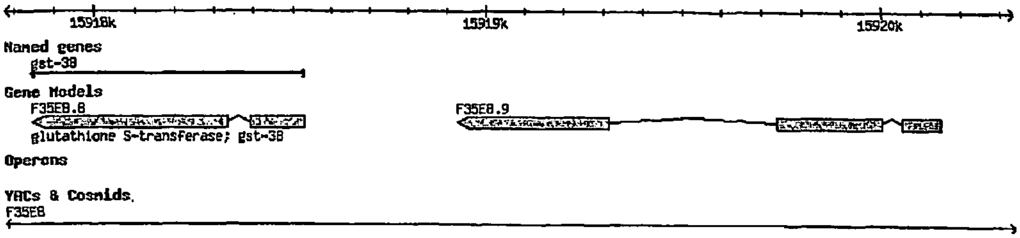

The F35E8.8 gene is located on chromosome V. Regulatory sequences can be found e.g., in the region between 15 917 841 and 15 918 925. An exemplary sequence from in or around this region is as follows:

```
TCTCATTCTCTTCAAGACATAACACAACGGGCTGACGACCATATCATCAACGACGATTTTTTAGGAACTG
TACTTTATCTGTGTCTGACCAACACGTGTGAATGAAGTTTCAACTGGAAAATTTGTTTGAAACACTGCAA
AGAATTTCGAATTTTGATGATAATTTTAAATGCCATTATCAGTTTTAATACGCCACTCTAGTCTTTGATT
                -240

CTTTGCACACACACACACACACACACACACACACACACACTCACAAACACGCCTGAAATTTCGCAATATG
CTGATTTAACGAGAAAACATTTGATGACAATAAACTTGGCGTATTAATATAAAAGGGAAAATTCAATTCA
                       -94

GATTCTCAACGGTTTATTTTCTGTCACAACTCTTCCTAATATTCACCATGGTTT
```

FIG. 13

Exemplary F35E8.8 (gst-38) sequences:

Amino Acid Sequence

MVSYKLTYFD GRGAGELCRQ IFAAAEQKYE DNRLTDEEWE KFKAAGKTPY NQLPMLEVDG KPLAQSHAMA RYLAREFGFN
GKSRWEEAQV NSLADQYKDY YAEARPYLAV KLGYTEGDAE ALYTSVYLPV FKKHYGFFVN ALKASGSGFL VGNSLTFIDL
LVAQHSADLL GREKSDLFND VPEMKAHSEK VQSIPQIKKW IETRPASDW

Spliced mRNA

ATGGTTTCCT ACAAGCTTAC CTACTTCGAT GGACGCGGAG CCGGAGAGCT CTGCCGTCAA ATCTTTGCTG CCGCCGAGCA
GAAATATGAA GATAACAGAC TTACCGATGA GGAGTGGGAG AAGTTCAAAG CGGCCGGAAA AACCCCATAC AACCAGCTTC
CAATGCTCGA GGTAGATGGC AAACCACTCG CTCAGTCCCA CGCGATGGCT CGTTATCTTG CTCGGGAATT CGGGTTCAAC
GGAAAGAGCA GATGGGAAGA AGCTCAAGTC AACTCCTTGG CCGACCAGTA CAAAGACTAT TACGCGGAGG CTCGTCCATA
CCTCGCTGTG AAGCTTGGTT ACACAGAAGG AGACGCGGAG GCTCTTTACA CAAGCGTCTA TCTTCCAGTT TTCAAGAAAC
ACTATGGATT CTTTGTCAAT GCTTTGAAGG CCAGCGGGTC AGGATTCTTG GTTGGAAATT CCTTGACTTT TATTGATTTG
CTTGTTGCTC AGCATTCAGC TGATTTGCTG GGACGTGAAA AGTCGGATCT TTTCAATGAT GTCCCAGAGA TGAAGGCACA
TTCCGAAAAA GTTCAGTCAA TTCCTCAGAT CAAGAAATGG ATTGAGACTC GTCCAGCGAG TGACTGGTAA

FIG. 14

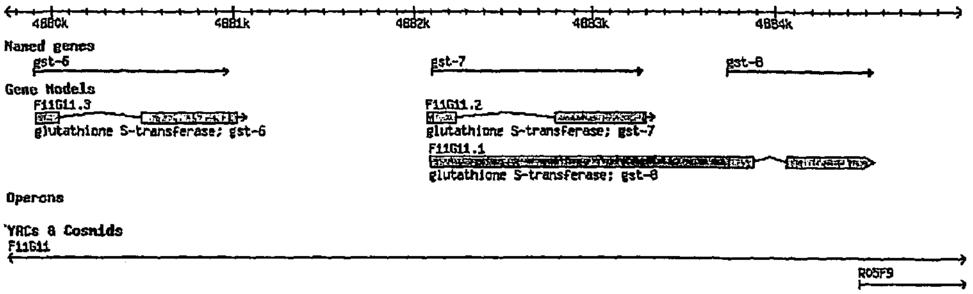

The F11G11.2 gene is located on chromosome I. Regulatory sequences can be found e.g., in the region between 4 880 968 and 4 882 068. An exemplary sequence in or around this region is as follows:

AATTGAAATGAGTTTGCAATTTTGTATTATTTTTTAATTCATATTTCAAGAAGCAATTTTTTGCTAATTTGTTTTAATGG
AAATCGATGTTTCTAAAATATCTTGAATGAATTGTTCTTTTAAAAATTTTATGGTAAAGTTTTCAGCAGGATGTTTCTAT
AGAAGCTTTTTGCATTGCAAGAGTGTTGAAATATACAGGATATTTACAAAAGCCTGGGAAGTAGGCATGCTTTTAGGTAC
AAATCAGACCTACACCGCCTTCCTTTGTGGTTTACCATCATAGCTAAAACTTTCCGAACATTCCCTGGTGAGACACAATG
TTCAAAGCACAAAACCAATCACGTCATAATGTTAATTTGACTTTTATTGTCAAAAATTACAAAAGCGTCGTTTTCTGGAA
CATGAACATAATAAGAATTTTCAAATTTCGGTGGGCACAATAAATATGTAATCTTTTATTTATTTTTGGAGGATAGTCTT
TTCAAAGGCAGGTGTATAACCCTCAAAAGAAAGCACGTTTGTGTTTCAAAGTGAGACTTAAATTATTTCAAAGACAAATT
CCATAGGAAATCATTGTTCATCAGGCACCTTCCCAGAAATTAGGCTGTAGGCAGGCACGTAGGCTGCGGTAAATGCCTAC
GCCTCTTTTGCGCGAGATTATGAAATTGTGTTGTACTGTCGGAAAAATTTCAGAAACAAAAAAAAATATTTTTTGTGACT
TTTTGTGTCAGTTATAGTAGTTTCTTATCATGGTATCTTCAATAATAATGGCAAGCGTAAC
-391

AAGATGATTGATGCCATGGGTTTATATTTGTGAGTAGTCACAAATTGTGACACAACATTCCCTTCGAAAGATCTGGAAAA
GTCACAAAACCTTGCATATATTTTTTTCAACCAATATTATTTTGACCTACTCTGTTCATCGTAACATTGCAACAACAAAA
AACGATGACTACACTTTATGATTTCTAGTCAACAACGTGCGCGCAATGTGTAGAGCAAATGATGACAAACTACAGAATAT
GGTGAGTGGAGAGACGACAGACATTTGAGAAATGGGTATAAATA
-133

GAGACGGCCGGCATTCAGTGTTCAACCCTTCTCATCGACCACTCGATTTCTTGCTTGGTTATTTCAACAATG

FIG. 15

Exemplary F11G11.2 (gst-7) sequences:

Amino Acid Sequence

MVHYKVSYFP IRGAGEIARQ ILAYAGQDFE DNRIPKEEWP AVKPSTPFGQ LPLLEVDGKV LAQSHAIARY LARQFGINGK
CAWEEAQVNS VADQFKDYLN EVRPYFMVKM GFAEGDLDAL AKDVFLPGFK KHYGFFANFL KSAGSGYLVG DSLTFVDLLV
AQHTADLLAA NAALLDEFPQ FKAHQEKVHS NANIKKWLET RPVTPF

Spliced mRNA cgaccactcg atttcttgct tggttatttc aacaATGGTC CACTACAAGG TATCGTACTT CCCAATTCGT GGAGCTGGAG
AGATTGCTCG TCAGATCTTG GCCTACGCTG GACAAGACTT CGAGGACAAC AGAATCCCAA AGGAGGAATG GCCAGCTGTC
AAGCCAAGCA CTCCATTCGG ACAGCTTCCA CTCCTTGAAG TTGACGGAAA GGTTCTTGCC CAATCTCATG CTATCGCCCG
TTACTTGGCT CGTCAGTTCG GAATCAATGG AAAGTGTGCA TGGGAGGAGG CTCAAGTCAA CTCGGTTGCT GATCAATTCA
AGGATTACCT CAACGAAGTT CGTCCATACT TCATGGTGAA GATGGGATTT GCTGAAGGAG ATCTCGATGC TCTTGCCAAG
GACGTCTTCC TTCCAGGATT CAAGAAGCAC TATGGATTCT TTGCTAACTT CCTCAAGTCG GCTGGATCCG GATACTTGGT
TGGAGACTCT TTGACCTTTG TCGACTTGCT CGTCGCTCAG CACACTGCTG ATCTTCTGGC TGCCAACGCA GCTCTTCTCG
ATGAATTCCC ACAATTCAAG GCTCATCAGG AAAAGGTTCA CTCGAATGCC AACATCAAGA AGTGGTTGGA GACTCGTCCA
GTTACTCCAT TCTAAatgat ttcca

FIG. 16

The K08F4.7 gene is located on chromosome IV. Regulatory sequences can be found e.g., in the region between about 10141800 and 10142217. An exemplary sequence of this region is as follows:

ATTATCCAAAAAGATTAGAAGTTGGCAAACCTTGGGCAAGAATTTCCAGAGATTGCACTAAAGTTGTAGCCAAGTTTGAT
CCAACTTTATCCAATCTTTTACTAAAATTATCCTTAAGACTATTTAAATTTTAGATAGAGAATTGGCGAGAGTTAGATCC
CACTTGGATATGACTTATAGTTAGCCTAACCTGAAGCTATTGCTTGCTTGATCATTTGGTTTATCGCTTTGCTACTTGGA
TAACCAGCTCCAATAGTTGTTATTTTTGCTTTTGTCATCATTTT

-157

TCCACGATTTACACTCTCAAGTGAAACCAACTGTTCTTTGATGCCAGACGATGACATTACACTTGATAAGA

-83

AAATATATATAAACTGGAATTAAAAACAATTGATACATCGATTCAATTACTGAATTCTAATTATG

FIG. 17

Exemplary K08F4.7 (gst-4) sequences:

Amino Acid Sequence

MPNYKLLYFD ARALAEPIRI MFAMLNVPYE DYRVSVEEWS KLKPTTPFGQ LPILQVDGEQ FGQSMSITRY LARKFGLAGK
TAEEEAYADS IVDQYRDFIF FFRQFTSSVF YGSDADHINK VRFEVVEPAR DDFLAIINKF LAKSKSGFLV GDSLTWADIV
IADNLTSLLK NGFLDFNKEK KLEEFYNKIH SIPEIKNYVA TRKDSIV

Spliced mRNA

ATGCCAAACT ATAAGCTATT GTATTTTGAT GCTCGTGCTC TTGCTGAGCC AATCCGTATC ATGTTTGCAA TGCTCAATGT
GCCTTACGAG GATTATAGAG TTTCAGTGGA AGAATGGTCA AAGCTGAAGC CAACGACTCC ATTTGGCCAG CTTCCCATTT
TACAAGTCGA TGGAGAACAA TTCGGTCAGT CAATGTCTAT CACAAGATAC TTGGCAAGAA AATTTGGACT CGCTGGAAAA
ACTGCAGAGG AAGAAGCTTA CGCTGATTCA ATTGTAGATC AATACAGAGA TTTCATATTC TTTTTCCGTC AATTCACTTC
TTCCGTTTTC TATGGAAGTG ACGCTGATCA TATTAACAAA GTACGTTTTG AAGTTGTTGA ACCAGCCCGT GATGATTTCT
TGGCAATAAT CAATAAGTTC CTGGCCAAGA GTAAATCAGG ATTCCTCGTT GGAGACTCAT TGACTTGGGC TGATATTGTG
ATTGCTGACA ATTTGACAAG TCTCCTGAAG AATGGATTCT TAGATTTCAA CAAAGAAAAG AAGTTGGAAG AGTTCTATAA
CAAGATTCAT TCAATTCCAG AAATTAAGAA TTACGTGGCA ACAAGAAAGG ATAGTATTGT TTAAaatcga attatttaag
tctgaattat gtatgtagta aaataatatc gttcctatca cgtctcccag agagcgtaat aaattattat tatgtg

FIG. 18

The *sod-1* gene is located on chromosome II. Regulatory sequences can be found e.g., in the region between about 6 973 806 and about 6 974 406. An exemplary sequence of this region is as follows:

```
ATTCCGCAACCCCGTCAAATTTAAGAAGAGAAAGAAAAAAAACACAACGTGTTTGCACCTGTAAGGTAGT
TTTTTTTTGTTGCCTTCGGCGTTTTGATTCACATGAAAGTTCTACGGAAAAAACTTTCATTGCATAACGA
TCTTCATATCTTGTTTCTGGAAACGAAAATTTCCAACATGAAAGAAACCCGACGCTATTTATTCTCGCAA
CACAAAAATTTCACATTTAAATAACCGCGGTTTTTCTCGAACAGCATATTTGACGCGCATTGCTCGTCAA
GTTTGATGCGTGCACACTATTTTGCTGTTGTTTTTTTCTTTTTTCTCTAAATTTTCTTTACGCTTTCGTA
GTTTCTATAGAAACGATTCTCCACTCCCGGTTTTCTTCCGATTCTCAAAATTAATTAAAATTTAGTTATT
AAAAATCCTTTTTCTTGAAATAATCGTTCAATTTCGAGTTTTCAAGAGTGGAGACGTTGAATTTGTGAGC
CGCTTATTTTTTCTGTGTTTTTGTTTTGTGGTTTTTAATCAGTGTCATAATCATACTTTCCATTGTTTCT
                                                -64

TTATTATTCAAAGTTGTAGATTCAGTATTTTAGATCGGTGATG
```

FIG. 19

Exemplary sod-1 sequences:

| Amino Acid Sequence |
|---|

MFMNLLTQVS NAIFPQVEAA QKMSNRAVAV LRGETVTGTI WITQKSENDQ AVIEGEIKGL TPGLHGFHVH QYGDSTNGCI
SAGPHFNPFG KTHGGPKSEI RHVGDLGNVE AGADGVAKIK LTDTLVTLYG PNTVVGRSMV VHAGQDDLGE GVGDKAEESK
KTGNAGARAA CGVIALAAPQ

| Spliced mRNA |
|---|

tttagatcgg tgATGTTTAT GAATCTTCTC ACTCAGGTCT CCAACGCGAT TTTTCCGCAG GTCGAAGCCG CTCAAAAAAT
GTCGAACCGT GCTGTCGCTG TTCTTCGTGG AGAAACTGTT ACCGGTACTA TCTGGATCAC ACAGAAGTCC GAAAATGACC
AGGCAGTTAT TGAAGGAGAA ATCAAGGGAC TTACTCCCGG TCTTCATGGA TTCCACGTTC ACCAATATGG TGATTCCACC
AACGGATGCA TTTCTGCCGG TCCACACTTC AATCCATTTG GAAAGACTCA TGGTGGACCA AAATCCGAGA TCCGTCACGT
AGGCGATCTA GGAAATGTGG AAGCTGGAGC CGATGGAGTG GCAAAAATCA AGCTCACCGA CACGCTCGTC ACGCTTTACG
GTCCAAACAC TGTCGTTGGC CGATCTATGG TTGTTCATGC CGGACAAGAC GACCTCGGCG AGGGAGTCGG AGACAAGGCA
GAAGAGTCCA AGAAGACTGG AAACGCCGGA GCTCGTGCTG CCTGCGGTGT CATTGCTCTC GCTGCTCCCC AGTGActacc
tgaatcgcgt ctctgaatct ccacacaatt cctactaaag acaattttc atttcttgct ttgtcgttat attcttaaga
atcccgttgt tcctactcct actactgtat attttcacat aaaatttctt caaaatttca aataaaggtt gtagtttc

FIG. 20

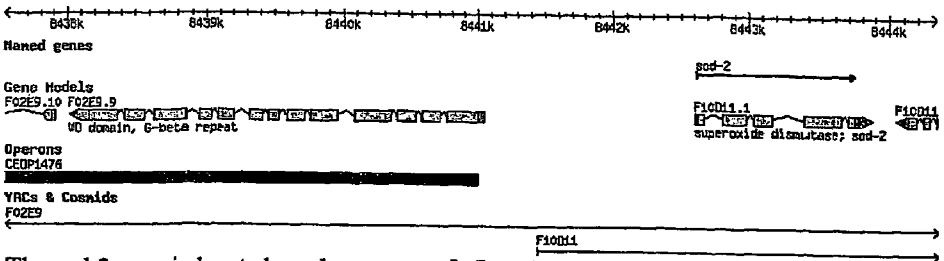

The *sod-2* gene is located on chromosome I. Regulatory sequences can be found e.g., in the region between about 8 441 038 and 8 442 612. An exemplary sequence of this region is as follows:

TGAATAAAAACGTTGAACCCAACGGACATCAAAGTATCAAAGTAAGTAAGTAAGTAAGTAACCTGAATAAAAACGTTGCA
TATAAAAAATCTACTCGAAAATTAAGTGAGAATTGAAGGATTGCTTTCCGAAGAGAAAATGACAATTATAGGGTATACTA
AAACATCAAAAATGTATATTAGACTACCATAAATATAAAACATCAGTGCTGCTCTCCAAGCTATTCTGACGGATTGCGAC
AACGAGCTCGCTGGAGTTGGCATCAGTGTGGAAGGCAGACACATAAGAAGACTCGAATTTGCGGATGACGTAGTCCTGAC
ATGTTCCACACCGGGAGAAGTTCAAGAACGACTGGAAATTTTGGACCGAATAAGTTCTAATTACGGACTCAAGATCAATC
AGTCAAAGACTGTTCTTCTGAAGAACAAGTTTTGCCGGAGCCAAGACGTCCTTTTCAACGGATCCCCCATCATTCCCGTG
CCTGGTTGCCGCTATCTGGGTCGCTGGATCGACATTTCTGGCTCAATTGACGAAGAGATCTCGAGGAGAATAAGAGCAGG
TTGGGGTGCTCTGGTTGGAATCAAAGAAGTCTTGAGAATCATGCCAAACAAGGAAAGAATCATCCTCTTCAAGCAAAAT
-980 -959

GTGCTACCAGCTCTCCTGTATGCTAGTGAAACTTGGACTTGTAATGCTGGATCCACGTTGAGACTCAAAAGAACTGTCAC
CGGTCTCATCGACGCTGCAGAAATTCGAGGCTGGAACTTCAACTTGGAACGTTACCTCCTTGCAAAACAATCAAGATTTG
CAGGACACATTCTACGGAGAGATCCAAACCGATGGACAAAAATCTGCACGGAATGGGACCCGAGCCACAACAAAAATTGG
AAACGTGCCGTTGGAGGACAGAAGAAGAGATGGGCTAAGGACATCGACGAAGAATACGCAAAATTCCACCACAATTCCGC
CATGTCGGGACAAGTCGTTGTTGGGAGAAGAAGACTAGGAATGCTCACTCCGAAGGCTCCATGGCTGTCCATCGCACGAA
CCGACCGTGAAAAATGGAAAGAGTTTGTCCGCAGTTGCCTCGCAACTTGAACCCAACGGACATCAAAGTATCAAAGTAAG
TAAGTAAGTAAGTAACCTGAATAAAAACGTTGCAATTAAAAAATCTACTCGAAAATTAAGTGAGAATTGAAGGATTGCTT
TCCGAAGAGAAAATGACAATTATAGGGTATACTAAAACATCAAAAATGTATATTAGACTACCATAAATATTACGATAAT
-363

TTAAAAATTACTAGAAACACGCAATTCGGCTCAAAAAGCAACAATTTAGACTGAAAACGAGCTAAAAGAATATTATTCAA
AAACCACTTTGCTCGGTAAATCTGGTGTATCATGTTCCGCAAACACTGTCTTTTGTTTTGCG
-191

TACTTTGTTTACGCGCATTCGAATTTCAGTGTTCGCGCTTTTTGTTTACTTTTTTATTTTTCATCCAAAAATCGTATTTT
CAGCTTGATATGTTTCTGCGAATTGTAAAAATTTATATTTGACTATTGAATATTTTAATTATTTGCAGCCGAAAATG

FIG. 21

Exemplary sod-2 sequences:

Amino Acid Sequence

MLQNTVRCVS KLVQPITGVA AVRSKHSLPD LPYDYADLEP VISHEIMQLH HQKHHATYVN NLNQIEEKLH EAVSKGNVKE
AIALQPALKF NGGGHINHSI FWTNLAKDGG EPSAELLTAI KSDFGSLDNL QKQLSASTVA VQGSGWGWLG YCPKGKILKV
ATCANQDPLE ATTGLVPLFG IDVWEHAYYL QYKNVRPDYV NAIWKIANWK NVSERFAKAQ Q

Spliced mRNA tttgcagccg aaaATGCTTC AAAACACCGT TCGCTGTGTC TCAAAGCTTG TTCAACCGAT CACAGGAGTC GCTGCTGTTC
GCTCGAAGCA CTCGCTGCCA GATTTACCAT ACGACTATGC TGATTTGGAG CCTGTAATCA GTCACGAGAT TATGCAACTT
CATCATCAAA AGCATCATGC CACTTATGTG AACAATCTCA ACCAAATTGA GGAAAAGCTT CACGAGGCGG TCTCCAAAGG
AAACGTCAAA GAAGCTATCG CTCTTCAGCC AGCTCTCAAG TTCAATGGAG GAGGACATAT CAACCACTCC ATCTTCTGGA
CTAATTTGGC AAAGGACGGA GGAGAACCAT CGGCGGAGTT GCTCACCGCA ATTAAGAGCG ACTTCGGATC TCTGGATAAT
CTTCAAAAAC AGCTTTCGGC ATCAACTGTC GCTGTTCAAG GATCAGGATG GGGATGGTTG GGATACTGTC CAAAGGGAAA
GATCTTGAAG GTTGCCACAT GTGCCAATCA GGATCCACTT GAGGCAACAA CTGGACTTGT TCCACTGTTC GGAATTGACG
TCTGGGAGCA CGCTTACTAC TTGCAGTACA AGAATGTTCG ACCAGATTAT GTCAATGCTA TTTGGAAGAT CGCCAACTGG
AAGAACGTCA GCGAGCGTTT TGCAAAGGCA CAGCAATAAa tgagctgaat cacaagaatt aatcgtcaaa tgtagcagta
gaagttgact cccattgttt tgtaactatt tttgtttctt aattatttcg aaatgtaaat tttcaaacct tttcaaatga
aaagttttca ccg

FIG. 22

The *ctl-1* gene is located on chromosome II. Regulatory sequences can be found e.g., in the region near 14 306 135. An exemplary sequence of this region is as follows:

AAAAAAAAATCGATAAAAAAATCCGCGTCAACGAAAGTTTAAAGTTACAGTATTTGTCGTTTCGAGACCGG
GTACCGTAGTTTTTGGTGAAAACATTGCAAAATTTGGTCAACAATTTCATCGCTGCGAGACCGACACAAC
ACTTTATTTTATTTTTGGGTTTCCCTTATCGCTTATCATAAACATGTGACGTCATCATCTCTTGTACAGA
-997 -978

GCACCGCGACTGGGAGTATAAGAATCGCCGGAAAACATCAATAATCAGTTCGGTAGAAGTGAAAATTGAG
CGTAAAATATGATCATTTTTCGATGCACCATATTTGACGCGCAATACTTCTACAAGCCGCTGTGTACTGC
-880

TCGTGGACAACTTTGGATTATTTTTTGTTTTTAAAATTCAAAATAGTCAATATATTGCTTATTTATAGCG
CGCCTTTTTGACAGTAAGTTTGTCAAATTTGCGCGTAAGTTATGGTGTTTGCACATATGCACCATACAGC
AACACCCCGCGGCCCGGCTAGTGGTACATCCATGCAAATGCGCTCTACTGATAATTTGAGTTTAACCAGG
TTTAGGCGCAAGATAAGAAAAAAGCTTTGGACCAAAAAATTTAGAGTTTATTTTTTTCGGACATTTTTTA
TATACATCACAAAAATATTGGGCCACTCGTTTTTGATAAAAACGACAAGCCCAAAAGTTCAGGTATACGG
TAGACAAATTGCGTACAGGTACCACTTTTCCACGTAGTGCCAGGTTGTCCCATTACGCTTTGATCTATGA
AAAATGCGGGAATTTTTCGTCCAGAAAAATGTGACGTCAGCACGTTCTCAACCATGCGAAATCAGTTGAA
AACTCTGCGTCTATTCTCCCGCATTTTTTGTAGATCTGTAGATTTGTAGATCAATCCATTCCCCGTATAC
CCTGACCCATAATCAATACCTACCTAATTTTTGTCTTTCCCCCTACTTTTTTGCCTGTCCAAAATAAGCG
AGACTATGCCGTAGTCTGGTGTCCAACAACATGTTCCTTATCAGTGATAACGCTACAATCTTCTTTCTTT
TTTCTCTGTTTCTCTTGTCTCTCCCAACCCATATTCCGTATTACACCTCGTCGTGGTCATTTTTTTGTTC
AGAGTTTTATTTAATTCTAAATTTCCTAACTAAAATTTCAGA

FIG. 23

Exemplary ctl-1 sequences:

Amino Acid Sequence

```
MPNDPSDNQL KTYKETYPKP QVITTSNGAP IYSKTAVLTA GRRGPMLMQD VVYMDEMAHF DRERIPERVV HAKGAGAHGY
FEVTHDITKY CKADMFNKVG KQTPLLVRFS TVAGESGSAD TVRDPRGFSL KFYTEEGNWD LVGNNTPIFF IRDAIHFPNF
IHALKRNPQT HMRDPNALFD FWMNRPESIH QVMFLYSDRG IPDGFRFMNG YGAHTFKMVN KEGNPIYCKF HFKPAQGSKN
LDPTDAGKLA SSDPDYAIRD LFNAIESRNF PEWKMFIQVM TFEQAEKWEF NPFDVTKVWP HGDYPLIEVG KMVLNRNVKN
YFAEVEQAAF CPAHIVPGIE FSPDKMLQGR IFSYTDTHYH RLGPNYIQLP VNCPYRSRAH TTQRDGAMAY ESQGDAPNYF
PNSFRGYRTR DDVKESTFQT TGDVDRYETG DDHNYEQPRQ FWEKVLKEEE RDRLVGNLAS DLGGCLEEIQ NGMVKEFTKV
HPDFGNALRH QLCQKKH
```

Coding

```
                                                  aaaATGCCAA ACGATCCATC GGATAATCAA
CTGAAAACCT ACAAGGAGAC GTATCCAAAA CCCCAAGTGA TCACAACTTC AAATGGAGCT CCGATCTACT CGAAGACCGC
CGTGCTCACC GCCGGGCGGC GTGGCCCAAT GCTCATGCAA GATGTAGTTT ATATGGATGA GATGGCTCAT TTCGATCGTG
AACGTATCCC CGAGCGTGTC GTTCATGCCA AGGGAGCCGG AGCCCATGGA TACTTCGAGG TCACCCATGA CATCACCAAG
TACTGTAAGG CCGATATGTT CAACAAGGTC GGAAAACAGA CACCACTTCT CGTTCGTTTT TCAACGGTCG CTGGAGAATC
GGGATCCGCT GATACTGTCC GCGATCCACG TGGATTCTCT CTCAAATTCT ATACCGAGGA GGGTAACTGG GATCTGGTTG
GAAATAACAC TCCGATCTTC TTCATTCGTG ACGCAATCCA CTTTCCGAAT TTCATTCATG CCCTGAAGCG CAATCCACAG
ACTCACATGA GGGATCCGAA TGCGCTCTTC GATTTCTGGA TGAATCGCCC TGAATCCATT CATCAGGTGA TGTTCCTCTA
CTCGGATCGT GGAATTCCTG ATGGATTCCG TTTTATGAAT GGATACGGAG CGCATACTTT CAAGATGGTC AACAAGGAGG
GAAATCCGAT TTATTGTAAA TTCCATTTCA AGCCTGCTCA AGGTTCCAAG AATCTCGATC CAACTGACGC TGGAAAGCTC
GCCTCTTCGG ATCCAGACTA TGCGATCCGC GACCTGTTCA ATGCCATTGA GTCAAGAAAT TTCCCGGAAT GGAAGATGTT
CATTCAAGTG ATGACATTCG AACAAGCTGA GAAATGGGAG TTCAATCCAT TTGATGTCAC TAAAGTTTGG CCACACGGTG
ATTACCCACT GATCGAGGTC GGCAAGATGG TGCTGAACAG GAATGTGAAG AATTATTTCG CTGAGGTCGA ACAAGCCGCC
TTCTGCCCGG CCCACATCGT CCCAGGAATC GAGTTCTCGC CAGACAAGAT GCTCCAAGGG CGTATCTTCT CCTACACGGA
CACGCATTAC CATCGCCTTG GACCAAACTA CATTCAGCTT CCAGTCAACT GCCCGTACCG CTCCCGTGCT CATACCACTC
AACGCGATGG TGCAATGGCT TATGAAAGCC AGGGAGATGC GCCGAATTAC TTCCCGAACA GTTTCCGCGG ATACCGTACT
CGTGATGATG TGAAGGAGTC GACATTTCAG ACGACTGGAG ATGTTGATCG TTATGAGACT GGAGACGATC ACAACTACGA
GCAGCCACGT CAGTTCTGGG AGAAAGTGCT CAAGGAGGAG GAGAGAGATC GGCTCGTTGG GAATTTGGCT AGTGATTTGG
GTGGCTGTTT GGAGGAAATT CAAAATGGAA TGGTCAAAGA GTTCACGAAA GTTCATCCGG ATTTCGGAAA TGCTCTTCGC
CATCAGCTCT GCCAGAAGAA GCATTAAatt
```

FIG. 24

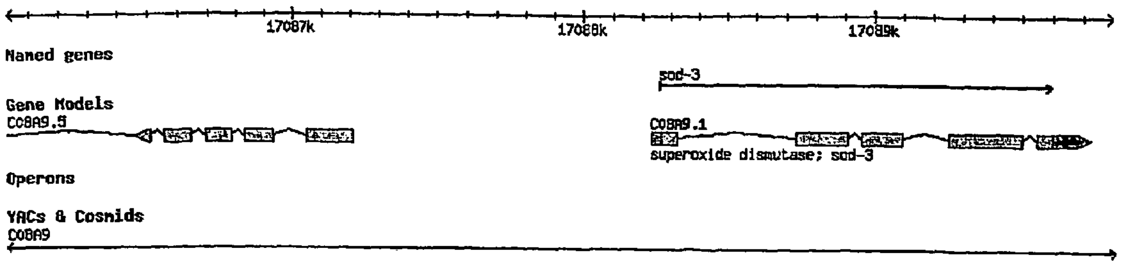

The *sod-3* gene is located on chromosome X. Exemplary regulatory sequences include:

TATTCGCAGAAAAAAGTCGTTGCAAACATTCGTTTTTATATGTTTTTCTTTGAGAAAGCGTGGTTCATTT
TTGAAAGTGAAAAATATTTGCTTAAAACTTCCAAATTTAAATCTGCAGTGATTCAGAGAGGTTGAGAATT
ATTTTCAAAAACATTCAATGTTTTCCCTTGGAGTGACTATGCAAATATGAAAATGTTTTCCAAAAATATT
TGGATGCCCTGATAAAAAGTAGGTGAAATTTCGCAGGGGAACATCATATTAAAATGTTGAATTTTTAGAA
GAAATGGAAATGTTTGTCGGTGGTATGCTCGAATATTTGAGATATTATATATTTACTGTTAAATCCGAAA
TTTTTGACAAACGGAAAAAATTTGTGTCGAAATACTACATTTTCGATAACACAAAGGTACTTCCATAACA
CTTATAAAAACTGTTTGACTATCTTATTTCAGGAAAAAAAAATCCAAGAATAAACATTTTTCAGAATTTG
AACTTTCTAATGGCTGATTAATAAAACAAAGTTATACAACTATTCAAAGCAGTTGCTCAATCTGGCATTT
TCTTGTGTTTTTTTTTGAATATTTCATCAGCAAGATGTTGATAATTTTGTGTTAATTCTAATTGTTTTCT
ACAATTTTTCAAACCGAAAATTGACCTTTGACTTTGTTTACTTTGTTCTCGTGGGTTAACTGTTCACTGA
TTTCTATTGCTGTTGATGAGGTCTTTGATCAAATTTGTATTGTTTTTATACTGCATATTGCTTCAATTCT
AAATCATCTAATATATTGTCAAACAACTTCTTGTTTTTTTTTCATTCAAAACTTCTGCAAAAACGTTCT
-287

CTTAACAAAGGTTCACACAACAACTCTCCTCTCCATCTCTTTCTCTCAACAACAATGTGCTGGCCTTGCA
TGTTTGCCAGTGCGGGTTGTTTACGCGTTTTCAAGATTTTTGGTCTCCTATCTAACGTCCCGAAATGCAT
TTTTTCCTTTCATTTGGTTTTTTTCTGTTCGAGAAAAGTGACCGTTTGTCAAATCTTCTAATTTTCAGTG
AATAAAATGCTG

FIG. 25

Exemplary sod-3 sequences:

Amino Acid Sequence

MLQSTARTAS KLVQPVAGVL AVRSKHTLPD LPFDYADLEP VISHEIMQLH HQKHHATYVN NLNQIEEKLH EAVSKGNLKE
AIALQPALKF NGGGHINHSI FWTNLAKDGG EPSKELMDTI KRDFGSLDNL QKRLSDITIA VQGSGWGWLG YCKKDKILKI
ATCANQDPLE GMVPLFGIDV WEHAYYLQYK NVRPDYVHAI WKIANWKNIS ERFANARQ

Spliced mRNA cgtttgtcaa atcttctaat tttcagtgaa taaaATGCTG CAATCTACTG CTCGCACTGC TTCAAAGCTT GTTCAACCGG
TTGCGGGAGT TCTCGCCGTC CGCTCCAAGC ACACTCTCCC AGATCTCCCA TTCGACTATG CAGATTTGGA ACCTGTAATC
AGCCATGAAA TCATGCAGCT TCATCATCAA AAGCATCATG CCACCTACGT GAACAATCTC AATCAGATCG AGGAGAAACT
TCACGAGGCT GTTTCGAAAG GGAATCTAAA AGAAGCAATT GCTCTCCAAC CAGCGCTGAA ATTCAATGGT GGTGGACACA
TCAATCATTC TATCTTCTGG ACCAACTTGG CTAAGGATGG TGGAGAACCT TCAAAGGAGC TGATGGACAC TATTAAGCGC
GACTTCGGTT CCCTGGATAA CTTGCAAAAA CGTCTTTCTG ACATCACTAT TGCGGTTCAA GGCTCTGGCT GGGGATGGTT
GGGATATTGC AAGAAAGACA AAATCTTGAA GATCGCCACC TGTGCAAACC AGGATCCTTT GGAAGGAATG GTCCCACTTT
TTGGAATTGA CGTTTGGGAG CACGCCTACT ACTTGCAGTA CAAAAATGTC CGCCCAGACT ATGTCCATGC TATTTGGAAG
ATTGCCAACT GGAAGAATAT CAGCGAGAGA TTTGCCAATG CTCGACAATA Aaagcaggaa atattggaat tttcggtttt
acgaaaatat tgaagataat tcagatgtag tttaaaacgc tgagaatttg tatttttgta attgtttaaa taaaagaacg
cacagttttt tctta

FIG. 26

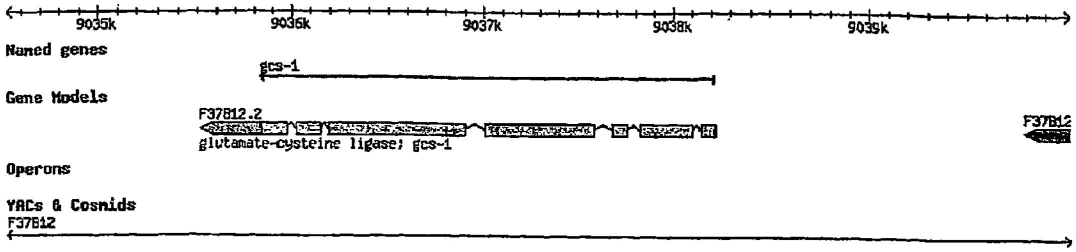

The *gcs-1* gene is located on chromosome II. An exemplary regulatory sequence is:

TTATCAACCACTAGGTTCCGTCTTAATCGTCCAAATATTGATCCGCTCGCTCGTGTTTTCTCAACTTCTTTATTTGCTGT
GTTTTTCTGTTTCTATAGTTCTCCATTTTCCATCTCCTCTTCGCTTGTTGAATGGACTTTATTTTGATAAGTTCATTTTA
ATTTTTCTAACAATCTCATCACTAGCTCATGATGACAATTGCAAAGAAATTCGTCATATAGAGGGGAAAAATGCTGACAA
-607

ATATTGAAAAGCCTTCAGGAGAGATGTAGAGACGTAGGAGTAGAGACAGAACATAAATTTGAGAAGCTTGTAGGGAGAAT
AGACATAGAGTTACCATGGGAAAAACGCTCGCATTTTCCATTTAACGAGATTTTCTAGATCACAACATTTTGTGATCCGT
TGTGCGAAAATCAAGCTTTTTATCAAACTTTTATCGTCTGTTCATTCTTTCTGACAATCTTTATTATCTTATTAAACTTG
ACTAATTGTATTGAAAGTATTTTTTTAGATGCGAACGAAGTTCCATTTTTCATGACTTAACATCTCTTAACGTTAGTGAA
-316

ATTTTTGAATTCCAATTAGGACTACGGTAGGAGTTCTGTAGTTGATTTCCTGAACACTTGTTTTGTAACCTTTCTGAACG
GATTTTAATATTTCTAAAATTTTAAATTGCAAATCTGAGTCCTATTAAAAGATGTTTCATCCGTAAAACCAACAAACAAA
ATATCACTTTATCATCATGAGATTTAATGTTTCCTTTTGATTTTCTGAATTGTTGTACTTTCCTTCAAACGACTTATTGA
-121

ACTGATGTAACTTTCCTTCTAATGTTATCATTTGTATTTTTTTGCAGAATG

FIG. 27

Exemplary gcs-1 sequences:

Amino Acid Sequence

```
MGLLTKGSPL TWAETVPHID YIKKHGIAQF INLYHRLKSR HGDQLKWGDE IEYTIVKFDD ANKKVRVSCK AEELLNKLQA
EEQVNAMLGT ANRFLWRPEF GSYMIEGTPG MPYGGLIACF NIVEANMKLR RQVVKKLLKK DETCLSISFP SLGVPGFTFP
EVAADRKNDD AANSVFWPEQ AVFLGHPRFK NLTKNIKGRR GSKVAINVPI FKDTNTPSPF VEDLSALGGP DDTRDAKPDH
IYMDHMGFGM GCCCLQVTFQ AVNVDEARWL YDQLTPITPI LLALSAATPI FRGKLSNVDS RWDIISASVD DRTPEERGLE
PLKNSKWVID KSRYDSTDCY IYPCSVGYND IPLQYDETIY KQLIDGNIDE PLAKHIAHMF IRDPHQVFRE RIEQDDEKSS
EHFETIQSSN WMNMRFKPPP PDAPEIGWRV EFRPTEVQLT DFENAAYCCF VVLLTRMMIS FRLTYLMPIS MVTENMKRAQ
QKDAVLNQKF LFRKGLAECK SAPENLKGSE KCGPPSQDIE EMSIDEIING KKNGFPGLIS LIRQFLDSAD VDVDTRCTIS
QYLNFISKRA TGEINTLAHW TRGFVQSHPA YKHDSDVNDN IVYDLLKKMD AISNGEDHCE KLLGCYRSKT DHAISAAVRK
AEEHMIVSSQ KRAH
```

Spliced mRNA

```
tttgcagaAT GGGTCTTTTG ACGAAAGGTA GTCCGTTGAC GTGGGCAGAA ACCGTACCGC ACATTGATTA TATCAAGAAG
CACGGAATTG CTCAATTCAT CAATCTCTAC CATCGTCTGA AATCAAGACA CGGAGATCAA TTGAAATGGG GAGATGAGAT
TGAATACACT ATTGTAAAAT TTGATGACGC AAACAAGAAA GTTCGCGTGT CGTGCAAAGC TGAAGAGCTT CTTAATAAGT
TACAAGCCGA AGAGCAGGTG AATGCGATGC TTGGAACTGC CAATCGATTC CTTTGGAGAC CAGAATTCGG ATCCTACATG
ATCGAGGGAA CCCCCGGAAT GCCTTACGGA GGTCTCATCG CTTGCTTCAA CATTGTCGAG GCAAACATGA AATTGCGCAG
ACAGGTCGTC AAAAAGTTAT TAAAGAAGGA TGAAACATGT CTATCGATAT CGTTCCCATC TCTTGGAGTA CCTGGATTCA
CATTCCCGGA AGTAGCAGCT GATAGAAAGA ATGATGATGC AGCTAATAGC GTTTTCTGGC CAGAACAAGC TGTATTCTTG
GGCCATCCAC GTTTCAAGAA TCTTACCAAA AATATTAAAG GTCGCAGAGG AAGTAAAGTA GCTATCAACG TCCCGATATT
CAAGGATACG AACACCCCCA GTCCATTCGT TGAAGATTTA TCTGCACTTG GAGGTCCTGA TGATACTCGT GATGCGAAAC
CTGATCACAT TTATATGGAT CATATGGGAT TCGGAATGGG GTGCTGTTGT CTTCAAGTCA CTTTCCAGGC TGTGAACGTC
GATGAAGCCA GATGGTTGTA CGATCAGCTG ACACCGATTA CACCGATTCT ACTGGCACTC TCTGCCGCCA CACCAATCTT
CCGTGGAAAA TTATCCAATG TCGATTCTAG ATGGGATATC ATTAGTGCAA GTGTCGACGA TCGTACACCG GAGGAAAGAG
GATTGGAACC TCTCAAGAAT TCGAAATGGG TTATTGATAA GAGTCGCTAC GACTCCACGG ACTGTTACAT TTATCCATGT
TCTGTTGGCT ACAATGATAT TCCTCTTCAA TACGACGAAA CCATATATAA ACAACTAATT GATGGAAATA TTGATGAGCC
ACTGGCAAAA CATATTGCGC ATATGTTCAT TCGTGATCCA CATCAAGTTT TCCGTGAGCG TATCGAACAG GACGATGAGA
AAAGCAGTGA ACACTTTGAA ACAATTCAAT CATCGAATTG GATGAACATG CGATTCAAGC CACCACCACC AGATGCTCCA
GAAATCGGAT GGAGAGTCGA ATTCCGGCCA ACTGAAGTTC AACTGACCGA CTTTGAAAAT GCAGCATACT GTTGCTTCGT
TGTATTGCTC ACCAGAATGA TGATCTCCTT CAGGCTGACA TATTTGATGC CAATTTCAAT GGTTACTGAA AATATGAAGC
GTGCTCAGCA AAAAGATGCA GTTCTCAATC AGAAATTCCT GTTCAGAAAA GGATTGGCTG AGTGCAAATC TGCTCCCGAA
AATTTGAAAG GATCGGAGAA ATGTGGACCA CCTAGTCAAG ATATTGAAGA AATGTCGATT GATGAGATTA TCAATGGAAA
GAAAAATGGA TTCCCAGGTC TCATTTCACT TATTCGCCAA TTTCTAGATT CTGCTGATGT TGATGTGGAT ACTCGGTGTA
CGATTTCTCA ATATTTGAAC TTTATTTCGA AACGAGCAAC TGGAGAGATT AATACTTTGG CTCACTGGAC ACGTGGATTC
GTACAATCTC ATCCTGCATA CAAACATGAC AGTGATGTAA ATGATAATAT AGTTTACGAT CTTTTGAAAA AGATGGATGC
CATCTCAAAC GGAGAAGATC ACTGTGAGAA GCTGCTCGGA TGCTACCGCT CTAAAACCGA TCATGCCATT TCTGCTGCTG
TTCGCAAAGC TGAAGAGCAC ATGATCGTGT CCAGCCAAAA ACGTGCACAT TAGgcgataa ttgattgatt atgtgatttt
aatttattta tgttctatac gtcgtgtttc ccattccttc taggccttcc atgattcaca atttttcgat gccatatcaa
tttagttggc catctacatt aaattactga tatgttgatg ctattttcta gtaagcagat gtcagtgttt agtaattcaa
aaatttaaac tctgaatttc taaatgcttg tttttgagt agtaggaatc agtacgaatg gtacattaat ctgaaaataa
tttcatattt atgtacaatg ctcccctgaa tccatcatat aattattatc cgtgttg
```

FIG. 28

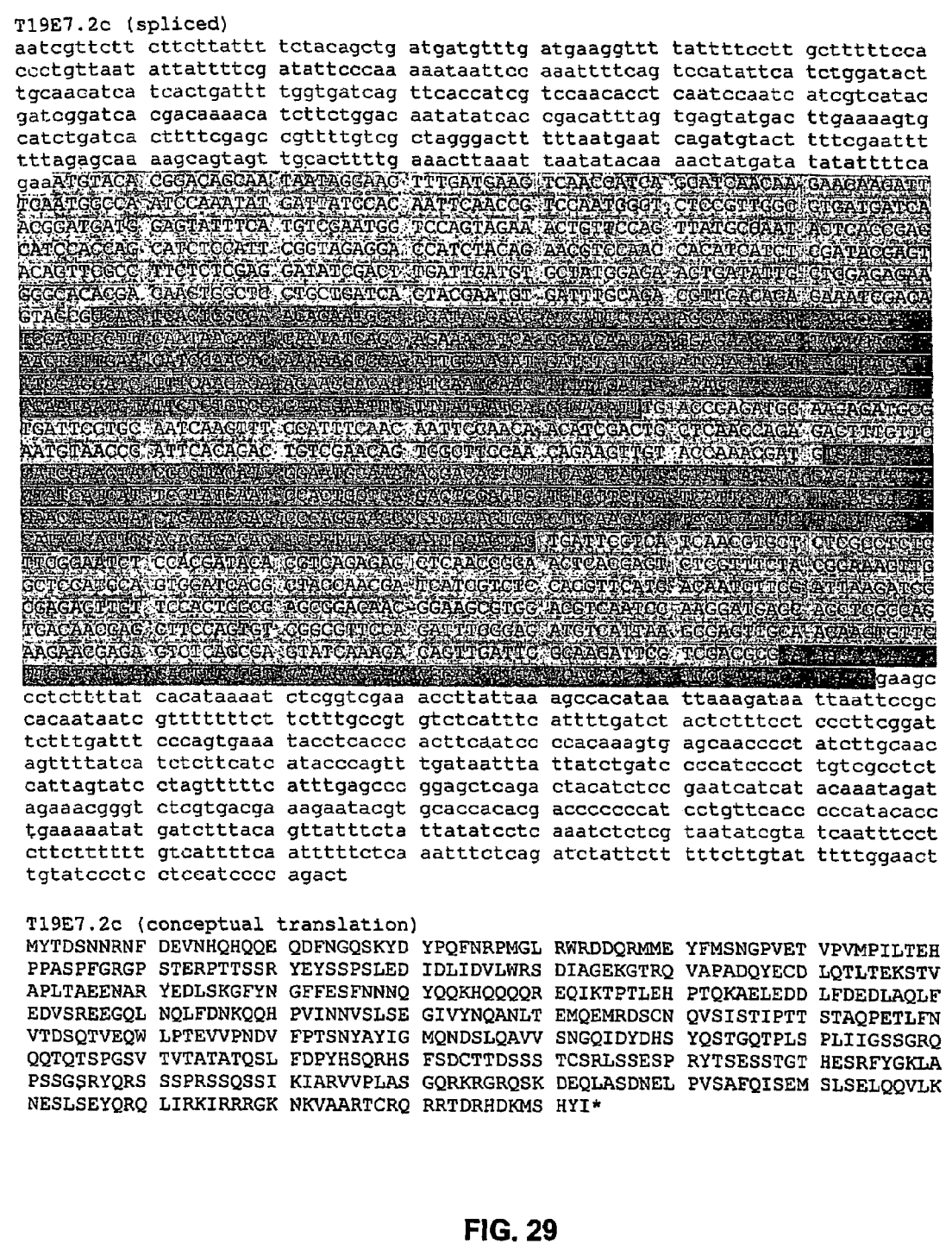

T19E7.2c (spliced)
aatcgttctt cttcttattt tctacagctg atgatgtttg atgaaggttt tattttcctt gctttttcca
ccctgttaat attattttcg atattcccaa aaataattcc aaattttcag tccatattca tctggatact
tgcaacatca tcactgattt tggtgatcag ttcaccatcg tccaacacct caatccaatc atcgtcatac
gatcggatca cgacaaaaca tcttctggac aatatatcac cgacatttag tgagtatgac ttgaaaagtg
catctgatca cttttcgagc cgttttgtcg ctagggactt tttaatgaat cagatgtact tttcgaattt
tttagagcaa aagcagtagt tgcacttttg aaacttaaat taatatacaa aactatgata tatattttca
gaaATGTACA CGGACAGCAA TAATAGGAAC TTTGATGAAG TCAACCATCA GCATCAACAA GAACAAGATT
TCAATGGCCA ATCCAAATAT GATTATCCAC AATTCAACCG TCCAATGGGT CTCCGTTGGC GTGATGATCA
ACGGATGATG GAGTATTTCA TGTCGAATGG TCCAGTAGAA ACTGTTCCAG TTATGCCAAT ACTCACCGAG
CATCCACCAG CATCTCCATT CGGTAGAGGA CCATCTACAG AACGTCCAAC CACATCATCT CGATACGAGT
ACAGTTCGCC TTCTCTCGAG GATATCGACT TGATTGATGT GCTATGGAGA AGTGATATTG CTGGAGAGAA
GGCCACACGA CAAGTGGCTC CTGCTGATCA GTACGAATGT GATTTGCAGA CGTTGACAGA GAAATCGACA
[illegible]
[illegible] ACCGAGATGC AAGAGATGCG
TGATTCCTGC AATCAAGTTT CCATTTCAAC AATTCCAACA ACATCGACTG CTCAACCAGA GACTTTGTTC
AATGTAACCG ATTCACAGAC TGTCGAACAG TGGCTTCCAA CAGAAGTTGT ACCAAACGAT G[illegible]
[illegible] TGATTCGTCA TCAACGTCCT CTCGCCTCTC
TTCGGAATCT CCACGATACA CGTCAGAGAC CTCAACCGGA ACTCACGAGT CTCGTTTCTA CGGAAAGTTG
GCTCCATCCA GTGGATCACG CTACCAACGA TCATGTCTCC CACGTTCATG ACAATCTTCG ATTAAGATCG
CGAGAGTTGT TCCACTGGCC AGCGGACAAC GGAAGCGTGG ACGTCAATCC AAGGATGAGC AGCTCGCCAG
TGACAACGAG CTTCCAGTGT CGGCGTTCCA GATTTCGGAG ATGTCATTAA GCGAGTTGCA ACAAGTCTTG
AAGAACGAGA GTCTCAGCGA GTATCAAAGA CAGTTGATTC GCAAGATTCG TCGACGCC[illegible]
[illegible]gaagc
cctcttttat cacataaaat ctcggtcgaa accttattaa agccacataa ttaaagataa ttaattccgc
cacaataatc gtttttttct tctttgccgt gtctcatttc attttgatct actctttcct cccttcggat
tctttgattt cccagtgaaa tacctcaccc acttcaatcc ccacaaagtg agcaacccct atcttgcaac
agttttatca tctcttcatc atacccagtt tgataattta ttatctgatc cccatcccct tgtcgcctct
cattagtatc ctagtttttc atttgagccc ggagctcaga ctacatctcc gaatcatcat acaaatagat
agaaacgggt ctcgtgacga aagaatacgt gcaccacacg accccccccat cctgttcacc cccatacacc
tgaaaaatat gatctttaca gttatttcta ttatatcctc aaatctctcg taatatcgta tcaatttcct
cttctttttt gtcattttca atttttctca aatttctcag atctattctt tttcttgtat ttttggaact
tgtatccctc ctccatcccc agact T19E7.2c (conceptual translation)
MYTDSNNRNF DEVNHQHQQE QDFNGQSKYD YPQFNRPMGL RWRDDQRMME YFMSNGPVET VPVMPILTEH
PPASPFGRGP STERPTTSSR YEYSSPSLED IDLIDVLWRS DIAGEKGTRQ VAPADQYECD LQTLTEKSTV
APLTAEENAR YEDLSKGFYN GFFESFNNNQ YQQKHQQQQR EQIKTPTLEH PTQKAELEDD LFDEDLAQLF
EDVSREEGQL NQLFDNKQQH PVINNVSLSE GIVYNQANLT EMQEMRDSCN QVSISTIPTT STAQPETLFN
VTDSQTVEQW LPTEVVPNDV FPTSNYAYIG MQNDSLQAVV SNGQIDYDHS YQSTGQTPLS PLIIGSSGRQ
QQTQTSPGSV TVTATATQSL FDPYHSQRHS FSDCTTDSSS TCSRLSSESP RYTSESSTGT HESRFYGKLA
PSSGSRYQRS SSPRSSQSSI KIARVVPLAS GQRKRGRQSK DEQLASDNEL PVSAFQISEM SLSELQQVLK
NESLSEYQRQ LIRKIRRRGK NKVAARTCRQ RRTDRHDKMS HYI*

FIG. 29

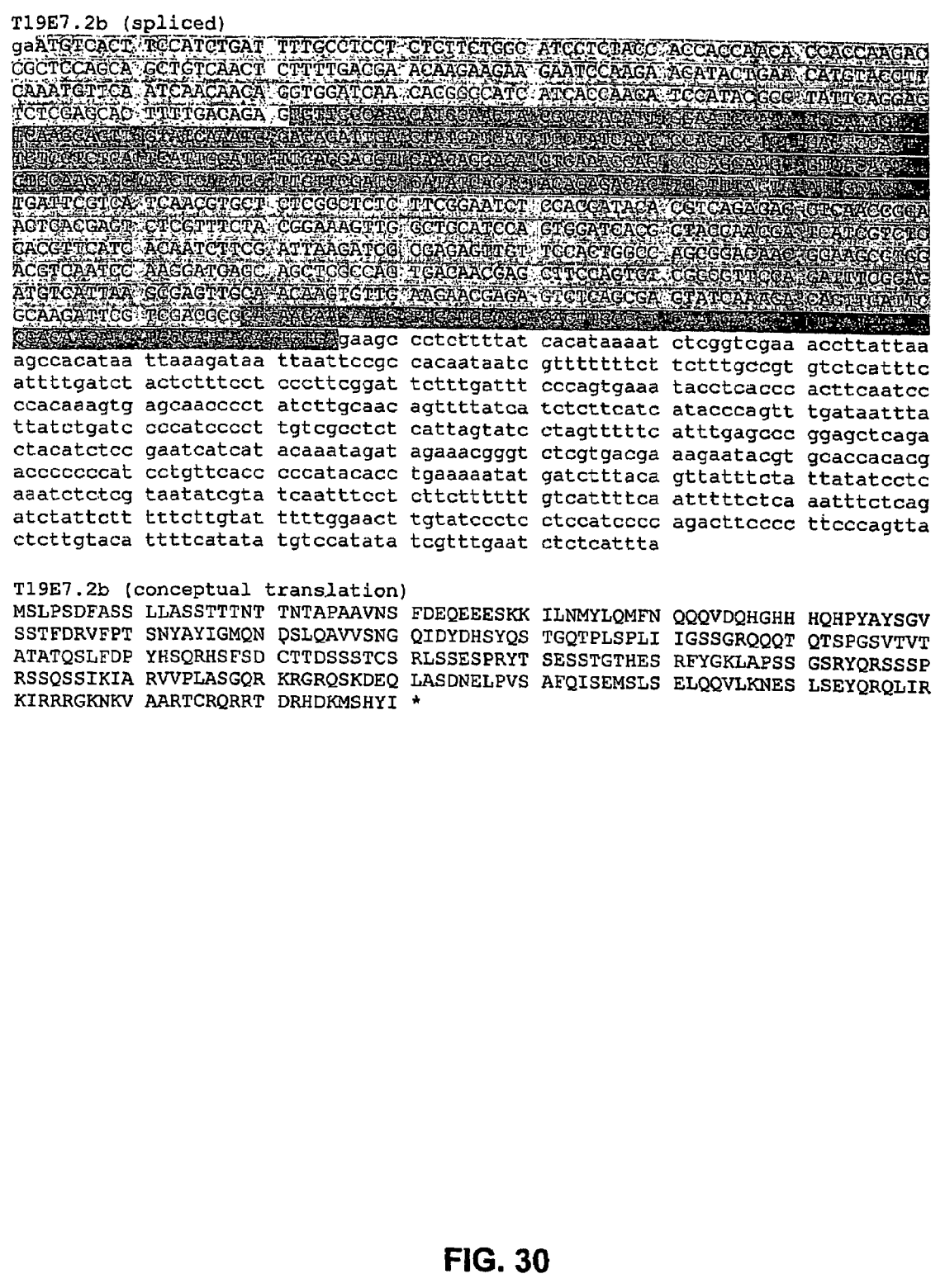

T19E7.2b (spliced)

```
gaATGTCACT TCCATCTGAT TTTGCCTCCT CTCTTCTGGC ATCCTCTACC ACCACCAACA CCACCAAGAC
CGCTCCAGCA GCTGTCAACT CTTTTGACGA ACAAGAAGAA GAATCCAAGA ACATACTGAA CATGTACCTT
CAAATGTTCA ATCAACAACA GGTGGATCAA CACGGCCATC ATCACCAAGA TCCATACGCC TATTCAGGAG
TCTCGAGCAC TTTTGACAGA G[illegible]
[illegible]
[illegible]
[illegible]
TGATTCGTCA TCAACGTGCT CTCGGCTCTC TTCGGAATCT CCACCATACA CGTCAGAGAG CTCAACCGGA
ACTCACGAGT CTCGTTTCTA CGGAAAGTTG GCTCCATCCA GTGGATCACG CTACCAACCA TCATCGTCTC
CACGTTCATC ACAATCTTCG ATTAAGATCG CGAGAGTTGT TCCACTGGCC AGCGGACAAC GGAAGCGTCG
ACGTCAATCC AAGGATGAGC AGCTCGCCAG TGACAACGAG CTTCCAGTGT CGGCGTTCCA GATTTCGGAG
ATGTCATTAA GCGAGTTGCA ACAAGTGTTG AAGAACGAGA GTCTCAGCGA GTATCAAAGA CAGTTGATTC
GCAAGATTCG TCGACGCCG[illegible]
[illegible]gaagc cctcttttat cacataaaat ctcggtcgaa accttattaa
agccacataa ttaaagataa ttaattccgc cacaataatc gttttttct tctttgccgt gtctcatttc
attttgatct actctttcct cccttcggat tctttgattt cccagtgaaa tacctcaccc acttcaatcc
ccacaaagtg agcaacccct atcttgcaac agttttatca tctcttcatc atacccagtt tgataattta
ttatctgatc cccatcccct tgtcgcctct cattagtatc ctagtttttc atttgagccc ggagctcaga
ctacatctcc gaatcatcat acaaatagat agaaacgggt ctcgtgacga aagaatacgt gcaccacacg
acccccccat cctgttcacc cccatacacc tgaaaaatat gatctttaca gttatttcta ttatatcctc
aaatctctcg taatatcgta tcaatttcct cttctttttt gtcattttca atttttctca aatttctcag
atctattctt tttcttgtat ttttggaact tgtatccctc ctccatcccc agacttcccc ttcccagtta
ctcttgtaca ttttcatata tgtccatata tcgtttgaat ctctcattta
```

T19E7.2b (conceptual translation)

```
MSLPSDFASS LLASSTTTNT TNTAPAAVNS FDEQEEESKK ILNMYLQMFN QQQVDQHGHH HQHPYAYSGV
SSTFDRVFPT SNYAYIGMQN QSLQAVVSNG QIDYDHSYQS TGQTPLSPLI IGSSGRQQQT QTSPGSVTVT
ATATQSLFDP YHSQRHSFSD CTTDSSSTCS RLSSESPRYT SESSTGTHES RFYGKLAPSS GSRYQRSSSP
RSSQSSIKIA RVVPLASGQR KRGRQSKDEQ LASDNELPVS AFQISEMSLS ELQQVLKNES LSEYQRQLIR
KIRRRGKNKV AARTCRQRRT DRHDKMSHYI *
```

FIG. 30

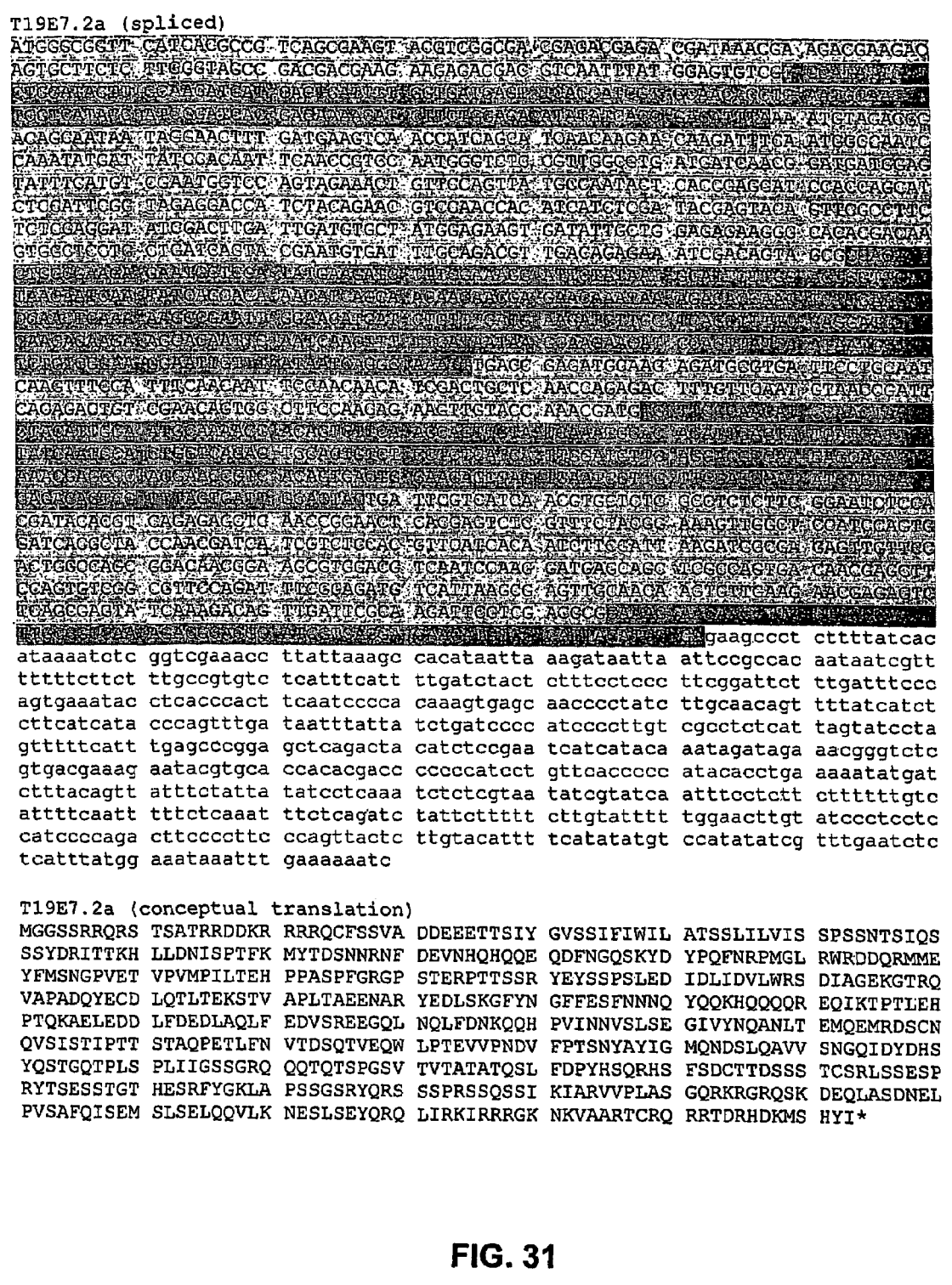

T19E7.2a (spliced)

ATGGSCGGTT CATCACGCCG TCAGCGAAGT ACGTCGGCGA CGAGACGAGA CGATAAACGA AGACGAAGAC
AGTGCTTCTC TTGGGTAGCC GACGACGAAG AAGAGACGAC GTCAATTTAT GGAGTGTCG[illegible]
[illegible]
[illegible] ATGTACAGCG
ACAGCAATAA TACCAACTTT GATGAAGTCA ACCATCAGCA TCAACAAGAA CAAGATTTCA ATGGCCAATC
CAAATATGAT TATCCACAAT TCAACCGTGC AATGGGTCTG CGTTGGCGTG ATCATCAACG GATGATGCAG
TATTTCATGT CGAATGGTCC AGTAGAAACT GTTCCAGTTA TGCCAATACT CACCGAGCAT CCACCAGCAT
CTCCATTCGG TAGAGGACCA TCTACAGAAC GTCCAACCAC ATCATCTCGA TACGAGTACA GTTCGCCTTC
TCTCGAGGAT ATCGACTTGA TTGATGTGCT ATGGAGAAGT GATATTGCTG GAGAGAAGGG CACACGACAA
GTGGCTCCTG CTGATCAGTA CGAATGTGAT TTGCAGACGT TGACAGAGAA ATCCACAGTA GCG[illegible]
[illegible]
[illegible]
[illegible]
[illegible]
[illegible]TGACC GAGATGCAAG AGATGCGTGA TTCCTGCAAT
CAAGTTTCCA TTTCAACAAT TCCAACAACA TCGACTGCTC AACCAGAGAC TTTGTTCAAT GTAACCCATT
CACAGACTGT CGAACAGTGG CTTCCAAGAG AAGTTGTACC AAACGATG[illegible]
[illegible]
[illegible]
[illegible]
[illegible]TGA TTCGTCATCA ACGTGCTCTC GCCTCTCTTC GGAATCTCCA
CGATACACGT CAGAGAGCTC AACCCGAACT CACGAGTCTC GTTTCTACGG AAAGTTGGCT CCATCCAGTG
GATCAGGCTA CCAACGATCA TCGTCTCCAC GTTCATCACA ATCTTCCATT AAGATCGCGA GAGTTGTTCC
ACTGGCCAGC GGACAACGGA AGCGTGGACG TCAATCCAAG GATGAGCAGC TCGCCAGTGA CAACGACCTT
CCAGTGTCGG CGTTCCAGAT TTCGGAGATG TCATTAAGCG AGTTGCAACA AGTCTTGAAG AACGAGAGTC
TCAGCGAGTA TCAAAGACAG TTGATTCGCA AGATTCGTCG AGCCG[illegible]
[illegible]gaagccct cttttatcac
ataaaatctc ggtcgaaacc ttattaaagc cacataatta aagataatta attccgccac aataatcgtt
tttttcttct ttgccgtgtc tcatttcatt ttgatctact ctttcctccc ttcggattct ttgatttccc
agtgaaatac ctcacccact tcaatcccca caaagtgagc aacccctatc ttgcaacagt tttatcatct
cttcatcata cccagtttga taatttatta tctgatcccc atccccttgt cgcctctcat tagtatccta
gtttttcatt tgagcccgga gctcagacta catctccgaa tcatcataca aatagataga aacgggtctc
gtgacgaaag aatacgtgca ccacacgacc cccccatcct gttcaccccc atacacctga aaaatatgat
ctttacagtt atttctatta tatcctcaaa tctctcgtaa tatcgtatca atttcctctt ctttttttgtc
attttcaatt tttctcaaat ttctcagatc tattcttttt cttgtatttt tggaacttgt atccctcctc
catcccccaga cttccccttc ccagttactc ttgtacattt tcatatatgt ccatatatcg tttgaatctc
tcatttatgg aaataaattt gaaaaaatc T19E7.2a (conceptual translation)

MGGSSRRQRS TSATRRDDKR RRRQCFSSVA DDEEETTSIY GVSSIFIWIL ATSSLILVIS SPSSNTSIQS
SSYDRITTKH LLDNISPTFK MYTDSNNRNF DEVNHQHQQE QDFNGQSKYD YPQFNRPMGL RWRDDQRMME
YFMSNGPVET VPVMPILTEH PPASPFGRGP STERPTTSSR YEYSSPSLED IDLIDVLWRS DIAGEKGTRQ
VAPADQYECD LQTLTEKSTV APLTAEENAR YEDLSKGFYN GFFESFNNNQ YQQKHQQQQR EQIKTPTLEH
PTQKAELEDD LFDEDLAQLF EDVSREEGQL NQLFDNKQQH PVINNVSLSE GIVYNQANLT EMQEMRDSCN
QVSISTIPTT STAQPETLFN VTDSQTVEQW LPTEVVPNDV FPTSNYAYIG MQNDSLQAVV SNGQIDYDHS
YQSTGQTPLS PLIIGSSGRQ QQTQTSPGSV TVTATATQSL FDPYHSQRHS FSDCTTDSSS TCSRLSSESP
RYTSESSTGT HESRFYGKLA PSSGSRYQRS SSPRSSQSSI KIARVVPLAS GQRKRGRQSK DEQLASDNEL
PVSAFQISEM SLSELQQVLK NESLSEYQRQ LIRKIRRRGK NKVAARTCRQ RRTDRHDKMS HYI*

FIG. 31

Human Glycogen synthase kinase-3 beta (GSK-3 beta).

```
  1 msgrprttsf aesckpvqqp safgsmkvsr dkdgskvttv vatpgqgpdr pqevsytdtk
 61 vigngsfgvv yqaklcdsge lvaikkvlqd krfknrelqi mrkldhcniv rlryffyssg
121 ekkdevylnl vldyvpetvy rvarhysrak qtlpviyvkl ymyqlfrsla yihsfgichr
181 dikpqnllld pdtavlklcd fgsakqlvrg epnvsyicsr yyrapelifg atdytssidv
241 wsagcvlael llgqpifpgd sgvdqlveii kvlgtptreq iremnpnyte fkfpqikahp
301 wtkvfrprtp peaialcsrl leytptarlt pleacahsff delrdpnvkl pngrdtpalf
361 nfttqelssn pplatilipp hariqaaast ptnataasda ntgdrgqtnn aasasasnst
```

FIG. 32

Human Glycogen synthase kinase-3 alpha (GSK-3 alpha).

```
  1 msgggpsggg pggsgrarts sfaepggggg gggggpggsa sgpggtgggk asvgamgggv
 61 gasssgggpg gsgggsggp gagtsfpppg vklgrdsgkv ttvvatlgqg persqevayt
121 dikvigngsf gvvyqarlae trelvaikkv lqdkrfknre lqimrkldhc nivrlryffy
181 ssgekkdely lnlvleyvpe tvyrvarhft kakltipily vkvymyqlfr slayihsqgv
241 chrdikpqnl lvdpdtavlk lcdfgsakql vrgepnvsyi csryyrapel ifgatdytss
301 idvwsagcvl aelllgqpif pgdsgvdqlv eiikvlgtpt reqiremnpn ytefkfpqik
361 ahpwtkvfks rtppeaialc sslleytpss rlspleacah sffdelrclg tqlpnnrplp
421 plfnfsagel siqpslnail ipphlrspag tttltpssqa ltetptssdw qstdatptlt
481 nss
```

FIG. 33

Mouse Glycogen synthase kinase-3 beta.

```
  1 msgrprttsf aesckpvqqp safgsmkvsr dkdgskvttv vatpgqgpdr pqevsytdtk
 61 vigngsfgvv yqaklcdsge lvaikkvlqd krfknrelqi mrkldhcniv rlryffyssg
121 ekkdevylnl vldyvpetvy rvarhysrak qtlpviyvkl ymyqlfrsla yihsfgichr
181 dikpqnllld pdtavlklcd fgsakqlvrg epnvsyicsr yyrapelifg atdytssidv
241 wsagcvlael llgqpifpgd sgvdqlveii kvlgtptreq iremnpnyte fkfpqikahp
301 wtkvfrprtp peaialcsrl leytptarlt pleacahsff delrdpnvkl pngrdtpalf
361 nfttqelssn pplatilipp hariqaaasp panataasdt nagdrgqtnn aasasasnst
```

FIG. 34

Mouse Glycogen synthase kinase-3 alpha (GSK-3 alpha).

```
  1 masttamdvl eelssdssek qrsvnildsf vkdmferias easflarqar nstinsreiq
 61 tairlllpge lcrrgtgcgk asvwamgggv gasssgvggg sggpgstsfl qpgvklghds
121 rkvttvvatv gqdpersqev actdikvign gsfgvvyqew ladtrelvai kkvlqdkrfk
181 yrelqimckl dhcnivrlqy ffyssgekkd dlylnlvley vpetvyxvar hftkakliip
241 iiyvkvymyq lfrslayihs qgvchrdinl lvdpdtailk lcdfgsakql vlgttvapel
301 ytssidvxsa gcvlaellls qpifpgdngv dqlveiikvl gtptreqire mnpkytefkf
361 pqikahpwtk vfksrtaprp lhsalacwst hhtqgsphlr lvptaslmnc gvsgpapqrp
421 ptspcstsvl vicpsnhlsm pfssllt
```

FIG. 35

GSK-3 [*Caenorhabditis elegans*].

```
  1 mnkqllscsl ksgkqvtmvv asvatdgvdq qveisyydqk vigngsfgvv flaklsttne
 61 mvaikkvlqd krfknrelqi mrklnhpniv klkyffyssg ekkdelylnl ileyvpetvy
121 rvarhyskqr qqipmiyvkl ymyqllrsla yihsigichr dikpqnllid pesgvlklcd
181 fgsakylvrn epnvsyicsr yyrapelifg atnytnsidv wsagtvmael llgqpifpgd
241 sgvdqlveii kvlgtptreq iqsmnpnyke fkfpqikahp wnkvfrvhtp aeaidliski
301 ieytptsrpt pqaacqhaff delrnpdarl psgrplptle mdgpmgtgei sptsgdvagp
361 sa
```

FIG. 36

***sgg-1* (GSK-3) inhibits constitutive SKN-1 nuclear accumulation and induction of its target gene *gcs-1*.**

Ala substitution at a predicted GSK-3 phosphorylation site results in nuclear localization of SKN-1

SKN-1 AND GSK-3 GENES AND PROTEINS

RELATED APPLICATIONS

The present application is the National Stage of International Application No. PCT/US2004/019046, filed Jun. 14, 2004, which claims the benefit of U.S. Ser. No. 60/478,185 filed Jun. 13, 2003. The contents of the above applications are hereby incorporated by reference in their entirety.

STATEMENT AS TO FEDERALLY SPONSORED RESEARCH

This invention was made with Government support under National Institutes of Health Grant Nos. RO1GM50900 and RO1GM62891. The Government has certain rights in this invention.

TECHNICAL FIELD

This invention generally relates to the SKN-1 and GSK-3 genes and proteins, and their use in screening methods for isolating modulators of an oxidative stress response pathway.

BACKGROUND

In diverse organisms, a common mesendodermal tissue field gives rise to the endoderm and a mesoderm subset that forms the heart and blood in vertebrates. In the nematode *Caenorhabditis elegans*, mesendodermal development is initiated by the maternally expressed transcription factor SKN-1, which specifies the fate of a single cell, the EMS blastomere. The EMS daughter cell E becomes the endoderm, which consists of the intestine. Its sister cell MS gives rise to mesodermal derivatives that include the pharynx, a feeding pump that is analogous to the heart, and coelomocytes that resemble macrophages. In these embryonic cells SKN-1 induces expression of the GATA factors MED-1 and MED-2, which are required for differentiation of EMS lineages. *C. elegans* skn-1 mutants are sensitive to oxidative stress and have shortened lifespans.

In vertebrates, Nrf proteins activate transcription of genes encoding the Phase II detoxification enzymes, which constitute the primary cellular defense against oxidative stress. Essentially all organisms must defend themselves against reactive oxygen species (ROS), which are derived from both mitochondrial respiration and exogenous sources. Phase II enzymes synthesize the critical reducing agent glutathione, scavenge ROS directly, and detoxify reactive intermediates that are generated when xenobiotics are metabolized by the cytochrome p450 (Phase I) enzymes. Through Nrf2, exposure to oxidative stress or particular classes of chemicals induces Phase II enzyme gene expression in a variety of tissues, including the liver and digestive tract. This mechanism also constitutes the major response to chemoprotective antioxidants, including many natural compounds, which thereby stimulate xenobiotic detoxification and inhibit carcinogen-induced tumorigenesis. Accordingly, mice that lack Nrf2 are abnormally susceptible to drug toxicity and carcinogenesis, and do not respond to chemoprotective antioxidants.

SUMMARY

The present invention is based in part on the discovery that SKN-1 is required for oxidative stress resistance and longevity in *C. elegans*. It has been discovered that SKN-1 orchestrates a major oxidative stress response in *C. elegans*, similar to Nrf proteins in vertebrates, in addition to initiating embryonic development of the *C. elegans* mesendoderm. The present invention is also based in part on the discovery that SKN-1 is modulated by GSK-3.

Accordingly, the present invention features in vivo and in vitro methods for determining whether a test compound is a candidate compound capable of modulating stress response, e.g., oxidative stress response, e.g., SKN-1-mediated oxidative stress response. For example, in one aspect the invention features methods for determining whether a test compound is a candidate stress response-activating compound, e.g., a candidate oxidative stress response-activating compound, e.g., a candidate SKN-1-mediated oxidative stress response-activating compound. In one embodiment, the method includes (a) contacting a GSK-3 polypeptide, or fragment thereof (e.g., an SKN-1 binding fragment), or a GSK-3 DNA with a test compound; (b) determining whether the test compound interacts with the GSK-3 polypeptide, or fragment thereof (e.g., SKN-1 binding fragment), or GSK-3 DNA; and (c) if the test compound interacts with the GSK-3 polypeptide, or fragment thereof (e.g., an SKN-1 binding fragment), or GSK-3 DNA, identifying the test compound as a candidate compound capable of activating a stress response, e.g., an oxidative stress response, e.g., an SKN-1-mediated oxidative stress response.

In another embodiment, the method includes: (a) providing a GSK-3 polypeptide, or fragment thereof, e.g., a SKN-1 binding fragment thereof, and a SKN-1 polypeptide, or fragment thereof, e.g., a GSK-3 binding fragment thereof; (b) contacting the polypeptides or fragments thereof with a test compound; (c) determining whether the test compound decreases the interaction between the GSK-3 polypeptide, or fragment thereof, and the SKN-1 polypeptide, or fragment thereof, wherein a decrease in the interaction between the GSK-3 polypeptide, or fragment thereof, and the SKN-1 polypeptide, or fragment thereof, indicates that the test compound is a candidate stress response-activating compound, e.g., a candidate oxidative stress response-activating compound, e.g., a candidate SKN-1-mediated oxidative stress response-activating compound.

In another embodiment, the method includes: (a) providing a nematode, e.g., a *C. elegans*, capable of expressing a SKN-1 polypeptide and containing at least one transgene including: (i) an oxidative stress resistance gene promoter, e.g., a promoter of a γ-glutamine cysteine synthase heavy chain, glutathione synthetase, NADH quinone oxidoreductase, superoxide dismutase, catalase, or glutathione S-transferase gene, operably linked to (ii) a reporter gene, e.g., a gene encoding green fluorescent protein, chloramphenicol acetyl transferase, β glucuronidase, or luciferase; and (b) contacting the nematode, e.g., a *C. elegans*, with a test compound; and (c) determining whether expression of the transgene is increased, wherein an increase in expression of the transgene indicates that the test compound is a candidate stress response-activating compound, e.g., a candidate oxidative stress response-activating compound, e.g., a candidate SKN-1-mediated oxidative stress response-activating compound.

In one embodiment, the method further includes a confirmatory step carried out after a candidate compound is identified. The confirmatory step can include providing a second nematode, e.g., a second *C. elegans*, not contacted with the candidate compound, to determine whether the candidate compound increases the SKN-1-mediated oxidative stress response of the first nematode, e.g., *C. elegans*, relative to the SKN-1-mediated oxidative stress response of the second nematode, e.g., the second *C. elegans*, not contacted with the candidate compound, wherein a candidate compound that increases SKN-1-mediated oxidative stress response in the first nematode relative to the second nematode is an SKN-1-mediated oxidative stress response-activating agent. In one embodiment, the confirmatory step includes providing a nematode, e.g., a *C. elegans*, not capable of expressing a SKN-1 polypeptide (e.g., a skn-1 mutant) and containing at least one transgene including: (i) an oxidative stress resistance gene promoter, e.g., a promoter of a γ-glutamine cysteine synthase heavy chain, glutathione synthetase, NADH quinone oxidoreductase, superoxide dismutase, catalase, or glutathione S-transferase gene, operably linked to (ii) a reporter gene, e.g., a gene encoding green fluorescent protein, chloramphenicol acetyl transferase, β glucuronidase, or luciferase; and contacting the nematode with the candidate compound, wherein no increase in expression of the transgene indicates that the candidate compound is a stress response-activating agent, e.g., an oxidative stress response-activating agent, e.g., an SKN-1-mediated oxidative stress response-activating agent.

In one embodiment, the method further includes determining whether the candidate compound is an inhibitor of GSK-3 by: (a) contacting a GSK-3 polypeptide or GSK-3 DNA with the candidate compound; and (b) detecting interaction of the candidate compound with the GSK-3 polypeptide or GSK-3 DNA, wherein an interaction indicates that the candidate compound is an inhibitor of GSK-3.

In another embodiment, the method includes: (a) providing a cell, e.g., a cultured cell, e.g., a cultured nematode or cultured mammalian cell, capable of expressing a SKN-1 polypeptide and containing at least one transgene including: (i) an oxidative stress resistance gene promoter, e.g., a promoter of a γ-glutamine cysteine synthase heavy chain, glutathione synthetase, NADH quinone oxidoreductase, superoxide dismutase, catalase, or glutathione S-transferase gene, operably linked to (ii) a reporter gene, e.g., a gene encoding green fluorescent protein, chloramphenicol acetyl transferase, β glucuronidase, or luciferase; and (b) contacting the cell, e.g., the cultured cell, e.g., the cultured nematode or cultured mammalian cell, with a test compound; and (c) determining whether expression of the transgene is increased, wherein an increase in expression of the transgene indicates that the test compound is a candidate stress response-activating compound, e.g., a candidate oxidative stress response-activating compound, e.g., a candidate SKN-1-mediated oxidative stress response-activating compound.

In one embodiment, the method further includes a confirmatory step carried out after a candidate compound is identified. The confirmatory step can include providing a second cell, e.g., a second cultured cell, e.g., a second cultured nematode cell or second cultured mammalian cell, not contacted with the candidate compound to determine whether the candidate compound increases the SKN-1-mediated oxidative stress response of the first cell, e.g., the first cultured cell, e.g., the first cultured nematode cell or first cultured mammalian cell, relative to the SKN-1-mediated oxidative stress response of the second cell, e.g., the second cultured cell, e.g., the second cultured nematode cell or second cultured mammalian cell, not contacted with the candidate compound, wherein a candidate compound that increases SKN-1-mediated oxidative stress response in the first cell relative to the second cell is an SKN-1-mediated oxidative stress response-activating agent. In one embodiment, the confirmatory step includes providing a cell, e.g., a cultured cell, e.g., a cultured nematode cell or cultured mammalian cell, not capable of expressing a SKN-1 polypeptide (e.g., a skn-1 mutant cell) and containing at least one transgene including: (i) an oxidative stress resistance gene promoter, e.g., a promoter of a γ-glutamine cysteine synthase heavy chain, glutathione synthetase, NADH quinone oxidoreductase, superoxide dismutase, catalase, or glutathione S-transferase gene, operably linked to (ii) a reporter gene, e.g., a gene encoding green fluorescent protein, chloramphenicol acetyl transferase, β glucuronidase, or luciferase; and contacting the cell with the candidate compound, wherein no increase in expression of the transgene indicates that the candidate compound is a stress response-activating agent, e.g., an oxidative stress response-activating agent, e.g., an SKN-1-mediated oxidative stress response-activating agent.

In one embodiment, the method further includes determining whether the candidate compound is an inhibitor of GSK-3 by: (a) contacting a GSK-3 polypeptide or GSK-3 DNA with the candidate compound; and (b) detecting interaction of the candidate compound with the GSK-3 polypeptide or GSK-3 DNA, wherein an interaction indicates that the candidate compound is an inhibitor of GSK-3.

In another embodiment, the method includes: (a) providing a nematode, e.g., a *C. elegans*, containing a transgene encoding a SKN-1 fusion protein, wherein the transgene comprises: (i) a SKN-1 DNA operably linked to (ii) a reporter gene, e.g., a gene encoding green fluorescent protein, chloramphenicol acetyl transferase, β glucuronidase, or luciferase; (b) contacting the nematode, e.g., *C. elegans*, with a test compound; and (c) determining whether the SKN-1 fusion protein accumulates in cell nuclei in the nematode, wherein increased accumulation indicates that the test compound is a candidate stress response-activating compound, e.g., a candidate oxidative stress response-activating compound, e.g., a candidate SKN-1-mediated oxidative stress response-activating compound.

In one embodiment, the method further includes a confirmatory step carried out after a candidate compound is identified. The confirmatory step can include providing a second nematode, e.g., a second *C. elegans*, not contacted with the candidate compound to determine whether the candidate compound increases the SKN-1-mediated oxidative stress response of the first nematode, e.g., *C. elegans*, relative to the SKN-1-mediated oxidative stress response of the second nematode, e.g., the second *C. elegans*, not contacted with the candidate compound, wherein a candidate compound that increases SKN-1-mediated oxidative stress response in the first nematode relative to the second nematode is an SKN-1-mediated oxidative stress response-activating agent. In one embodiment, the confirmatory step includes providing a nematode, e.g., a *C. elegans*, not capable of expressing a SKN-1 polypeptide (e.g., a skn-1 mutant) and containing at least one transgene including: (i) an oxidative stress resistance gene promoter, e.g., a promoter of a γ-glutamine cysteine synthase heavy chain, glutathione synthetase, NADH quinone oxidoreductase, superoxide dismutase, catalase, or glutathione S-transferase gene, operably linked to (ii) a reporter gene, e.g., a gene encoding green fluorescent protein, chloramphenicol acetyl transferase, β glucuronidase, or luciferase; and contacting the nematode with the candidate compound, wherein no increase in expression of the transgene indicates that the candidate compound is a stress response-activating agent, e.g., an oxidative stress response-activating agent, e.g., an SKN-1-mediated oxidative stress response-activating agent.

In one embodiment, the method further includes determining whether the candidate compound is an inhibitor of GSK-3 by: (a) contacting a GSK-3 polypeptide or GSK-3 DNA with the candidate compound; and (b) detecting interaction of the candidate compound with the GSK-3 polypeptide or GSK-3 DNA, wherein an interaction indicates that the candidate compound is an inhibitor of GSK-3.

In another embodiment, the method includes: (a) providing a cell, e.g., a cultured cell, e.g., a cultured nematode or a cultured mammalian cell, containing a transgene encoding a SKN-1 fusion protein, wherein the transgene comprises: (i) a SKN-1 DNA operably linked to (ii) a reporter gene, e.g., a gene encoding green fluorescent protein, chloramphenicol acetyl transferase, β glucuronidase, or luciferase; (b) contacting the cell, e.g., the cultured cell, e.g., the cultured nematode or cultured mammalian cell, with a test compound; and (c) determining whether the SKN-1 fusion protein accumulates in the nucleus of the cell, e.g., the cultured cell, e.g., the cultured nematode or cultured mammalian cell, wherein increased accumulation indicates that the test compound is a candidate stress response-activating compound, e.g., a candidate oxidative stress response-activating compound, e.g., a candidate SKN-1-mediated oxidative stress response-activating compound.

In one embodiment, the method further includes a confirmatory step carried out after a candidate compound is identified. The confirmatory step can include providing a second cell, e.g., a second cultured cell, e.g., a second cultured nematode cell or second cultured mammalian cell, not contacted with the candidate compound to determine whether the candidate compound increases the SKN-1-mediated oxidative stress response of the first cell, e.g., the first cultured cell, e.g., the first cultured nematode cell or first cultured mammalian cell, relative to the SKN-1-mediated oxidative stress response of the second cell, e.g., the second cultured cell, e.g., the second cultured nematode cell or second cultured mammalian cell, not contacted with the candidate compound, wherein a candidate compound that increases SKN-1-mediated oxidative stress response in the first cell relative to the second cell is an SKN-1-mediated oxidative stress response-activating agent. In one embodiment, the confirmatory step includes providing a cell, e.g., a cultured cell, e.g., a cultured nematode cell or cultured mammalian cell, not capable of expressing a SKN-1 polypeptide (e.g., a skn-1 mutant cell) and containing at least one transgene including: (i) an oxidative stress resistance gene promoter, e.g., a promoter of a γ-glutamine cysteine synthase heavy chain, glutathione synthetase, NADH quinone oxidoreductase, superoxide dismutase, catalase, or glutathione S-transferase gene, operably linked to (ii) a reporter gene, e.g., a gene encoding green fluorescent protein, chloramphenicol acetyl transferase, β glucuronidase, or luciferase; and contacting the cell with the candidate compound, wherein no increase in expression of the transgene indicates that the candidate compound is a stress response-activating agent, e.g., an oxidative stress response-activating agent, e.g., an SKN-1-mediated oxidative stress response-activating agent.

In one embodiment, the method further includes determining whether the candidate compound is an inhibitor of GSK-3 by: (a) contacting a GSK-3 polypeptide or GSK-3 DNA with the candidate compound; and (b) detecting interaction of the candidate compound with the GSK-3 polypeptide or GSK-3 DNA, wherein an interaction indicates that the candidate compound is an inhibitor of GSK-3.

In another aspect, the invention features methods for determining whether a test compound is a candidate stress response-inhibiting compound, e.g., a candidate oxidative stress response-inhibiting compound, e.g., a candidate SKN-1-mediated oxidative stress response-inhibiting compound. In one embodiment, the method includes (a) contacting a SKN-1 polypeptide, or fragment thereof, or a SKN-1 DNA with a test compound; (b) determining whether the test compound interacts with the SKN-1 polypeptide, or fragment thereof, or SKN-1 DNA; and (c) if the test compound interacts with the SKN-1 polypeptide, or fragment thereof, or SKN-1 DNA, identifying the test compound as a candidate stress response-inhibiting compound, e.g., a candidate oxidative stress response-inhibiting compound, e.g., a candidate SKN-1-mediated oxidative stress response-inhibiting compound.

In another embodiment, the method includes: (a) providing (i) a SKN-1 polypeptide, or fragment thereof, and (ii) an oxidative stress resistance gene, e.g., a gene encoding γ-glutamine cysteine synthase heavy chain, glutathione synthetase, NADH quinone oxidoreductase, superoxide dismutase, catalase, or glutathione S-transferase, or SKN-1 polypeptide-binding fragments thereof; (b) contacting the SKN-1 polypeptide, or fragment thereof, and the oxidative stress resistance gene, or SKN-1 polypeptide-binding fragment thereof, with a test compound; and (c) determining whether the SKN-1 polypeptide, or fragment thereof, and the oxidative stress resistance gene, or SKN-1 polypeptide-binding fragment thereof, interact in the presence of the test compound, wherein a decrease in interaction indicates that the test compound is a candidate stress response-inhibiting compound, e.g., a candidate oxidative stress response-inhibiting compound, e.g., a candidate SKN-1-mediated oxidative stress response-inhibiting compound.

In another embodiment, the method includes: (a) providing a nematode, e.g., a *C. elegans*, capable of expressing a SKN-1 polypeptide and containing at least one transgene including: (i) an oxidative stress resistance gene promoter, e.g., a promoter of a γ-glutamine cysteine synthase heavy chain, glutathione synthetase, NADH quinone oxidoreductase, superoxide dismutase, catalase, or glutathione S-transferase gene, operably linked to (ii) a reporter gene, e.g., a gene encoding green fluorescent protein, chloramphenicol acetyl transferase, β glucuronidase, or luciferase; (b) contacting the nematode, e.g., *C. elegans*, with a test compound; (c) before, during, or after step (b), subjecting the nematode, e.g., *C. elegans*, to conditions that activate the SKN-1-mediated oxidative stress response in the absence of the test compound; and (d) determining whether expression of the transgene, e.g., a transgene described herein, is decreased or unchanged, wherein decreased or unchanged expression of the transgene indicates that the test compound is a candidate stress response-inhibiting compound, e.g., a candidate oxidative stress response-inhibiting compound, e.g., a candidate SKN-1-mediated oxidative stress response-inhibiting compound.

In one embodiment, the method further includes a confirmatory step carried out after a candidate compound is identified. The confirmatory step can include providing a second nematode, e.g., a second *C. elegans*, not contacted with the candidate compound to determine whether the candidate compound decreases the SKN-1-mediated oxidative stress response of the first nematode, e.g., *C. elegans*, relative to the SKN-1-mediated oxidative stress response of the second nematode, e.g., the second *C. elegans*, not contacted with the candidate compound, wherein a candidate compound that decreases SKN-1-mediated oxidative stress response in the first nematode relative to the second nematode is a stress response-inhibiting agent, e.g., an oxidative stress response-inhibiting agent, e.g., an SKN-1-mediated oxidative stress response-inhibiting agent.

In one embodiment, the method further includes determining whether the candidate compound is an inhibitor of SKN-1 by: (a) contacting a SKN-1 polypeptide or SKN-1 DNA with the candidate compound; and (b) detecting interaction of the candidate compound with the SKN-1 polypeptide or SKN-1 DNA, wherein an interaction indicates that the candidate compound is an inhibitor of SKN-1.

In another embodiment, the method includes: (a) providing a cell, e.g., a cultured cell, e.g., a cultured nematode or cultured mammalian cell, capable of expressing a SKN-1 polypeptide and containing at least one transgene including: (i) an oxidative stress resistance gene promoter, e.g., a promoter of a γ-glutamine cysteine synthase heavy chain, glutathione synthetase, NADH quinone oxidoreductase, superoxide dismutase, catalase, or glutathione S-transferase gene, operably linked to (ii) a reporter gene, e.g., a gene encoding green fluorescent protein, chloramphenicol acetyl transferase, β glucuronidase, or luciferase; (b) contacting the cell, e.g., the cultured cell, e.g., the cultured nematode or cultured mammalian cell, with a test compound; (c) before, during, or after step (b), subjecting the cell, e.g., the cultured cell, e.g., the cultured nematode or cultured mammalian cell, to conditions that activate the SKN-1-mediated oxidative stress response in the absence of the test compound; and (d) determining whether expression of the transgene, e.g., a transgene described herein, is decreased or unchanged, wherein decreased or unchanged expression of the transgene indicates that the test compound is a candidate stress response-inhibiting compound, e.g., a candidate oxidative stress response-inhibiting compound, e.g., a candidate SKN-1-mediated oxidative stress response-inhibiting compound.

In one embodiment, the method further includes a confirmatory step carried out after a candidate compound is identified. The confirmatory step can include providing a second cell, e.g., a second cultured cell, e.g., a second cultured nematode cell or second cultured mammalian cell, not contacted with the candidate compound, to determine whether the candidate compound decreases the SKN-1-mediated oxidative stress response of the first cell, e.g., the first cultured cell, e.g., the first cultured nematode cell or first cultured mammalian cell, relative to the SKN-1-mediated oxidative stress response of the second cell, e.g., the second cultured cell, e.g., the second cultured nematode cell or second cultured mammalian cell, not contacted with the candidate compound, wherein a candidate compound that decreases SKN-1-mediated oxidative stress response in the first cell relative to the second cell is a stress response-inhibiting agent, e.g., an oxidative stress response-inhibiting agent, e.g., an SKN-1-mediated oxidative stress response-inhibiting agent.

In one embodiment, the method further includes determining whether the candidate compound is an inhibitor of SKN-1 by: (a) contacting a SKN-1 polypeptide or SKN-1 DNA with the candidate compound; and (b) detecting interaction of the candidate compound with the SKN-1 polypeptide or SKN-1 DNA, wherein an interaction indicates that the candidate compound is an inhibitor of SKN-1.

In another embodiment, the method includes: (a) providing a nematode, e.g., a *C. elegans*, containing a transgene encoding a SKN-1 fusion protein, wherein the transgene comprises: (i) a SKN-1 DNA operably linked to (ii) a reporter gene, e.g., a gene encoding green fluorescent protein, chloramphenicol acetyl transferase, βglucuronidase, or luciferase; (b) contacting the nematode, e.g., *C. elegans*, with a test compound; (c) before or during step (b), subjecting the nematode, e.g., *C. elegans*, to conditions that activate the SKN-1-mediated oxidative stress response in the absence of the test compound; and (d) determining whether the SKN-1 fusion protein accumulates in cell nuclei in the nematode, wherein decreased or unchanged accumulation of the transgene indicates that the test compound is a candidate stress response-inhibiting compound, e.g., a candidate oxidative stress response-inhibiting compound, e.g., a candidate SKN-1-mediated oxidative stress response-inhibiting compound.

In one embodiment, the method further includes a confirmatory step carried out after a candidate compound is identified. The confirmatory step can include providing a second nematode, e.g., a second *C. elegans*, not contacted with the candidate compound, to determine whether the candidate compound decreases the SKN-1-mediated oxidative stress response of the first nematode, e.g., *C. elegans*, relative to the SKN-1-mediated oxidative stress response of the second nematode, e.g., the second *C. elegans*, not contacted with the candidate compound, wherein a candidate compound that decreases SKN-1-mediated oxidative stress response in the first nematode relative to the second nematode is a stress response-inhibiting agent, e.g., an oxidative stress response-inhibiting agent, e.g., an SKN-1-mediated oxidative stress response-inhibiting agent.

In one embodiment, the method further includes determining whether the candidate compound is an inhibitor of SKN-1 by: (a) contacting a SKN-1 polypeptide or SKN-1 DNA with the candidate compound; and (b) detecting interaction of the candidate compound with the SKN-1 polypeptide or SKN-1 DNA, wherein an interaction indicates that the candidate compound is an inhibitor of SKN-1.

In another embodiment, the method includes: (a) providing a cell, e.g., a cultured cell, e.g., a cultured nematode or a cultured mammalian cell, containing a transgene encoding a SKN-1 fusion protein, wherein the transgene comprises: (i) a SKN-1 DNA operably linked to (ii) a reporter gene, e.g., a gene encoding green fluorescent protein, chloramphenicol acetyl transferase, β glucuronidase, or luciferase; (b) contacting the cell, e.g., the cultured cell, e.g., the cultured nematode or cultured mammalian cell, with a test compound; (c) before or during step (b), subjecting the cell, e.g., the cultured cell, e.g., the cultured nematode or cultured mammalian cell, to conditions that activate the SKN-1-mediated oxidative stress response in the absence of the test compound; and (d) determining whether the SKN-1 fusion protein accumulates in the nucleus of the cell, e.g., the cultured cell, e.g., the cultured nematode or cultured mammalian cell, wherein decreased or unchanged accumulation of the transgene indicates that the test compound is a candidate stress response-inhibiting compound, e.g., a candidate oxidative stress response-inhibiting compound, e.g., a candidate SKN-1-mediated oxidative stress response-inhibiting compound.

In one embodiment, the method further includes a confirmatory step carried out after a candidate compound is identified. The confirmatory step can include providing a second cell, e.g., a second cultured cell, e.g., a second cultured nematode cell or second cultured mammalian cell, not contacted with the candidate compound to determine whether the candidate compound decreases the SKN-1-mediated oxidative stress response of the first cell, e.g., the first cultured cell, e.g., the first cultured nematode cell or first cultured mammalian cell, relative to the SKN-1-mediated oxidative stress response of the second cell, e.g., the second cultured cell, e.g., the second cultured nematode cell or second cultured mammalian cell, not contacted with the candidate compound, wherein a candidate compound that decreases SKN-1-mediated oxidative stress response in the first cell relative to the second cell is a stress response-inhibiting agent, e.g., an oxidative stress response-inhibiting agent, e.g., an SKN-1-mediated oxidative stress response-inhibiting agent.

In one embodiment, the method further includes determining whether the candidate compound is an inhibitor of SKN-1 by: (a) contacting a SKN-1 polypeptide or SKN-1 DNA with the candidate compound; and (b) detecting interaction of the candidate compound with the SKN-1 polypeptide or SKN-1

DNA, wherein an interaction indicates that the candidate compound is an inhibitor of SKN-1.

In another aspect, the invention features a method of modulating stress response, e.g., oxidative stress response, e.g., SKN-1-mediated oxidative stress response, by inhibiting GSK-3. In one embodiment, stress response, e.g., oxidative stress response, e.g., SKN-1-mediated oxidative stress response, is modulated by a compound that interacts with GSK-3, e.g., a compound described herein.

In another aspect, the invention features fusion proteins, e.g., SKN-1 fusion proteins, nucleic acids encoding fusion proteins, e.g., SKN-1 fusion proteins, vectors containing nucleic acids encoding fusion proteins, e.g., SKN-1 fusion proteins, and cells, e.g., cultured cells, e.g., cultured nematode or cultured mammalian cells, expressing fusion proteins, e.g., SKN-1 fusion proteins. In one embodiment, the fusion protein, e.g., the SKN-1 fusion protein, includes an SKN-1 polypeptide, or a fragment thereof, e.g., a biologically active fragment thereof, and a heterologous polypeptide, e.g., a reporter polypeptide, e.g., green fluorescent protein, chloramphenicol acetyl transferase, β glucuronidase, or luciferase.

In another aspect, the invention features transgenic nematodes, e.g., transgenic *C. elegans*, expressing a transgene. In one embodiment, one or more cells of the transgenic nematode, e.g., transgenic *C. elegans*, express a transgene, e.g., a transgene that encodes a fusion protein, e.g., a protein described herein fused to a reporter gene described herein, e.g., an skn-1::gfp transgene, a gcs-1::gfp transgene, or a gsk-3::gfp transgene.

In another aspect, the invention features compounds capable of activating an SKN-1-mediated oxidative stress response isolated using the methods described herein (e.g., for isolating SKN-1 mediated oxidative stress response inhibitors or activators). In one embodiment, the compounds, e.g., compounds described herein, interact with GSK-3. In one embodiment, a test compound that interacts with GSK-3, e.g., a test compound described herein, is identified as a candidate compound that can manipulate stress response, e.g., oxidative stress response, e.g., SKN-1-mediated oxidative stress response.

The invention also features the use of a compound identified herein in the manufacture of a medicament for treatment or prevention of a condition described herein. The medicament can be in any form described herein.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF THE DRAWINGS

FIG. 7 illustrates an exemplary regulatory sequence (SEQ ID NO:18) for the glutathione synthetase gene.

FIG. 8 illustrates the sequences of the glutathione synthetase ORF (SEQ ID NO:19) and protein (SEQ ID NO:20).

FIG. 9 illustrates an exemplary regulatory sequence (SEQ ID NO:21) for the NADH quinone oxidoreductase gene.

FIG. 10 illustrates the sequences of the NADH quinone oxidoreductase ORF (SEQ ID NO:22) and protein (SEQ ID NO:23).

FIG. 11 illustrates an exemplary regulatory sequence (SEQ ID NO:24) for the glutathione S-transferase (R03D7.6) gene.

FIG. 12 illustrates the sequences of the glutathione S-transferase (R03D7.6) ORF (SEQ ID NO:25) and protein (SEQ ID NO:26).

FIG. 13 illustrates an exemplary regulatory sequence (SEQ ID NO:27) for the glutathione S-transferase (F35E8.8) gene.

FIG. 14 illustrates the sequences of the glutathione S-transferase (F35E8.8) ORF (SEQ ID NO:28) and protein (SEQ ID NO:29).

FIG. 15 illustrates an exemplary regulatory sequence (SEQ ID NO:30) for the glutathione S-transferase (F11G11.2) gene.

FIG. 16 illustrates the sequences of the glutathione S-transferase (F11G11.2) ORF (SEQ ID NO:31) and protein (SEQ ID NO:32).

FIG. 17 illustrates an exemplary regulatory sequence (SEQ ID NO:33) for the glutathione S-transferase (K08F4.7) gene.

FIG. 18 illustrates the sequences of the glutathione S-transferase (K08F4.7) ORF (SEQ ID NO:34) and protein (SEQ ID NO:35).

FIG. 19 illustrates an exemplary regulatory sequence (SEQ ID NO:36) for the superoxide dismutase-1 (sod-1) gene.

FIG. 20 illustrates the sequences of the superoxide dismutase-1 (sod-1) ORF (SEQ ID NO:37) and protein (SEQ ID NO:38).

FIG. 21 illustrates an exemplary regulatory sequence (SEQ ID NO:39) for the superoxide dismutase-2 (sod-2) gene.

FIG. 22 illustrates the sequences of the superoxide dismutase-2 (sod-2) ORF (SEQ ID NO:40) and protein (SEQ ID NO:41).

FIG. 23 illustrates an exemplary regulatory sequence (SEQ ID NO:42) for the catalase (ctl-1) gene.

FIG. 24 illustrates the sequences of the catalase (ctl-1) ORF (SEQ ID NO:43) and protein (SEQ ID NO:44).

FIG. 25 illustrates an exemplary regulatory sequence (SEQ ID NO:45) for the superoxide dismutase-3 (sod-3) gene.

FIG. 26 illustrates the sequences of the superoxide dismutase-3 (sod-3) ORF (SEQ ID NO:46) and protein (SEQ ID NO:47).

FIG. 27 illustrates an exemplary regulatory sequence (SEQ ID NO:48) for the γ-glutamine cysteine synthase (also known as glutamate-cysteine ligase) heavy chain gene.

FIG. 28 illustrates the sequences of the γ-glutamine cysteine synthase (also known as glutamate-cysteine ligase) heavy chain open reading frame (ORF) (SEQ ID NO:49) and protein (SEQ ID NO:50).

FIG. 29 illustrates the sequences of the T19E7.2c SKN-1 (SEQ ID NO:4), ORF (SEQ ID NO:3) and protein (SEQ ID NO:2).

FIG. 30 illustrates the sequences of the T19E7.2b SKN-1 (SEQ ID NO:8), ORF (SEQ ID NO:6) and protein (SEQ ID NO:7).

FIG. 31 illustrates the sequences of the T19E7.2a SKN-1 (SEQ ID NO:12), ORF (SEQ ID NO:9) and protein (SEQ ID NO:10).

FIG. 32 illustrates the amino acid sequence (SEQ ID NO:13) of human GSK-3 beta.

FIG. 33 illustrates the amino acid sequence (SEQ ID NO:14) of human GSK-3 alpha.

FIG. 34 illustrates the amino acid sequence (SEQ ID NO:15) of mouse GSK-3 beta.

FIG. 35 illustrates the amino acid sequence (SEQ ID NO:16) of mouse GSK-3 alpha.

FIG. 36 illustrates the amino acid sequence (SEQ ID NO:17) of *C. elegans* GSK-3.

DETAILED DESCRIPTION

Figures 1A, 1B, 1C:
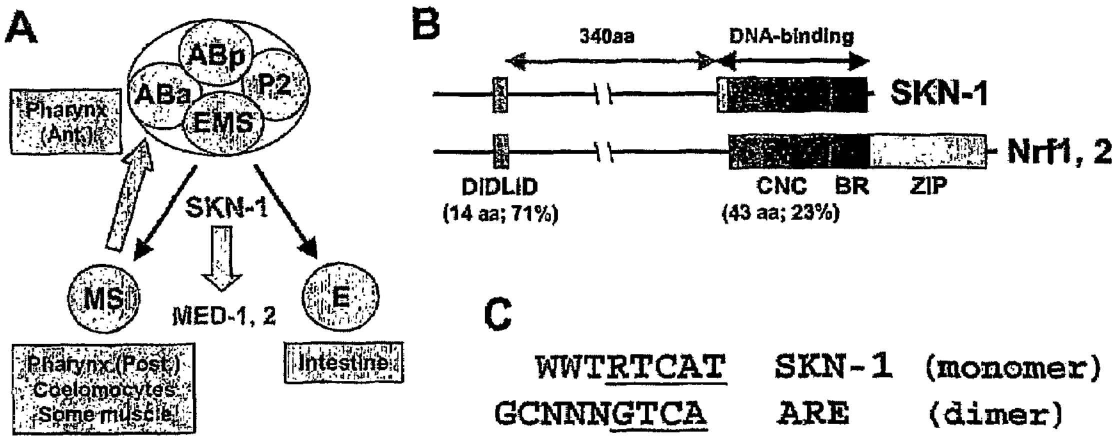
FIGS. 1A-1C: SKN-1 embryonic functions and comparison to Nrf proteins. 1A: Cell fate specification. In four-cell embryos, SKN-1 initiates mesendodermal development by establishing the EMS blastomere fate. The anterior pharynx is specified in ABa descendants by an SKN-1-dependent signal from MS. Anterior is to the left, and ventral at the bottom. 1B: SKN-1 compared to Nrf proteins. The SKN-1 minor groove-binding arm is shown in light green. Percent identity between SKN-1 and mouse Nrf2 regions is indicated. 1C: Consensus sequences for SKN-1 binding and the ARE. The SKN-1 BR recognizes a consensus bZIP half-site (underlined) adjacent to an AT-rich motif (grey) that is specified by the arm (B). Nrf proteins bind to the ARE as obligate heterodimers with Maf or other bZIP. R=G/A; W=T/A.

The present invention relates, in part, to the *C. elegans* SKN-1 gene and protein (a transcription factor), the GSK-3 gene and protein, gcs-1 (encoding γ-glutamine cysteine synthase heavy chain (GCS(h); a target gene of SKN-1) and other oxidative stress resistance genes, e.g., M176.2 (encoding glutathione synthetase); F39B2.3 (encoding NADH quinone oxidoreductase); sod-1, sod-2, and sod-3 (encoding superoxide dismutase); ctl-1 (encoding catalase); and R03D7.6, F35E8.8, F11 G11.2, and K08F4.7 (encoding glutathione S-transferase). The invention includes various therapeutic and screening methods. For example, the genes and/or proteins described herein can be used in screening methods to identify compounds, e.g., compounds capable of modulating (e.g., increasing or decreasing) the expression and/or activity of SKN-1 or the expression and/or activity of GSK-3, and/or capable of modulating the oxidative stress response pathway in nematodes and other animals (e.g., humans). Such compounds can be used as pharmaceutical agents and/or pesticides.

Before further description of the invention, certain terms employed in the specification, examples, and appended claims are, for convenience, collected here.

By "SKN-1-mediated oxidative stress response" is meant an oxidative stress response pathway mediated (i.e., activated) by SKN-1 polypeptides.

The *C. elegans* genome has been sequenced (see, e.g., The *C. elegans* Sequencing Consortium, Science 282, p. 2012-2018, 1998), and is accessible through several known electronic databases (see, e.g., the databases accessible at World Wide Web (www) addresses: wormbase.org (WormBase; see, Harris et al., Nucleic Acids Research 31:133-137 (2003), and Stein et al., Nucleic Acids Research 29:82-86 (2001)); ncbi.nlm.nih.gov; and wormbase.sanger.ac.uk). "SKN-1 DNA" or "SKN-1 gene" refers to nucleic acid sequences that include, e.g., the nucleic sequence set forth in FIG. 29 (or the unspliced version thereof) (set forth in the WormBase database as T19E7.2c) and/or FIG. 31 or 30 (or the unspliced versions thereof) (set forth in the WormBase database as T19E7.2a, and T19E7.2b, respectively), homologs thereof, or fragments thereof that encodes SKN-1 polypeptide fragment capable of binding a SKN-1 protein binding site within a promoter of a target gene, e.g., a *C. elegans* Phase II detoxification gene. An example of such a fragment is a fragment that encodes the C-terminal 85 amino acid residues (SEQ ID NO:1) of the SKN-1 polypeptide set forth in FIG. 29 (referred to herein as a "SKN-1 Domain"). By "SKN-1 polypeptide" is meant an amino acid sequence that includes an amino acid sequence set forth in FIGS. 29, 30 and/or 31, or fragments thereof (e.g., the C-terminal 85 amino acid residues (SEQ ID NO:1) of the SKN-1 polypeptide set forth in FIG. 29 (a "SKN-1 Domain), or amino acids 381-403 (SEQ ID NO:5) set forth in FIG. 29, or amino acids 473-495 (SEQ ID NO:11) set forth in FIG. 31). By "SKN-1 RNA" is meant messenger RNA transcribed from a SKN-1 DNA sequence.

"GSK-3 DNA" or "GSK-3 gene" refers to nucleic acid sequences encoding GSK-3 (such sequences are known in the art), homologs thereof, or fragments thereof, that encode GSK-3 polypeptide fragments capable of binding a SKN-1 protein. By "GSK-3 polypeptide" is meant an amino acid sequence that includes an amino acid sequence set forth in FIGS. 32, 33, 34, 35 and/or 36, or fragments thereof. By "GSK-3 RNA" is meant messenger RNA transcribed from a GSK-3 DNA sequence.

As used herein, an "oxidative stress resistance gene" is a gene involved in the oxidative stress response in *C. elegans*, and homologs thereof. For example, oxidative stress resistance genes include those demonstrated herein to be targets of the SKN-1 polypeptide, e.g., those encoding γ-glutamine cysteine synthase heavy chain (GCS(h)) (gcs-1, set forth in WormBase as F37B12.2); glutathione synthetase (set forth in WormBase as M176.2); NADH quinone oxidoreductase (set forth in WormBase as F39B2.3); superoxide dismutase (sod-1, sod-2, and sod-3; set forth in WormBase as C15F1.7; F10D11.1; C08A9.1, respectively); catalase (ctl-1; set forth in WormBase as Y54G11A.6; and several forms of glutathione S-transferase (set forth in WormBase as R03D7.6, F35E8.8, F11G11.2, and K08F4.7), among others.

The sequence of the γ-glutamine cysteine synthase (also known as glutamate-cysteine ligase) heavy chain open reading frame (ORF) and protein are set forth in FIG. 28, and an exemplary regulatory sequence is set forth in FIG. 27. The sequence of the glutathione synthetase ORF and protein are set forth in FIG. 8, and an exemplary regulatory sequence is set forth in FIG. 7. The sequence of the NADH quinone oxidoreductase ORF and protein are set forth in FIG. 10, and an exemplary regulatory sequence is set forth in FIG. 9. The sequence of one glutathione S-transferase (R03D7.6) ORF and protein are set forth in FIG. 12, and an exemplary regulatory sequence is set forth in FIG. 11. The sequence of another glutathione S-transferase (F35E8.8) ORF and protein are set forth in FIG. 14, and an exemplary regulatory sequence is set forth in FIG. 13. The sequence of a third glutathione S-transferase (F11G101.2) ORF and protein are set forth in FIG. 16, and an exemplary regulatory sequence is set forth in FIG. 15. The sequence of a fourth glutathione S-transferase (K08F4.7) ORF and protein are set forth in FIG. 18, and an exemplary regulatory sequence is set forth in FIG. 17. The sequence of the superoxide dismutase-1 (sod-1) ORF and protein are set forth in FIG. 20, and an exemplary regulatory sequence is set forth in FIG. 19. The sequence of the superoxide dismutase-2 (sod-2) ORF and protein are set forth in FIG. 22 and an exemplary regulatory sequence is set forth in FIG. 21. The sequence of the superoxide dismutase-3 (sod-3) ORF and protein are set forth in FIG. 26, and an exemplary regulatory sequence is set forth in FIG. 25. The sequence of the catalase (ctl-1) ORF and protein are set forth in FIG. 24 and an exemplary regulatory sequence is set forth in FIG. 23. Predicted SKN-1 binding sites upstream of the genes described above are set forth in Table 1.

A "substantially pure" preparation is a preparation that is at least 60% by weight (dry weight) compound of interest. For example, a "substantially pure" preparation can be a preparation that is at least 60% by weight of SKN-1 polypeptide, GSK-3 polypeptide, or a candidate compound or agent described herein. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

The term "purified DNA" means DNA that is not immediately contiguous with both of the coding sequences with which it is immediately contiguous (one on the 5' end and one on the 3' end) in the naturally-occurring genome of the organism from which it is derived. The term, therefore, includes, for example, a recombinant DNA that is incorporated into a vector; into an autonomously replicating plasmid or virus; or into the genomic DNA of a prokaryote or eukaryote, or that exists as a separate molecule (e.g., a cDNA or a genomic DNA fragment produced by PCR or restriction endonuclease treatment) independent of other sequences. It also includes a recombinant DNA that is part of a hybrid gene encoding additional polypeptide sequence.

A "substantially identical" nucleic acid means a nucleic acid sequence that encodes a polypeptide differing only by conservative amino acid substitutions or by one or more non-conservative substitutions, deletions, or insertions located at positions of the amino acid sequence that do not destroy the function of the polypeptide.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue can be replaced with another amino acid residue from the same side chain family.

The terms "activate," "induce," "inhibit," "elevate," "increase," "decrease," or the like, denote quantitative differences between two states. A quantitative difference can be, e.g., a statistically significant difference, between the two states.

Homology can be measured using sequence analysis software (e.g., Sequence Analysis Software Package of the Genetics Computer Group, University of Wisconsin Biotechnology Center, 1710 University Avenue, Madison, Wis. 53705, BLAST, or PILEUP/PRETTYBOX programs). Such software matches similar sequences by assigning degrees of homology to various substitutions, deletions, and other modifications.

By "purified antibody" is meant antibody that is at least 60%, by weight, free from the proteins and naturally-occurring organic molecules with which it is naturally associated. Preferably, the preparation is at least 75%, more preferably at least 90%, and most preferably at least 99%, by weight, antibody.

The term "longevity" refers to the rate of senescence and/or life-span. The term "immunological methods" refers to any assay involving antibody-based detection techniques including, without limitation, Western blotting, immunoprecipitation, and direct and competitive ELISA and RIA techniques. "Means for detecting" refers to any one or a series of components that sufficiently indicate a detection event of interest. Such means involve at least one label that may be assayed or observed, including, without limitation, radioactive, fluorescent, and chemiluminescent labels.

By "hybridization techniques" is meant any detection assay involving specific interactions (based on complementarity) between nucleic acid strands. Such interactions include, e.g., DNA-DNA, RNA-RNA, and DNA-RNA interactions. Such hybridization techniques may, if desired, include a PCR amplification step.

The term "modulatory compound", as used herein, refers to any compound capable of either increasing or decreasing SKN-1 expression (i.e., at the level of transcription or translation), SKN-1 polypeptide activity, GSK-3 expression, GSK-3 polypeptide activity, or activating or inhibiting a stress response pathway, e.g., an oxidative stress response pathway, e.g., a SKN-1-mediated oxidative stress response pathway.

The terms "effective amount" and "effective to treat," as used herein, refer to an amount or concentration of a pharmaceutical composition described herein utilized for a period of time that is effective within the context of its administration for causing an intended effect or physiological outcome. The period of time includes acute or chronic administration and periodic or continuous administration.

The term "patient" refers to an animal, human or non-human, to whom treatment according to the methods of the present invention is provided. Veterinary applications are clearly anticipated by the present invention. The term includes, but is not limited to, birds, reptiles, amphibians, and mammals, e.g., humans, other primates, pigs, rodents (such as mice and rats), rabbits, guinea pigs, hamsters, cows, horses, cats, dogs, sheep and goats. Preferred subjects are humans, farm animals, and domestic pets such as cats and dogs. The terms "treat" and "treatment" are used herein to denote the use of a protein, agent, or composition described herein to delay the onset of, to inhibit, to alleviate the effects of, or to prolong the life of a patient.

Screening Methods

In vertebrates, the Nrf pathway has been shown to be critical for oxidative stress resistance, and to be involved in numerous disease states including diabetes, HIV infection, and atherosclerosis, as well as in drug detoxification and cancer chemoprevention. The vertebrate Nrf pathway responds to natural antioxidants found in plants, which produce these compounds for protection against errors in photosynthesis. The present invention is based in part on the discovery that, in addition to its role in development, SKN-1 plays a role in the *C. elegans* counterpart to the vertebrate Nrf pathway. Like the Nrf pathway, the *C. elegans* pathway mediated by SKN-1 responds to the well-studied natural antioxidant sulforaphane.

GSK-3 (Glycogen synthase kinase 3) was initially described as a key enzyme involved in glycogen metabolism, but is now known to regulate a diverse array of cell functions. See, e.g., Cohen et al. (2001) *Mol. Cell. Biol.* 2:769-776.

The invention provides in vivo and in vitro screening methods for identifying compounds, e.g., small organic or inorganic molecules (M.W. less than 1,000 Da), oligopeptides, oligonucleotides, or carbohydrates capable of activating or inhibiting the SKN-1-mediated oxidative stress response.

The screening methods are useful, for example, for isolating novel antioxidants (e.g., compounds that activate a stress response pathway, e.g., an oxidative stress response pathway, e.g., the SKN-1-mediated oxidative stress response pathway) or compounds that can be used as pesticides (e.g., compounds that inhibit a stress response pathway, e.g., an oxidative stress response pathway, e.g., the SKN-1-mediated oxidative stress response pathway). Skilled practitioners will also appreciate that the screening methods described herein can be used, for example, to identify or isolate other genes and/or proteins involved in a stress response pathway, e.g., an oxidative stress pathway, e.g., the SKN-1-mediated oxidative stress response pathway, which can themselves be used as pharmaceutical agents or as potential targets for drug discovery.

In Vivo Screening Methods

In one embodiment, the present invention provides methods for determining whether a test compound is a candidate stress response-activating compound, e.g., a candidate oxidative stress response-activating compound, e.g., a candidate SKN-1-mediated oxidative stress response-activating compound. One method includes providing a nematode, isolated nematode cell, or isolated mammalian cell capable of expressing SKN-1 and containing at least one (i.e., one or more) transgene comprising an oxidative stress resistance gene promoter operably linked to a reporter gene; and contacting the nematode, isolated nematode cell, or isolated mammalian cell, with the test compound, wherein an increase in expression of the transgene following contact of the nematode, isolated nematode cell, or isolated mammalian cell, with the test compound indicates that the test compound is a candidate stress response-activating compound, e.g., a candidate oxidative stress response-activating compound, e.g., a candidate SKN-1-mediated oxidative stress response-activating compound.

A similar method can be carried out to determine whether a test compound is a candidate stress response-inhibiting compound, e.g., a candidate oxidative stress response-inhibiting compound, e.g., a candidate SKN-1-mediated oxidative stress response-inhibiting compound. The method includes providing a nematode, isolated nematode cell, or isolated mammalian cell capable of expressing SKN-1 and containing at least one (i.e., one or more) transgene comprising an oxidative stress resistance gene promoter operably linked to a reporter gene; contacting the nematode, isolated nematode cell, or isolated mammalian cell, with the test compound; and subjecting the nematode, isolated nematode cell, or isolated mammalian cell to conditions that activate the SKN-1-mediated oxidative stress response in the absence of the test compound, wherein a decrease or lack of increase in expression of the transgene following the subjecting step indicates that the test compound is a candidate stress response-inhibiting compound, e.g., a candidate oxidative stress response-inhibiting compound, e.g., a candidate SKN-1-mediated oxidative stress response-inhibiting compound.

In still another method, a nematode, isolated nematode cell, or isolated mammalian cell capable of expressing a SKN-1 fusion protein is utilized to determine whether a test compound is a candidate stress response-activating compound, e.g., a candidate oxidative stress response-activating compound, e.g., a candidate SKN-1-mediated oxidative stress response-activating compound. The method includes providing a nematode, isolated nematode cell, or isolated mammalian cell containing a transgene that includes SKN-1 DNA operably linked to a reporter gene; contacting the nematode, isolated nematode cell, or isolated mammalian cell, with the test compound; and determining whether the SKN-1 fusion protein accumulates in nuclei in the nematode, isolated nematode cell, or isolated mammalian cell. Increased accumulation (e.g., above control levels), indicates that the test compound is a candidate stress response-activating compound, e.g., a candidate oxidative stress response-activating compound, e.g., a candidate SKN-1-mediated oxidative stress response-activating compound.

A similar method can be carried out to determine whether a test compound is a candidate stress response-inhibiting compound, e.g., a candidate oxidative stress response-inhibiting compound, e.g., a candidate SKN-1-mediated oxidative stress response-inhibiting compound. The method includes providing a nematode, isolated nematode cell, or isolated mammalian cell containing a transgene that includes SKN-1 DNA operably linked to a reporter gene; contacting the nematode, isolated nematode cell, or isolated mammalian cell, with the test compound; subjecting the nematode, isolated nematode cell, or isolated mammalian cell to conditions that activate the SKN-1-mediated oxidative stress response in the absence of the test compound; and determining whether the SKN-1 fusion protein accumulates in nuclei in the nematode, isolated nematode cell, or isolated mammalian cell. Decreased or no increase in accumulation (e.g., as compared to control levels), indicates that the test compound is a candidate stress response-inhibiting compound, e.g., a candidate oxidative stress response-inhibiting compound, e.g., a candidate SKN-1-mediated oxidative stress response-inhibiting compound.

A "test compound" can be any chemical compound, for example, a macromolecule (e.g., a polypeptide, a protein complex, or a nucleic acid) or a small molecule (e.g., an amino acid, a nucleotide, an organic or inorganic compound). The test compound can have a formula weight of less than about 10,000 grams per mole, less than 5,000 grams per mole, less than 1,000 grams per mole, or less than about 500 grams per mole. The test compound can be naturally occurring (e.g., an herb or a natural product), synthetic, or can include both natural and synthetic components. Examples of small molecules include peptides, peptidomimetics (e.g., peptoids), amino acids, amino acid analogs, polynucleotides, polynucleotide analogs, nucleotides, nucleotide analogs, and organic or inorganic compounds, e.g., heteroorganic or organometallic compounds.

Test compounds can be screened individually or in parallel. An example of parallel screening is a high throughput drug screen of large libraries of chemicals. Such libraries of test compounds can be generated or purchased, e.g., from Chembridge Corp., San Diego, Calif. Libraries can be designed to cover a diverse range of compounds. For example, a library can include 500, 1000, 10,000, 50,000, or 100,000 or more unique compounds. Alternatively, prior experimentation and anecdotal evidence can suggest a class or category of compounds of enhanced potential. A library can be designed and synthesized to cover such a class of chemicals.

Examples of methods for the synthesis of molecular libraries can be found in, for example, DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

If a nematode is to be used in the present methods, it can be of any genus and species, e.g., any animal, plant, or insect parasitic nematode, or any free-living terrestrial or aquatic (i.e., marine or freshwater) nematode, that is capable of harboring one or more of the constructs described herein. An example of a particularly useful nematode is *C. elegans*. Likewise, if a cultured nematode cell (e.g., a cultured nematode intestinal cell) is to be used, it can be isolated from any genus and species of nematode. Further, if a mammalian cell is to be used, it can be any mammalian cell, e.g., 3T3, HeLa, and/or HD3 erythroblasts, among others.

The oxidative stress resistance gene promoter can be from a gene described herein as, or identified using a method described herein, to be a target of a SKN-1 polypeptide. As used herein, a "promoter" is a minimal sequence sufficient to direct transcription located in the 5' region of the native gene. For example, the promoter can be from a gene encoding γ-glutamine cysteine synthase heavy chain (GCS(h)) (gcs-1, sequences for which are set forth in WormBase as F37B12.2); glutathione synthetase (sequences for which are set forth in WormBase as M176.2); NADH quinone oxidoreductase (set forth in WormBase as F39B2.3); superoxide dismutase (sod-1, sod-2, and sod-3; sequences for which are set forth in WormBase as C15F1.7; F10D11.1; C08A9.1, respectively); catalase (ctl-1; sequences for which are set forth in WormBase as Y54G11A.6); and several forms of glutathione S-transferase (sequences for which are set forth in WormBase as R03D7.6, F35E8.8, F11G11.2, and K08F4.7), among others. In certain embodiments of the present invention, a SKN-1 promoter is included in a transgene (sequences for which are set forth in the WormBase database as T19E7.2a, T19E7.2b, and T19E7.2c).

The present invention contemplates that promoters can be modified to provide preferential (i.e., organ- and/or tissue-specific) expression (and/or repression) of a construct. Examples of such modifications are described in detail in Example 1 (below). There, gcs-1 promoter deletions were constructed using PCR. Predicted SKN-1 polypeptide binding sites (underlined) were altered as follows: Site 1—608 <u>GATGACAAT</u> to <u>CTGCAGAAT</u>. Site 2—317 <u>GATGACTTA</u> to <u>CTGCAGTTA</u>, and Site 3—121 <u>TTTATCATC</u> to <u>TTTCTGCAG</u>. Expression patterns of the construct changed depending upon the deletions made. For example, the gcsΔ 2 mutation eliminated pharyngeal GCS-1::GFP expression, but allowed near-wild type levels of ASI and intestinal expression. Concurrent ablation of SKN-1 binding site 3 (gcsΔ 2,mut3) eliminated transgene expression in all tissues. Skilled practitioners will appreciate that similar procedures could be used to cause preferential expression of other constructs.

The "reporter gene" can be any sequence the expression of which can be detected or measured, other than the coding sequence to which the promoter naturally is operably linked. Typically, the reporter gene is heterologous to the nematode, isolated nematode cell, or isolated mammalian cell in which promoter activity is measured. Examples of reporter genes include, without limitation, genes that encode green fluorescent protein (or any other fluorescent marker), chloramphenicol acetyl transferase (cat), β-glucuronidase (gus), β-Galactosidase (lacZ), luciferase, and the like. Reporter gene expression can be measured by any of a number of conventional methods, and the optimal method will depend upon factors such as the nature and function of the reporter gene. In general, suitable assays of reporter gene expression include methods such as (i) assaying the function of a product of the reporter gene (e.g., measuring an enzymatic reaction catalyzed by a product of the reporter gene); (ii) measuring the level of protein expressed from the reporter gene (e.g., by SDS-PAGE or in an immunoassay using antibodies (e.g., polyclonal or monoclonal antibodies) that specifically bind to the product of the reporter gene); and (iii) measuring the level of mRNA transcribed from the reporter gene. Included within the invention are assays that permit high throughput screening of test compounds.

Reporter genes, and methods for measuring their expression, are well known to those of ordinary skill in the art. Methods for making the transgenes and their incorporation into the genomes of organisms, e.g., nematodes, or cells, e.g., cultured nematode or mammalian cells, are also well known in the art. Example 1 (below) describes in detail how to make gcs-1::gfp and skn-1::gfp transgenes, how to incorporate such transgenes into the genome of *C. elegans*, and how to measure expression of the transgenes (a microscopy-based screen is performed in that Example). Skilled practitioners will appreciate that similar protocols can be used to create other transgenes described herein, and to incorporate those transgenes into other types of nematodes and cultured cells. The present invention contemplates that more than one type of transgene can be inserted into the genome of a nematode or cell.

Compounds capable of activating a stress response, e.g., an oxidative stress response, e.g., the SKN-1-mediated oxidative stress response, in an initial screen discussed above can be considered candidate stress response-activating compounds, e.g., candidate oxidative stress response-activating compounds, e.g., candidate SKN-1-mediated oxidative stress response-activating compounds. Such candidate compounds can be subjected to a confirmatory step, e.g., to determine whether the candidate compound increases the overall oxidative stress resistance of a nematode or cultured cell (e.g., a mammalian cell). Methods for evaluating the oxidative stress resistance of a cell or organism (e.g., relative to controls) are well known in the art, and include, for example, subjecting an organism or cell to conditions of oxidative stress (e.g., using known compounds or by increasing the temperature of the culture environment) and measuring overall survival rate. Alternatively or in addition, the confirmatory step can involve determining whether the candidate compound is capable of increasing expression of at least one gene involved in the vertebrate Nrf oxidative stress response pathway, using transgenes (similar to those described herein) or any other method known in the art for measuring increased expression (e.g., Western blotting). Candidate activating compounds that increase stress resistance, e.g., oxidative stress resistance, e.g., SKN-1-mediated oxidative stress resistance, in a nematode, cultured nematode cell, or mammalian cell, or that are capable of increasing expression of at least one gene involved in the vertebrate Nrf oxidative stress response pathway, can be considered stress response-activating agents, e.g., oxidative stress response-activating agents, e.g., SKN-1-mediated oxidative stress response-activating agents.

Alternatively or in addition, a different confirmatory step can be carried out. This step involves providing a nematode not capable of expressing a SKN-1 polypeptide (i.e., a skn-1 mutant) containing at least one transgene that includes an oxidative stress resistance gene promoter operably linked to a reporter gene; and contacting the nematode with the test compound. If the transgene displays no increase in expression, the candidate compound specifically activates the SKN-1-mediated oxidative stress response, and can be considered an oxidative stress response-activating agent.

Compounds capable of inhibiting a stress response, e.g., an oxidative stress response, e.g., the SKN-1-mediated oxidative stress response, in an initial screen discussed above can be considered candidate inhibiting compounds, i.e., candidate stress response-inhibiting compounds, e.g., candidate oxidative stress response-inhibiting compounds, e.g., candidate SKN-1-mediated oxidative stress response-inhibiting compounds. Such candidate inhibitory compounds can also be subjected to a confirmatory step, e.g., to determine whether the candidate inhibitory compound decreases the overall oxidative stress resistance of a nematode or cultured cell (e.g., a mammalian cell). Alternatively or in addition, the confirmatory step can involve determining whether the candidate compound is capable of decreasing (or preventing increased expression under conditions of oxidative stress) expression of at least one gene involved in the vertebrate Nrf oxidative stress response pathway (or an oxidative stress resistance gene not utilized in the initial screen). Such screens can be carried out using transgenes similar to those described herein or any other method known in the art for measuring increased or decreased expression (e.g., Western blotting). Candidate inhibiting compounds that decrease oxidative stress resistance in a nematode, cultured nematode cell, or mammalian cell, or prevent (or decrease) increased expression of another oxidative stress resistance gene under conditions of oxidative stress, can be considered an oxidative stress response-inhibiting agent.

Some screens of the present invention require subjecting the nematode or cell to conditions that activate the SKN-1-mediated oxidative stress response in the absence of a test compound. Such conditions include exposing the nematode or cell to a known antioxidant, e.g., sulforaphane. Other conditions include, e.g., exposure to the herbicide paraquat (methyl viologen), heat, $CdCl_2$, arsenite, $H_2O_2$, diamide, and/or sodium azide.

In Vitro Screening Methods

The invention also provides in vitro methods for determining whether a test compound is a candidate stress response-inhibiting compound, e.g., a candidate oxidative stress response-inhibiting compound, e.g., a candidate SKN-1-mediated oxidative stress response-inhibiting compound. For example, the method can include contacting a SKN-1 polypeptide, or a fragment thereof (e.g., a SKN-1 Domain), a SKN-1 DNA, a GSK-3 polypeptide, or a fragment thereof, or a GSK-3 DNA with a test compound; and detecting interaction of the test compound with the SKN-1 or GSK-3 polypeptide (or fragment thereof) or with the SKN-1 or GSK-3 DNA. An interaction (e.g., direct or indirect binding) with SKN-1 polypeptide or DNA indicates that the test compound is a candidate stress response-inhibiting compound, e.g., a candidate oxidative stress response-inhibiting compound, e.g., a candidate SKN-1-mediated oxidative stress response-inhibiting compound. An interaction (e.g., direct or indirect binding) with GSK-3 polypeptide or DNA indicates that the test compound is a candidate stress response-activating compound, e.g., a candidate oxidative stress response-activating compound, e.g., a candidate SKN-1-mediated oxidative stress response-activating compound.

Another method takes advantage of interactions between SKN-1 polypeptides and oxidative stress resistance genes that are targets of SKN-1 polypeptides. The method includes providing a polypeptide that includes a SKN-1 polypeptide (or fragment thereof that is capable of interacting (i.e., binding) with an oxidative stress resistance gene, e.g., a SKN-1 Domain), and an oxidative stress resistance gene. The oxidative stress resistance gene can be a gene identified herein as being a target for SKN-1 polypeptides, e.g., genes encoding γ-glutamine cysteine synthase heavy chain, glutathione synthetase, NADH quinone oxidoreductase, superoxide dismutase, catalase, or glutathione S-transferase. Alternatively, a nucleic acid sequence that includes a SKN-1 polypeptide-binding fragment of the oxidative stress resistance gene can be provided. Examples of SKN-1 polypeptide binding fragments for a number of oxidative stress resistance genes are provided in Table 1. The method further includes contacting the polypeptide comprising the SKN-1 polypeptide (or fragment thereof) and a nucleotide sequence comprising an oxidative stress resistance gene (or SKN-1 polypeptide-binding fragment thereof) with a test compound; and determining whether the SKN-1 polypeptide (or fragment thereof) and the oxidative stress resistance gene (or SKN-1 polypeptide-binding fragment thereof) interact (i.e., bind) in the presence of the test compound. If no or decreased interaction is evident, the test compound can be considered a candidate SKN-1-mediated oxidative stress response-inhibiting compound.

As in the in vivo screening methods, compounds isolated using the in vitro methods can be subjected to any confirmatory step herein described herein. Skilled practitioners will appreciate that in any screening method described herein, homologues of SKN-1 or GSK-3 (e.g., genes or polypeptides) can be substituted for the SKN-1 or GSK-3 DNA or polypeptides. Where such substitutions are made, the screens can be carried out essentially as described herein.

Medicinal Chemistry

Once a compound (or agent) of interest has been identified, standard principles of medicinal chemistry can be used to produce derivatives of the compound. Derivatives can be screened for improved pharmacological properties, for example, efficacy, pharmaco-kinetics, stability, solubility, and clearance. The moieties responsible for a compound's activity in the assays described above can be delineated by examination of structure-activity relationships (SAR) as is commonly practiced in the art. A person of ordinary skill in pharmaceutical chemistry can modify moieties on a lead compound and measure the effects of the modification on the efficacy of the compound to thereby produce derivatives with increased potency. For an example, see Nagarajan et al. (1988) *J. Antibiot.* 41: 1430-8. Furthermore, if the biochemical target of the compound (or agent) is known or determined, the structure of the target and the compound can inform the design and optimization of derivatives. Molecular modeling software is commercially available (e.g., Molecular Simulations, Inc.) for this purpose.

Isolated Compounds

Skilled practitioners will appreciate that compounds isolated using the screens described herein can be used to treat a number of conditions or disorders.

Oxidative stress contributes to human pathologies that include diabetes, atherosclerosis, neurodegenerative diseases, reperfusion injury, and HIV infection (see, e.g., Finkel et al., Nature 408: 239-247 (2000). The ROS defenses mobilized by human Nrf proteins are thought to be beneficial in these diverse disease states. This gene activation pathway is also important for drug detoxification, and, therefore, for chemotherapeutic agent tolerance, and it may provide a widely applicable means of cancer prevention (see, e.g., Chan et al. Proc Natl Acad Sci U.S.A 98: 4611-6. (2001); Hayes et al., Cancer Lett 174: 103-113 (2001); and Wolf *Proc Natl Acad Sci U.S.A* 98: 2941-2943 (2001)). For example, dietary consumption of chemoprotective antioxidants acts through Nrf2 to inhibit chemical carcinogenesis in mice, and decreases the risk of gastrointestinal and lung tumors in humans (see, e.g., Ramos-Gomez et al. Proc Natl Acad Sci U.S.A 98: 3410-3415 (2001); Fahey et al. Proc Natl Acad Sci U.S.A 99: 7610-7615 (2002); and Thimmulappa et al. Cancer Res 62: 5196-5203 (2002)).

Accordingly, candidate stress response-activating compounds, e.g., candidate oxidative response-activating compounds, e.g., candidate SKN-1-mediated oxidative stress response-activating compounds, shown to increase the oxidative stress resistance of mammalian cells (oxidative stress response-activating agents) can be used as novel antioxidants.

Such antioxidants could be used to treat a number of conditions including, but not limited to, aging, cancer (e.g., wherein such an agent can be used in chemoprevention), arteriosclerosis, the effects of diabetes (e.g., the neuropathy and vascular complications associated therewith, islet cell destruction, and detrimental insulin responses), neurodegenerative diseases (e.g., by increasing neuronal oxidative stress resistance and, therefore, survival), reperfusion injury (e.g., injury arising from oxidative stress caused by hypotension, myocardial infarction, and/or stroke); the effects of sleep apnea (e.g., vascular injury arising from the cycle of hypoxia/reoxygenation); viral infection (e.g., human immunodeficiency virus infection); bacterial infections (e.g., in the gut); and toxicity (e.g., drug toxicity (e.g., arising from chemotherapy), heavy metal toxicity, and hepatic toxicity).

Inhibitors are also useful in certain clinical settings. For example, candidate stress response-inhibiting compounds, e.g., candidate oxidative stress response-inhibiting compounds, e.g., candidate SKN-1-mediated oxidative stress response-inhibiting compounds, shown to reduce the oxidative stress resistance of mammalian cells (oxidative stress response-inhibiting agents) can be used to eliminate undesirable cells in an animal, e.g., tumor cells in a human. Further, in certain cancer cells, the oxidative stress response pathway is up-regulated, conferring growth advantages. An inhibitor can be used as a component of a chemotherapeutic regimen to prevent such up-regulation. As still another example, reactive oxygen species (ROS) production plays a detrimental role in certain inflammatory responses, which can be prevented or decreased using an inhibitor described herein.

Modulation of the SKN-1-Mediated Oxidative Stress Response

The invention provides methods for modulating the SKN-1-mediated oxidative stress response that fall into two basic categories: inhibiting (e.g., limiting or reducing) a stress response, e.g., an oxidative stress response, e.g., the SKN-1-mediated oxidative stress response, and activating, e.g., supplementing or providing oxidative stress response activity where there is insufficient or no activity. Whether the SKN-1 mediated oxidative stress response is inhibited or increased depends on the intended application.

Inhibition of the Response by SKN-1 Inhibitors

In some embodiments, the invention provides for inhibiting the SKN-1-mediated oxidative stress response. Agents that inhibit can be used as, e.g., novel pesticides to control insects or nematodes (e.g., pathogenic nematodes). Agents that inhibit the SKN-1-mediated oxidative stress response are useful to inhibit nematode reproduction, decrease nematode lifespan, and increase nematode sensitivity to oxidative stresses (thereby making the nematode easier to eradicate, e.g., using known pesticides). Such agents are also useful for inhibiting SKN-1 activation of the oxidative stress response in a laboratory/research setting in order to identify other genes and/or proteins involved in this oxidative stress response pathway.

For example, an antisense nucleic acid effective to inhibit expression of an endogenous SKN-1 gene can be utilized. The antisense nucleic acid can include a nucleotide sequence complementary to an entire SKN-1 RNA or only a portion of the RNA. On one hand, the antisense nucleic acid needs to be long enough to hybridize effectively with the SKN-1 RNA. Therefore, the minimum length is approximately 10, 11, 12, 13, 14, or 15 nucleotides. On the other hand, as length increases beyond about 150 nucleotides, effectiveness at inhibiting translation increases only marginally, while difficulty in introducing the antisense nucleic acid into target cells may increase significantly. In view of these considerations, a preferred length for the antisense nucleic acid is from about 15 to about 150 nucleotides, e.g., 20, 25, 30, 35, 40, 45, 50, 60, 70, or 80 nucleotides. The antisense nucleic acid can be complementary to a coding region of SKN-1 mRNA or a 5' or 3' non-coding region of a SKN-1 mRNA (or both). One approach is to design the antisense nucleic acid to be complementary to a region on both sides of the translation start site of the SKN-1 mRNA.

The antisense nucleic acid can be chemically synthesized, e.g., using a commercial nucleic acid synthesizer according to the vendor's instructions. Alternatively, the antisense nucleic acids can be produced using recombinant DNA techniques. An antisense nucleic acid can incorporate only naturally occurring nucleotides. Alternatively, it can incorporate variously modified nucleotides or nucleotide analogs to increase its in vivo half-life or to increase the stability of the duplex formed between the antisense molecule and its target RNA. Examples of nucleotide analogs include phosphorothioate derivatives and acridine-substituted nucleotides. Given the description of the targets and sequences, the design and production of suitable antisense molecules is within ordinary skill in the art. For guidance concerning antisense nucleic acids, see, e.g., Goodchild, "Inhibition of Gene Expression by Oligonucleotides," in *Topics in Molecular and Structural Biology, Vol.* 12*: Oligodeoxynucleotides* (Cohen, ed.), MacNillan Press, London, pp. 53-77.

Delivery of antisense oligonucleotides can be accomplished by any method known to those of skill in the art. For example, delivery of antisense oligonucleotides for cell culture and/or ex vivo work can be performed by standard methods such as the liposome method or simply by addition of membrane-permeable oligonucleotides. To resist nuclease degradation, chemical modifications such as phosphorothioate backbones can be incorporated into the molecule.

Delivery of antisense oligonucleotides for in vivo applications can be accomplished, for example, via local injection of the antisense oligonucleotides at a selected site. This method has previously been demonstrated for psoriasis growth inhibition and for cytomegalovirus inhibition. See, for example, Wraight et al., (2001). *Pharmacol Ther*. April; 90(1):89-104; Anderson, et al., (1996) *Antimicrob Agents Chemother* 40: 2004-2011; and Crooke et al., *J Pharmacol Exp Ther* 277: 923-937.

Similarly, the present invention anticipates that RNA interference (RNAi) techniques could be used to inhibit the SKN-1-mediated oxidative stress response, in addition or as an alternative to, the use of antisense techniques. For example, small interfering RNA (siRNA) duplexes directed against SKN-1, or any oxidative stress response gene target of SKN-1, could be synthesized and used to prevent expression of the encoded protein(s). Skilled practitioners will also appreciate that RNAi techniques could be used in screens to identify other genes and/or proteins that modulate the SKN-1 oxidative stress response pathway. For example, these techniques could be used in a screen for genes that when inhibited allowed constitutive activation of the gcs-1::gfp transgene, or that prevented the gcs-1::gfp transgene from being activated by oxidative stress or antioxidants.

As another example, SKN-1 polypeptide activity can be inhibited using a SKN-1 polypeptide binding molecule such as an antibody, e.g., an anti-SKN-1 polypeptide antibody, or a SKN-1 polypeptide-binding fragment thereof. The anti-SKN-1 polypeptide antibody can be a polyclonal or a monoclonal antibody. Alternatively or in addition, the antibody can be produced recombinantly, e.g., produced by phage display or by combinatorial methods as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982.

As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917). Each VH and VL is composed of three CDR's and four FRs, arranged from amino-terminus to carboxy-terminus in the following order: FR1, CDR1, FR2, CDR2, FR3, CDR3, FR4.

An anti-SKN-1 polypeptide antibody can further include a heavy and light chain constant region, to thereby form a heavy and light immunoglobulin chain, respectively. The antibody can be a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2, and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

A "SKN-1 polypeptide-binding fragment" of an antibody refers to one or more fragments of a full-length antibody that retain the ability to specifically bind to SKN-1 polypeptide or a portion thereof. "Specifically binds" means that an antibody or ligand binds to a particular target to the substantial exclusion of other substances. Examples of SKN-1 polypeptide binding fragments of an anti-SKN-1 polypeptide antibody include, but are not limited to: (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are encoded by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "SKN-1 polypeptide-binding fragment" of an antibody. These antibody fragments can be obtained using conventional techniques known to those with skill in the art.

The anti-SKN-1 polypeptide antibody can be a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel, donkey, porcine, or fowl antibody.

An anti-SKN-1 polypeptide antibody can be one in which the variable region, or a portion thereof, e.g., the CDRs, are generated in a non-human organism, e.g., a rat or mouse. The anti-SKN-1 polypeptide antibody can also be, for example, chimeric, CDR-grafted, or humanized antibodies. The anti-SKN-1 polypeptide antibody can also be generated in a non-human organism, e.g., a rat or mouse, and then modified, e.g., in the variable framework or constant region, to decrease antigenicity in a human.

Another approach to inhibiting SKN-1 activity is the administration of a SKN-1 antagonist that binds to (i.e., blocks) SKN-1 polypeptides and prevents it from interacting with its target gene (e.g., a gene involved in the oxidative stress response, e.g., a Phase II detoxification gene). Such SKN-1 polypeptide antagonists can be identified using a screening method described herein. Alternatively, the SKN-1 antagonist can be an anti-SKN-1 polypeptide antibody, or fragment thereof, as described above.

Inhibition of the Response by GSK-3 Activators

A stress response, e.g., an oxidative stress response, e.g., an SKN-1-mediated oxidative response, can be inhibited by supplementing or providing new GSK-3 activity. For example, new or supplemental GSK-3 activity can be provided in vivo by direct administration of a recombinant GSK-3 polypeptide, e.g., to pathogenic nematodes prior to, during, and/or after their introduction into the environment of interest. GSK-3 polypeptides that can be used to supplemental GSK-3 activity are described herein. Such polypeptides can be used "as is" or modified. Examples of modifications include derivation of amino acid side chains, glycosylation, conservative amino acid substitutions, and chemical conjugation or fusion to other non-GSK-3 polypeptide moieties.

Alternatively or in addition, a GSK-3 polypeptide can be introduced indirectly into an organism, e.g., a nematode, by expressing within the cells of the organism a nucleic acid construct containing a nucleotide sequence encoding a GSK-3 polypeptide. Any appropriate expression vector suitable for transfecting the cells of the organism of interest can be used in the invention. The nucleic acid construct can be derived from a non-replicating linear or circular DNA or RNA vector, or from an autonomously replicating plasmid or viral vector. Methods for constructing suitable expression vectors are known in the art, and useful materials are commercially available.

Activation of the Response by SKN-1 Activators

In some embodiments, the invention provides for activating the SKN-1-mediated oxidative stress response. Agents that activate can be used, e.g., to increase the oxidative stress resistance of beneficial pathogenic nematodes, e.g., those used to protect crops by eliminating/controlling the population of certain insects. Examples of such nematodes are *Stein-*

*ernema carpocapsae, S. Glaseri* and *Heterorhabditis* spp. Such agents are also useful for, e.g., activating the oxidative stress response via SKN-1 in a laboratory/research setting in order to identify other genes and/or proteins involved in the oxidative stress response pathway.

For example, new or supplemental SKN-1 activity can be provided in vivo by direct administration of a recombinant SKN-1 polypeptide, e.g., to pathogenic nematodes prior to, during, and/or after their introduction into the environment of interest. SKN-1 polypeptides that can be used to supplemental SKN-1 activity are described herein, e.g., SEQ ID NO:2, or a fragment thereof. Another is described in Example 1. There, a SKN-1/green fluorescent protein fusion protein is described. Such polypeptides can be used "as is" or modified. Examples of modifications include derivation of amino acid side chains, glycosylation, conservative amino acid substitutions, and chemical conjugation or fusion to other non-SKN-1 polypeptide moieties.

Alternatively or in addition, a SKN-1 polypeptide can be introduced indirectly into an organism, e.g., a nematode, by expressing within the cells of the organism a nucleic acid construct containing a nucleotide sequence encoding a SKN-1 polypeptide. Any appropriate expression vector suitable for transfecting the cells of the organism of interest can be used in the invention. The nucleic acid construct can be derived from a non-replicating linear or circular DNA or RNA vector, or from an autonomously replicating plasmid or viral vector. Methods for constructing suitable expression vectors are known in the art, and useful materials are commercially available. With respect to nematodes, an example for producing transgenic skn-1::gfp strains of *C. elegans* discussed in detail in Example 1.

Another approach to increasing SKN-1 activity is the administration of an antioxidant (e.g., sulforaphane) or other compound, e.g., a compound isolated using one of the screening methods described above. Such a compound can be, e.g., a small organic or inorganic molecule, e.g., a novel antioxidant.

Activation of the Response by GSK-3 Inhibitors

A stress response, e.g., an oxidative stress response, e.g., an SKN-1-mediated oxidative response, can be activated by an inhibitor of GSK-3 expression or activity. Any of the methods described for inhibiting SKN-1 expression or activity described herein, e.g., the use of antisense or antibodies, can be used to inhibit the expression or activity of GSK-3. GSK-3 activity can also be inhibited by administering a GSK-3 antagonist that binds to (i.e., blocks) GSK-3 polypeptides. GSK-3 antagonists are known, and include, e.g., lithium, SB-415286 (see, e.g., MacAulay et al. (2003) *Eur. J. Biochem.,* 270:3829-38), GBP (see, e.g., Yost et al. (1998) *Cell,* 93:1031-41), and AR-A014418 (see, e.g., Bhat et al. (2003) *J. Biol. Chem.,* 278:45937-45).

Pharmaceutical Compositions

The compounds, nucleic acids, and polypeptides, fragments thereof, as well as antibodies, e.g., anti-SKN-1 polypeptide antibodies, anti-GSK-3 polypeptide antibodies, other molecules and agents of the invention (also referred to herein as "active compounds"), e.g., novel antioxidants, can be incorporated into pharmaceutical compositions. Such compositions typically include the nucleic acid molecule, protein, or antibody and a pharmaceutically acceptable carrier. A "pharmaceutically acceptable carrier" can include solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fingi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be achieved by including an agent that delays absorption, e.g., aluminum monostearate and gelatin in the composition.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of, e.g., tablets, troches, or capsules, e.g., gelatin capsules. Oral compositions can also be prepared using a fluid carrier for use, e.g., as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g. for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue, e.g., bone or cartilage, in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

For the SKN-1 or GSK modulating agents described herein, an effective amount, e.g., of a protein or polypeptide (i.e., an effective dosage), ranges from about 0.001 to 30 mg/kg body weight, e.g. about 0.01 to 25 mg/kg body weight, e.g. about 0.1 to 20 mg/kg body weight. The protein or polypeptide can be administered one time per week for between about 1 to 10 weeks, e.g. between 2 to 8 weeks, about 3 to 7 weeks, or for about 4, 5, or 6 weeks. The skilled artisan will appreciate that certain factors influence the dosage and timing required to effectively treat a patient, including but not limited to the type of patient to be treated, the severity of the disease or disorder, previous treatments, the general health and/or age of the patient, and other diseases present. Moreover, treatment of a patient with a therapeutically effective amount of a protein, polypeptide, antibody, or other compound can include a single treatment or, preferably, can include a series of treatments.

For antibodies, a useful dosage is 0.1 mg/kg of body weight (generally 10 mg/kg to 20 mg/kg). Generally, partially human antibodies and fully human antibodies have a longer half-life within the human body than other antibodies. Accordingly, lower dosages and less frequent administration are possible. Modifications such as lipidation can be used to stabilize antibodies and to enhance uptake and tissue penetration. A method for lipidation of antibodies is described by Cruikshank et al. ((1997) *J. Acquired Immune Deficiency Syndromes and Human Retrovirology* 14:193).

If the agent is a small molecule, exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Nucleic acid molecules (e.g., SKN-1 or GSK-3 DNA) of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

The invention is illustrated in part by the following examples, which are not to be taken as limiting the invention in any way.

EXAMPLE 1

SKN-1 Links *C. elegans* Mesendodermal Specification to a Conserved Oxidative Stress Response

*C. elegans* Strains and Bioinformatics

Strains were maintained at 20° C. unless otherwise noted, using standard methods (Brenner, Genetics 77: 71-94 (1974)). Alleles used were N2 Bristol as the wild-type, and skn-(zu67) and (zu129) (Bowerman et al. Cell 68: 1061-1075 (1992)). *C. elegans* orthologs of Nrf targets and other detoxification genes were identified by searching WORMpep or genomic databases (Sanger Centre). Predicted SKN-1 sites (FIG. 1C) 5' of their coding regions were identified with TFSEARCH (Heinemeyer et al. Nucleic Acids Res 26: 362-367 (1998)).

Paraquat Sensitivity and Lifespan Assays

To assay sensitivity to paraquat, young adults were transferred from NGM agar plates into 24-well plates (6 per well) containing 0.3 μl of M9 that either did or did not contain 100 mM paraquat. Worms were incubated at 20° C., and the number of dead animals was counted by the continuous absence of swimming movements and pharyngeal pumping. Lifespan assays were performed essentially as described by Hsin et al. (Nature 399: 362-366 (1999)). Animals were transferred to new plates daily and classified as dead when they did not move after repeated prodding with a pick. Animals that crawled away from the plate, exploded, or contained internally hatched worms were excluded from the analysis.

Plasmid Constructions

Figures 5A, 5B, 5C, 5D, 5E, 5F, 5G:
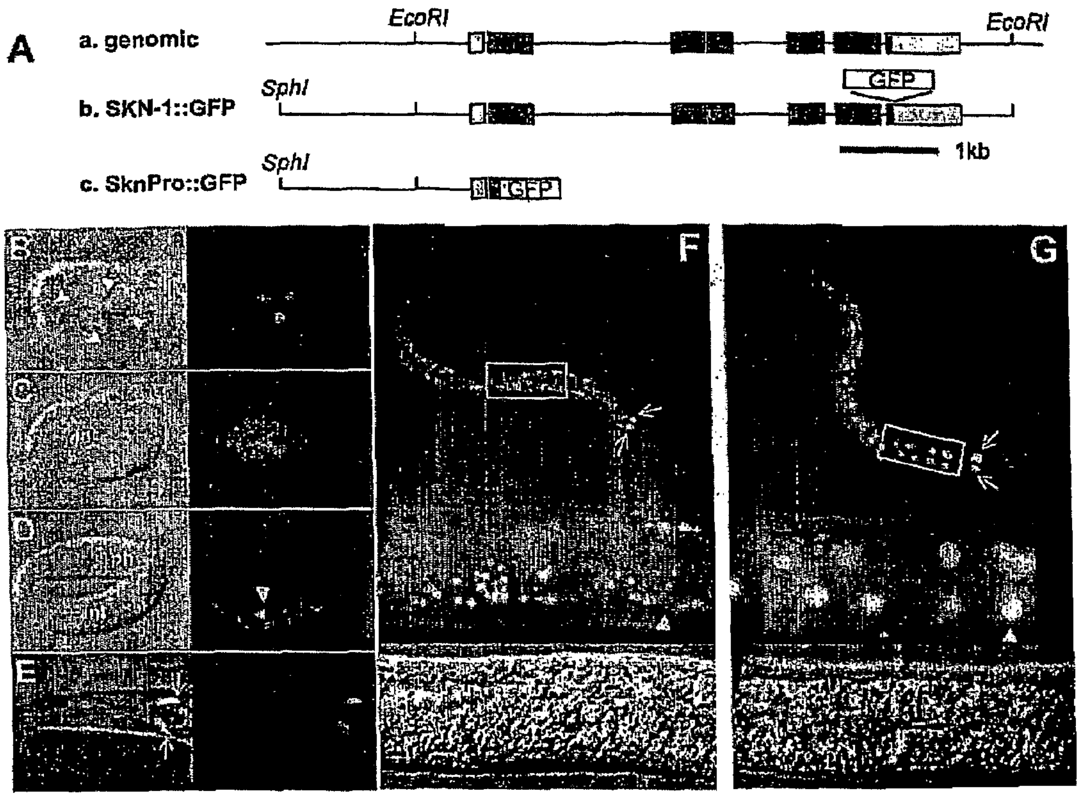
FIGS. 5A-5G: Expression and stress-induced nuclear accumulation of SKN-1::GFP. 5A: SKN-1::GFP transgenes a. skn-1 gene. Transcribed coding and untranslated regions are indicated in dark grey and light grey, respectively. b. SKN-1::GFP translational fusion construct, which includes an EcoR1 fragment that previously rescued maternal skn-1 lethality. *C. elegans* DNA is indicated by a black line. c. SknPro::GFP promoter fusion, in which the 38 N-terminal SKN-1 amino acids are fused to GFP containing a nuclear localization signal. 5B-5D: Embryonic expression of SKN-1::GFP. 5B, 5C, and 5D show Nomarski (left) and fluorescent (right) views, of 100 cells, 280 min., and three fold embryos, respectively. Endogenous intestinal autofluorescence was visible as yellow or orange in the original. White triangles indicate intestine precursor nuclei. Int: intestine. Ph: pharynx. 5E: SKN-1::GFP expression in ASI neurons (arrows). Nomarski/fluorescent (left) and fluorescent (right) views are shown of a typical DiI-exposed L4 larva. 5F: Larval SKN-1::GFP expression under normal conditions. Fluorescent and Nomarski closeups of the boxed region of this L2 are shown at bottom. Note the low-level SKN-1::GFP expression in intestinal nuclei (white triangle). 5G: SKN-1::GFP localization under oxidative stress. Examination of multiple focal planes revealed that SKN-1::GFP levels were not substantially altered in ASI neurons (arrows), but in many animals were dramatically increased in intestinal nuclei (Table 3). A heat-shocked L2 is shown, but similar results were obtained upon exposure to other oxidative stress inducers (Table 3). The integrated strain Is007 is shown, but two extrachromosomal lines and a different integrated line exhibited similar patterns.

All PCR was performed using Pfu polymerase (Stratagene). GFP vectors pPD95.67 and pPD114.35 were obtained. A skn-1::gfp promoter fusion construct (SknPro::GFP; FIG. 5A) was created by ligating GFP vector pPD95.67 and an PCR-amplified 2.1 kb clone containing the promoter region and 38 amino acids from first ATG codon of the skn-1 gene from cosmid T19E7 (sequence information about this cosmid can be accessed in WormBase under number T19E7). To generate the SKN-1::GFP translational fusion construct (FIG. 5A), the 5.7 kb EcoRI DNA fragment that rescues the maternal skn-1 phenotype and encodes the 533 amino acid SKN-1 protein (Bowerman et al. *Cell* 68: 1061-1075 (1992)) was amplified from cosmid B0547. A ClaI site was created immediately 3' to the SKN-1 C-terminus by the Quick Change method (Stratagene), which was used for all site-directed mutagenesis. This EcoRI fragment was subcloned into pUC18 that contained the upstream 1.3 kb SphI-EcoRI fragment from SknPro::GFP (FIG. 5A). A 0.8 kb CaI fragment that contained the GFP open reading frame (amplified from plasmid pPD114.35) was then cloned into the CaI site to generate an in-frame exon fusion of GFP to the SKN-1 C-terminus.

The *C. elegans* gcs-1ORF (WormBase number F37B12.2) is between 45% and 54% identical to human, mouse, *Drosophila* and yeast GCS(H) (data not shown). To construct the gcs-1::gfp transgene, a fragment that contained 1840 bp upstream of the initiation ATG, along with sequences encoding the 17 amino terminal GCS-1 residues, was amplified by PCR from cosmid F37B12, and cloned into GFP vector pPD95.67. Promoter deletions were similarly constructed by PCR. In gcs-1 point mutation constructs, predicted SKN-1 sites (underlined) were altered as follows: Site 1—608 GATGACAAT to CTGCAGAAT, Site 2—317 GATGACTTA to CTGCAGTTA and Site 3—121 TTTATCATC to TTTCTGCAG.

Transgenic Analyses

Transgenic strains were generated by injecting DNA into the gonad of young adult animals as described in Mello et al. (EMBO Journal 10: 3959-3970 (1991)). gcs-1::gfp transgene constructs (FIG. 3A) were injected at 50 ng/μl along with the rol-6 marker (pRF4) at 100 ng/μl. Between three and six independent extrachromosomal lines were generated and analyzed for each gcs-1::gfp construct. To investigate GCS-1::GFP expression in the skn-1(zu67) background, rol-6-marked gcs-1::gfp hermaphrodites were mated with N2 males, then their transgenic progeny were crossed with skn-1(zu67)/DnT1 hermaphrodites, which have an unc phenotype. After transgenic males were successively crossed twice with skn-1(zu67)/DnT1 hermaphrodites, unc; rol F3 hermaphrodite progeny were selected. From this population, skn-1(zu67)/DnT1; gcs-1::gfp animals were identified on the basis of their non-unc; rol progeny laying dead eggs. Two different gcs-1:gfp lines were thereby crossed into the skn-1 (zu67) background and examined for GFP expression. DIC and fluorescence images were acquired with a Zeiss AxioSKOP2 microscope and AxioCam cooled color digital camera.

To investigate expression of gcs-1::gfp and mutant transgenes, worms were exposed to oxidative stress under the following conditions. For heat shock, worms cultured at 20° C. were transferred onto prewarmed seeded plates and incubated at 29° C. for 20 hours, then examined by fluorescence microscopy for GFP expression. gcs-1::gfp induction was also observed in an alternative heat treatment protocol, during which worms cultured at 20° C. were transferred onto prewarmed plates and incubated at 34° C. for 2 to 4 hours, then returned to 20° C. and examined for GFP expression hourly during a four hour recovery period. In the experiments described in Table 2, young adults were transferred to plates that contained 1 mM paraquat in the agar and maintained at 20° C. for 3 days prior to analysis. In an alternative induction protocol, worms that carried gcs-1::gfp or the mutant transgenes shown in FIG. 3A were incubated in M9 either with or without 100 mM paraquat for 30 minutes, then allowed to recover on plates for four hours. The latter procedure also resulted in induction of intestinal gcs-1::gfp expression by paraquat but was associated with a higher background in uninduced animals.

To create transgenic skn-1::gfp strains, 2.5, 10, or 50 ng/μl of transgene DNA (FIG. 5A) was injected into N2 animals at along with 100 ng/μl of pRF4 to generate extrachromosomal transgenic lines. Two different extrachromosomal arrays, Ex001 and Ex007, generated with 2.5 and 10 ng/μl of SKN-1::GFP, respectively, were integrated into the chromosome by UV irradiation (400 J/m2) to produce the insertion strains Is001 and Is007, respectively. To rescue the embryonic lethality of a skn-1 mutation, SKN-1::GFP was injected into skn-1(zu67)/DnT1 animals at 2.5 ng/μl with 100 ng/μl of the pRF4 marker. Rescue of maternal skn-1 lethality was observed in some rol; non-unc progeny but not in non-rol; non-unc animals. SKN-1::GFP expression analyses shown were performed in the Is007 strain, but essentially the same results were obtained in analyses of Ex001, Ex007, and Is001 (data not shown). To analyze expression and localization of SKN-1::GFP in response to oxidative stress, skn-1::gfp transgenic worms were treated as described above for the gcs-1::gfp expression studies. In addition, for exposure to sodium azide animals cultured at 20° C. were placed upon a 2% agarose pad on a slide in M9 either with or without 50 mM sodium azide, then covered with a slip and examined by fluorescence microscopy. These worms were scored for presence of SKN-1::GFP in intestinal nuclei 5 minutes later. For photography, worms were immobilized either 2 mM Sodium Azide (FIG. 2, 3) or 2 mM Levamisole (FIG. 5). These treatments did not stimulate either GCS-1::GFP induction or SKN-1::GFP relocalization during the times examined (data not shown). No immobilization agent was used in the experiments shown in Tables 2 and 3. To discriminate intestinal autofluorescence from SKN-1::GPP epifluorescence, a triple band emission filter set (Chroma 61000) was used in conjunction with a narrow band excitation filter (484/14 nm). This combination allowed autofluorescence to be detected as yellow/orange fluorescence deriving from a combined green and red signal, while GFP remained green. Worms that carried skn-1::gfp, gcs-1::gfp and gcs-1::gfp mutant transgenes were incubated with 50 μg/ml DiI (Molecular Probes) in M9 for 3 hours at 20° C., then transferred to fresh plates for 1 hour to destain, and examined under the fluorescence microscope. The ASI chemosensory neurons were identified by according to their intensity of DiI labeling and location relative to other DiI-labeled cells.

DNA Binding Assays

Full-length SKN-1 and the SKN domain were expressed by in vitro translation (Promega) as described previously (Carroll et al., Genes Dev. 11: 2227-2238 (1997)). Oligonucleotide probes were end-labeled using Klenow and α-$_{32}$P-labelled dATP and CTP, then purified using QIAquick Kit (Qiagen). EMSAs were performed essentially as described in Blackwell et al. (Science 266: 621-628 (1994), with labeled probes present at $2.5\times10^{-9}$ M.

Constitutive and Inducible Phase H Detoxification Gene Activation by SKN-1

Vertebrate Nrf proteins induce expression of Phase II detoxification enzyme genes by binding to the characteristic antioxidant response element (ARE) in their promoters (FIG. 1C) (Hayes et al. Cancer Lett 174: 103-113 (2001)). A search was performed for SKN-1 binding sites within the predicted promoters of *C. elegans* orthologs of these oxidative stress resistance genes. The SKN-1 binding site preference and the ARE are distinct but not mutually exclusive (FIG. 1C). A predicted SKN-1 site should appear randomly every 2048 bp, but between two and four SKN-1 sites are present within 1 kb upstream of multiple *C. elegans* genes that encode predicted Phase II detoxification enzymes, including γ-glutamine cysteine synthase heavy chain (GCS(h)), glutathione synthetase, and four glutathione S-transferase (GST) isoforms (Table 1). In vertebrates each of these genes is activated by Nrf proteins (Id.). SKN-1 sites or variants that differ at only one AT-rich region position are similarly present 5' of the Nrf target NADH quinone oxidoreductase, the catalase ctl-1, and superoxide dismutases (sod-1, -2 and -3) (see Table 1, below).

TABLE 1

Predicted SKN-1 binding sites upstream of *C. elegans* oxidative stress resistance genes

| Enzymes | Gene or ORF | Location[a] | Direction | Sequence |
|---|---|---|---|---|
| γ-glutamyl-cysteine | gcs-1 | -121 | → | TTTATCAT |
| synthelase heavy chain | | -316 | ← | ATGACTTA |
| (GCS(h)) | | -607 | ← | ATGACAAT |
| Glutathione synthetase | N176.2 | -137 | → | TTTGTCAT |
| | | -169 | ← | ATGACAAA |
| | | -243 | → | TTTATCAT |
| | | -378 | ← | ATGATTTT |
| NADH quinone | F39B23 | -469 | → | GTTATCAT |
| oxidoreductase | | -518 | ← | ATGACAAT |
| Glulathione | R03D7.6 | -149 | ← | ATGACAAT |
| S-transferase | | -282 | ← | ATGATTTT |
| | | -302 | ← | ATGACATT |
| | | -947 | ← | ATGATTTT |
| | F35E8.8 | 94 | ← | ATGACAAT |
| | | -240 | ← | ATGATAAT |
| | FI1G11.2 | -133 | ← | ATGACAAA |
| | | -391 | → | CTTATCAT |

TABLE 1-continued

Predicted SKN-1 binding sites upstream of *C. elegans* oxidative stress resistance genes

| Enzymes | Gene or ORF | Location[a] | Direction | Sequence |
|---|---|---|---|---|
| | K08F4.7 | -83 | ← | ATGACATT |
| | | -157 | → | TTTGTCAT |
| Superoxide dismutase | sod-1 | -64 | → | ATAATCAT |
| | sod-2 | -191 | → | TGTATCAT |
| | | -363 | ← | ATGACAAT |
| | | -959 | → | AGAATCAT |
| | | -980 | → | AGAATCAT |
| | sod-3 | -287 | → | TAAATCAT |
| Catalase | ctl-1 | -880 | → | ATGATCAT |
| | | -978 | → | GTCATCAT |
| | | -997 | → | CTTATCAT |

The SKN-1 binding consensus is shown in Figure 1C.
[a]The A within the translation initiation codon is designated as base 1.

Figures 2A, 2B, 2C, 2D, 2E, 2F, 2G, 2H, 2I, 2J, 2K, 2L:
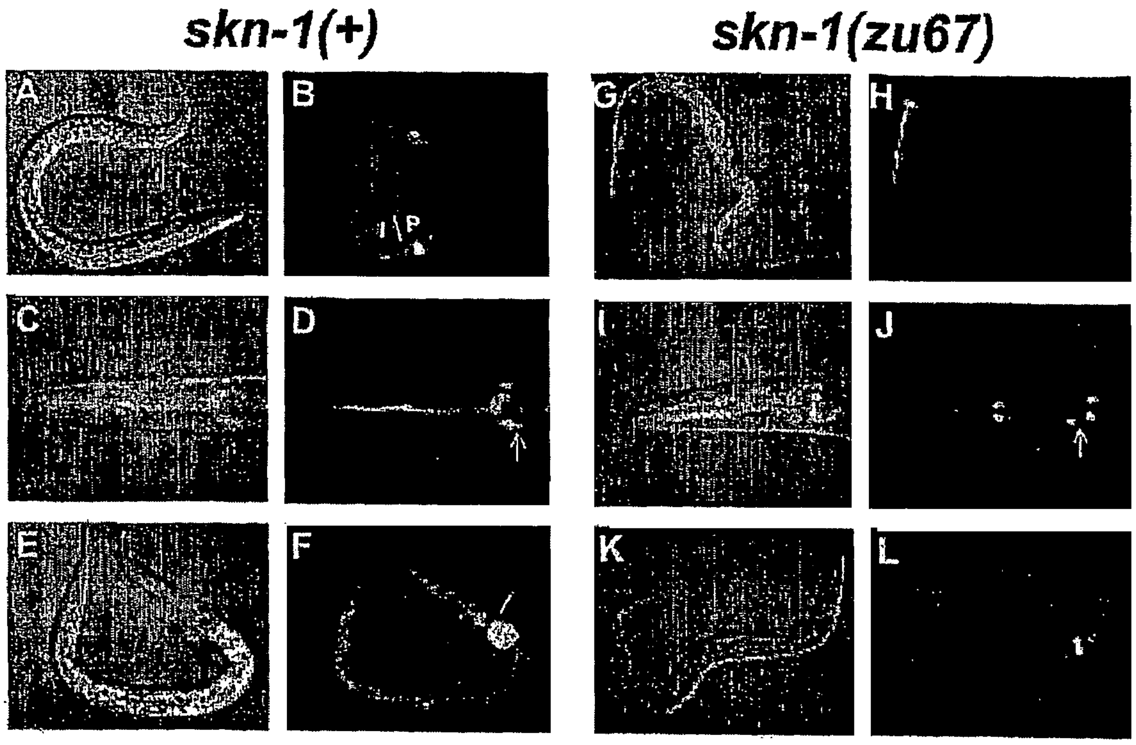
FIGS. 2A-2L: skn-1-dependent GCS-1::GFP expression in the intestine and ASI neurons. 2A-2F: GCS-1::GFP expression in wild type animals. A gcs-1 genomic fragment containing its 17 amino terminal codons and 1840 upstream bp was fused to the amino terminus of GFP that contained a nuclear localization signal. Expression patterns shown are each representative of more than two independent transgenic lines, and of all postembryonic stages examined (L2—adult; data not shown). 2A and 2B show Nomarski and fluorescent views, respectively, of an L2 larva. In 2B a line demarcates the approximate boundary between the anterior intestine (I) and posterior pharynx (P). 2C and 2D show combined Nomarski/fluorescent and fluorescent views, respectively, of the head of a typical L4 stage animal that had been exposed to DiI. In 2D one of the two ASI neurons is indicated with an arrow. 2E and 2F show an L2 larva in which GCS-1::GFP expression was induced to high levels in the intestine by heat. A similar induction occurred in response to paraquat (Table 2). The boundary between the anterior intestine and posterior pharynx is indicated as in 2B. 2G-2L: GCS-1::GFP was not detectable outside of the pharynx in skn-1 homozygotes. Typical animals are shown from experiments that parallel those displayed to the left in 2A-2F. Note the absence of GCS-1::GFP in the intestine and ASI neurons under normal conditions 2G-2J, and after treatment with heat (2K, 2L) or paraquat (data not shown). In two independent transgenic lines, in a homozygous skn-1 background GCS-1::GFP expression was not detected in these tissues in any animals under either normal or induction conditions.

Presence of SKN-1 site clusters upstream of multiple *C. elegans* Phase II detoxification genes is consistent with SKN-1 functioning analogously to Nrf proteins. To confirm this, whether SKN-1 is required to express the Phase II gene gcs-1 (Table 1) was investigated. gcs-1 is the *C. elegans* ortholog of GCS(h), a representative and well-characterized Nrf protein target gene that in yeast is regulated by Yap1p and Pap1p (Id., and Toone et al., Curr Opin Genet Dev 9: 55-61 (1999)). The GCS(H) enzyme is important for oxidative stress resistance because it is rate-limiting for glutathione synthesis.

gcs-1 expression in *C. elegans* was investigated using a transgene that included the predicted gcs-1 promoter, along with the 17 amino terminal GCS-1 amino acids fused to green fluorescent protein (GFP). This promoter segment contained three consensus SKN-1 binding sites, and corresponded to the intervening sequence between gcs-1 and the nearest upstream gene (data not shown). With this strategy, it was possible to analyze gcs-1 expression independently of GCS-1 protein stability. In a wild-type background, during larval and adult stages GCS-1::GFP was readily detectable in the pharynx, and in nearby cells that appeared to be neurons (FIGS. 2A and B). By soaking gcs-1::gfp lines in DiI, a dye that fills amphid sensory neurons (Herman et al., Nature 348:169-171 (1990)), it was determined that two GCS-1::GFP-expressing cells located adjacent to the posterior pharynx correspond to the ASI chemosensory neurons (FIGS. 2C and 2D), which prevent constitutive entry into the dauer diapause state (Ren et al. 1996; Schackwitz et al. 1996). GCS-1::GFP expression was also apparent anteriorly and posteriorly in the intestine (FIGS. 2A and 2B).

In vertebrates, oxidative stress induces Phase II gene expression through an Nrf2-dependent pathway in the intestine and liver (Itoh et al. 1997; Hayes and McMahon 2001). Similarly, stimuli that cause oxidative stress dramatically increased GCS-1::GFP expression in the *C. elegans* intestine (FIGS. 2E and 2F, and see Table 2, below). This response was triggered by both heat and the herbicide paraquat (methyl viologen), which generates intracellular superoxide anions. To investigate the involvement of skn-1 in gcs-1 expression, we introduced the gcs-1::gfp transgene into the skn-1(zu67) background, the skn-1 allele that is associated with the most severe embryonic phenotype (Bowerman et al. *Cell* 68: 1061-1075 (1992)). Under both normal and oxidative stress conditions, in skn-1(zu67) homozygotes GCS-1::GFP was apparent at wild-type levels in the pharynx, but was otherwise undetectable (FIGS. 2G-2L), indicating that skn-1 is essential for both constitutive and inducible gcs-1::gfp expression outside of the pharynx.

Figures 3A, 3B, 3C:
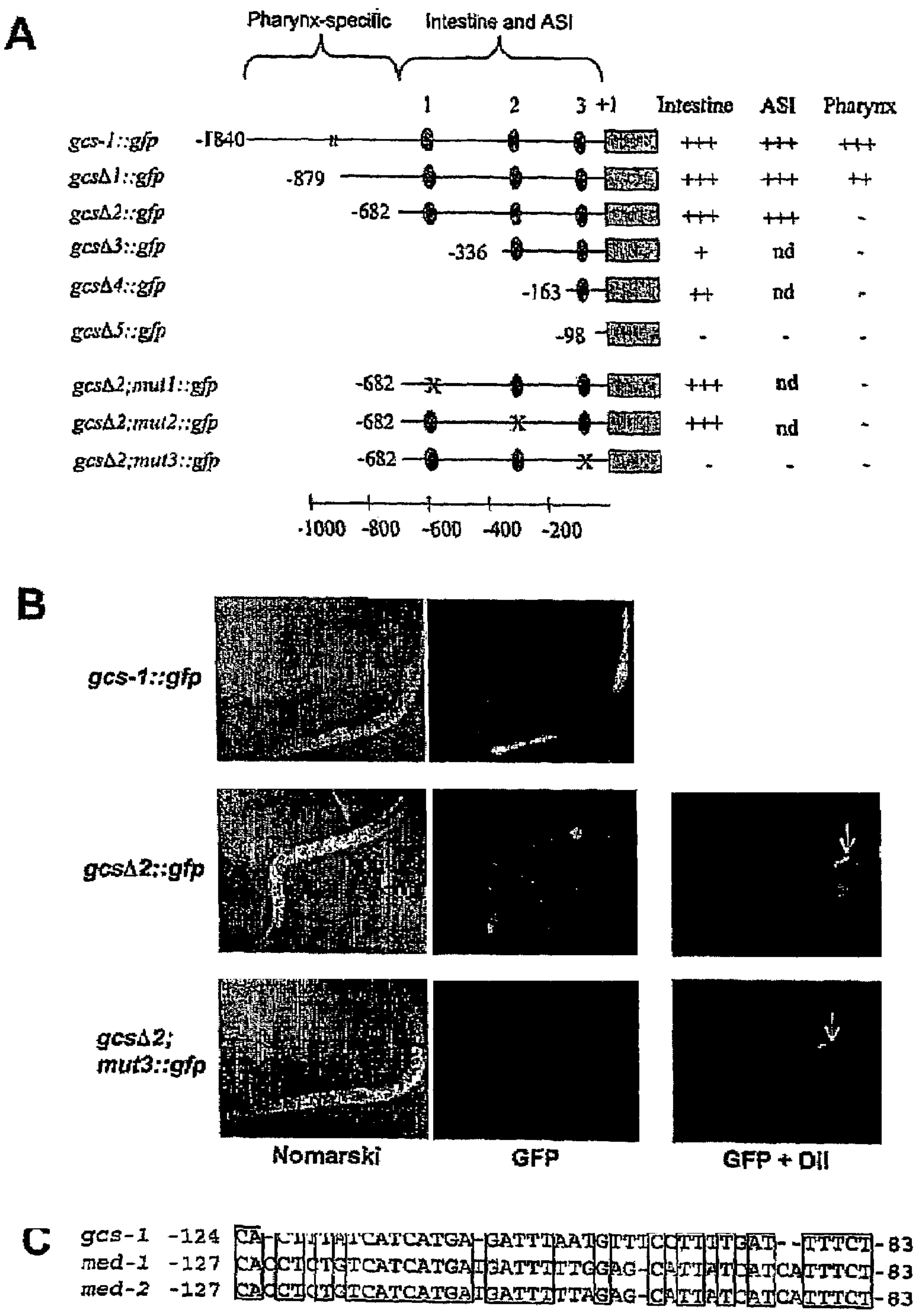
FIGS. 3A-3C: Specific elements required for skn-1-independent and -dependent GCS-1::GFP expression. 3A: Analysis of the gcs-1 promoter. Expression of the indicated constructs from transgenic extrachromosomal arrays was assayed in 2-3 independent transgenic lines, under normal conditions and after induction by paraquat and heat. Approximate relative expression levels in the tissues designated to the right (data not shown) are indicated by + signs, with ++ indicating a reproducible reduction, and + indicating barely detectable expression. Within each set of transgenic lines that carried promoter mutations, levels of normal and induced expression were affected in parallel. Mutations that were created in predicted SKN-1 sites 1, 2, and 3 are described in Materials and Methods, and are not compatible with SKN-1 binding (see text). Grey ovals indicate predicted SKN-1 binding sites and a grey bar the 5' end of the gcs-1::gfp coding region. Map numbers refer to the predicted translation start. 3B: Uncoupling pharyngeal GCS-1::GFP expression from intestinal and ASI neuron expression. The gcsΔ 2 mutation eliminated pharyngeal GCS-1::GFP expression, but allowed near-wild type levels of ASI and intestinal expression. Concurrent ablation of SKN-1 binding site 3 (gcsΔ2,mut3) eliminated transgene expression in all tissues. Paraquat-treated worms are shown in the GFP column. 3C: Composite gcs-1 promoter element that includes SKN-1 site 3, and is also present in the med-1 and -2 promoters. SKN-1 binding sites are in a lighter grey font, and identical sequences are boxed.

Promoter mutagenesis identified discrete elements that are required for these skn-1-dependent and -independent gcs-1 expression patterns. Pharyngeal GCS-1::GFP expression was abolished by removal of the distal gcs-1 promoter region (gcsΔ2::gfp; FIGS. 3A and 3B), which lacks SKN-1 binding sites but contains consensus sites for the pharyngeal, transcription factors PEB-1 and PHA-4 (Thatcher et al. *Dev Biol* 229: 480-493 (2001); Gaudet et al., *Science* 295: 821-825 (2002)) (data not shown). The remaining proximal 682 bp of the gcs-1 promoter included the three predicted SKN-1 binding sites, and was sufficient for appropriate GCS-1::GFP expression in the intestine and ASI neurons (gcsΔ2::gfp, FIGS. 3A, 3B, Table 2). Constitutive and stress-induced GCS-1::GFP expression within the intestine and ASI neurons did not require SKN-1 binding sites 1 or 2 individually, but was abolished by alteration of site 3 (gcs 2,mut3::gfp; FIGS. 3A and 3B).

TABLE 2

Induction of GCS-1::GFP expression in the intestine by oxidative stress

| | gcs-1::gfp | | | | gcsΔ2::gfp | | | |
|---|---|---|---|---|---|---|---|---|
| Inducer | low | medium | high | N | low | medium | high | N |
| Control | 90.8% | 7.9% | 1.3% | 76 | 88.2% | 10.3% | 1.5% | 68 |
| Heat Shock | 10.5% | 72.4% | 17.1% | 76 | 0.0% | 14.0% | 86.0% | 86 |
| Paraquat | 14.5% | 67.1% | 18.4% | 76 | 21.3% | 65.6% | 13.1% | 61 |

A representative set of experiments involving a mixed population of L2-young adult worms is shown, from which percentages of animals in each expression category are listed. Induction of GCS-1::GFP expression was comparable among the different developmental stages analyzed. "Low" refers to animals similar to that in FIG. 2A, in which intestinal GCS-1::GFP was apparent at modest levels anteriorly, or anteriorly and posteriorly. "High" indicates that a GCS-1::GFP was present at high levels anteriorly and detectable throughout most of the intestine, as in FIG. 2F. "Medium" refers to animals in which GCS-1::GFP was present at high levels anteriorly as in FIG. 2F and possibly posteriorly, but was not detected in between. N indicates numbers of animals analyzed from each transgenic strain.

Figure 4A:
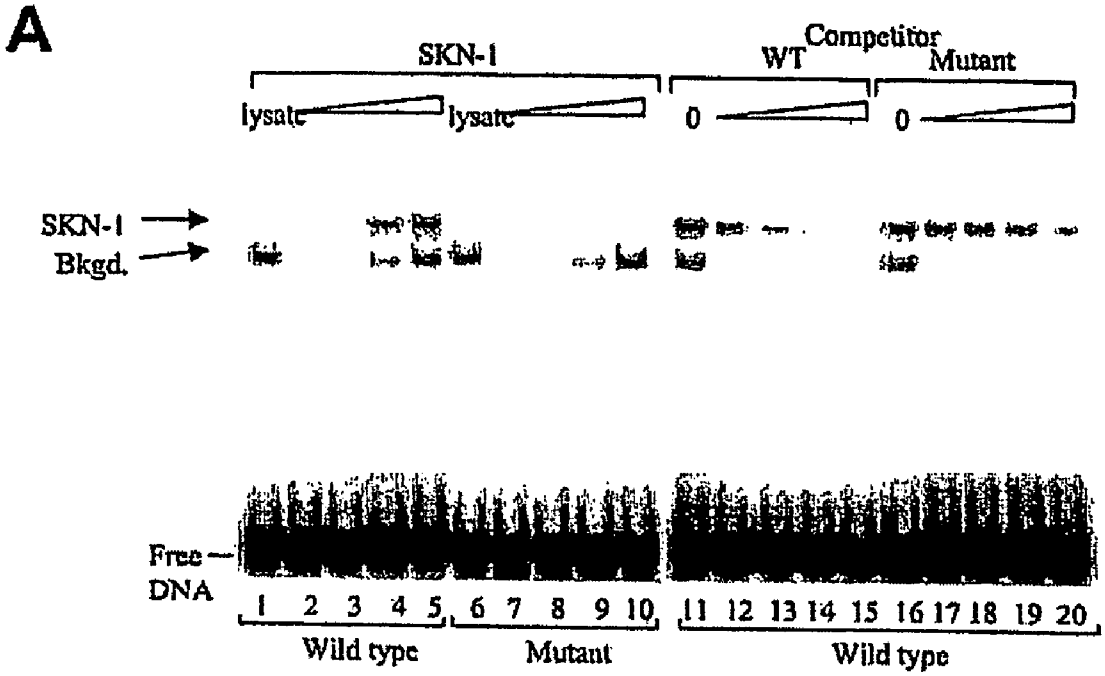
FIGS. 4A and 4B: Specific binding of SKN-1 to an essential gcs-1 promoter sequence. 4A: Binding of full-length SKN-1 to site 3 within the gcs-1 composite element, assayed by EMSA. Lanes 2-5 show binding of increasing amounts of in vitro translated SKN-1 protein (0 μl, 0.25 μl, 0.5 μl, 3 μl translation lysate; indicated by a triangle) to the wild type site. Lane 1 shows binding to 3 μl unprogrammed lysate. A background species is labeled. Lanes 6-10 show the same assay performed with the mutant probe. In lanes 11-20, SKN-1-DNA binding is assayed in the presence of the indicated unlabelled competitor oligonucleotides. Lanes 12-15 and 17-20 correspond to addition of a 20-, 50-, 150-, and 400-fold molar excess of competitor over the labeled wild-type DNA. 4B: The in vitro translated SKN-1 DNA binding domain (FIG. 1B) binds specifically to the gcs-1 composite element. Binding was assayed as in 4A.
Figure 4B:
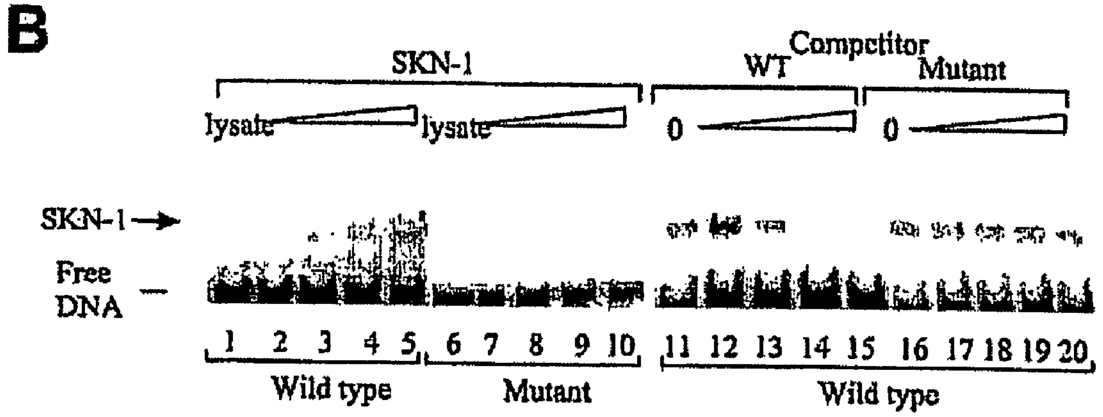

Remarkably, SKN-1 binding site 3 is located within a 42 bp gcs-1 promoter element that is similar to a composite motif through which SKN-1 activates med-1 and med-2 in the embryo (FIGS. 1A and 3C) (Maduro et al. Mol. Cell 7: 475-485 (2001)). The conservation between these gcs-1 and med promoter elements is particularly striking because they are located at identical distances from their respective translation starts, but contain different numbers of SKN-1 sites (FIG. 3C). In an electrophoretic mobility shift assay (EMSA), full-length SKN-1 and the 85 amino acid SKN-1 DNA binding domain (SKN Domain) (Blackwell et al. Science 266: 621-628 (1994)) each bound sequence-specifically to SKN-1 binding site 3 in the context of this gcs-1 promoter element (FIG. 4). These SKN-1 proteins bound with high affinity to an oligonucleotide that corresponds to this composite element (Wild type; FIGS. 4A and 4B, lanes 2-5), but not to an analogous probe in which SKN-1 site 3 had been altered as in the inactive gcsΔ2; mut3::gfp transgene (FIG. 3A; Mutant, FIGS. 4A and 4B, lanes 7-10). Binding of these SKN-1 proteins to the Wild type probe was also competed much more effectively by unlabeled Wild type than Mutant DNA (FIGS. 4A and B, lanes 11-20). Further supporting the importance of this gcs-1 promoter element, a 163 bp fragment that includes it provides significant GCS-1::GFP expression in the intestine, but 5' truncation within this sequence inactivates the promoter (gcsΔ4::gfp and gcsΔ5::gfp, FIG. 3A). It is evident that binding of SKN-1 to site 3 is required for gcs-1 expression in the intestine and ASI neurons.

SKN-1 Expression and Accumulation in Intestinal Nuclei in Response to Oxidative Stress To determine whether SKN-1 is present in tissues where it is required for gcs-1::gfp expression, expression of a transgene in which GFP is fused to the C-terminus of full-length SKN-1 (SKN-1::GFP; FIG. 5A) was analyzed. Although maternal skn-1::gfp expression was not readily detectable because of germline transgene silencing (Kelly et al., *Genetics* 146:227-238 (1997)), at a low frequency this transgene rescued the embryonic defect in skn-1(zu67) homozygotes (data not shown), indicating that this SKN-1::GFP fusion protein is functional.

In the embryo, antibody staining previously revealed presence of maternal SKN-1 in nuclei through the eight-cell stage, then detected zygotically expressed SKN-1 in only about 15% of late-stage embryos that had ceased dividing (Bowerman et al. *Cell* 74: 443-452 (1993)). Nuclear SKN-1::GFP was uniformly detected in intestinal precursors beginning at the 50-100 cell stage (FIG. 5B), then in both the intestine and hypodermis (FIG. 5C), indicating that SKN-1 is expressed zygotically earlier than it is detectable by antibody staining. In late-stage embryos SKN-1::GFP was also present in intestinal nuclei but not in the hypodermis (FIG. 5D), suggesting that hypodermal skn-1 expression may be maintained by a region located outside of this transgene.

In contrast to the embryo, in larvae and young adults SKN-1::GFP was usually present at very low levels in intestinal nuclei (FIG. 5F, and see Table 3, below). SKN-1::GFP was readily detectable in the ASI neurons, where gcs-1::gfp was constitutively expressed (FIGS. 5E and 5F), but not in other cells in the head where GCS-1::GFP expression appeared to be skn-1-dependent (FIGS. 2B and 2H). The latter skn-1 dependence might be indirect, or derived from low level SKN-1 expression or distant skn-1 regulatory regions. The finding that SKN-1::GFP is present at only modest levels in intestinal nuclei raises the question of how oxidative stress induces skn-1-dependent intestinal gcs-1 expression (FIGS. 2, 3, and Table 2, above). In cultured mammalian cells, Nrf2 is stabilized and relocalized from the cytoplasm to the nucleus in response to oxidative stress (Itoh et al. *Genes Dev* 13: 76-86 (1999); Sekhar et al. *Oncogene* 21: 6829-6834 (2002); Nguyen et al. *J Biol Chem* 278: 4536-4541 (2003); and Stewart et al. *J Biol Chem* 278: 2396-2402 (2003)). A promoter fusion transgene in which only the SKN-1 amino terminus was linked to GFP (SknPro::GFP, FIG. 5A) was constitutively expressed at high levels in all intestinal cells (data not shown), suggesting that SKN-1 expression or localization might also be regulated post-transcriptionally by oxidative stress.

After exposure to either paraquat or heat, neither the location nor intensity of SKN-1::GFP was detectably altered in the ASI neurons, but in a high percentage of animals elevated levels of SKN-1::GFP appeared in intestinal cell nuclei, particularly anteriorly and posteriorly where GCS-1::GFP is most robustly expressed (FIGS. 5F and 5G, Table 3). SKN-1::GFP accumulated in intestinal nuclei within 5 min, after treatment with 50 mM sodium azide (Table 3), which induces oxidative stress by blocking mitochondrial electron transport. The rapidity of this last response indicates that in the intestine SKN-1 is constitutively present, but may be diffuse within the cytoplasm and masked by autofluorescence. This accumulation of SKN-1::GFP in intestinal nuclei in response to oxidative stress remarkably parallels the skn-1-dependent induction of GCS-1::GFP under similar conditions, supporting the model that SKN-1 activates intestinal gcs-1 expression directly.

TABLE 3

Accumulation of SKN-1::GFP in intestinal nuclei in response to oxidative stress

| Inducer | low | medium | high | N |
|---|---|---|---|---|
| Control | 78.9% | 14.5% | 6.6% | 76 |
| Heat | 5.6% | 11.9% | 82.5% | 143 |
| Paraquat | 53.1% | 43.8% | 3.1% | 64 |
| M9, 5 min. | 74.7% | 17.6% | 7.7% | 91 |
| 50 mM Sodium Azide, 5 min. | 0.8% | 44.2% | 55.0% | 120 |

Mixed-stage L2-young adult transgenic worms were exposed to the indicated conditions. A representative set of experiments is shown, from which percentages of animals in each category are listed. SKN-1 localization patterns did not differ significantly among the different developmental stages examined. M9 refers to the control incubation for the sodium azide experiment. In some animals treated with sodium azide, high levels of nuclear SKN-1::GFP appeared in less than 1 minute (data not shown).
"Low" refers to animals in which SKN-1::GFP was barely detectable in all intestinal nuclei, as shown in FIG. 4F.
"High" indicates that a very strong SKN-1::GFP signal was present in all intestinal nuclei, as in FIG. 4G.
"Medium" refers to animals in which nuclear SKN-1::GFP was present at high levels anteriorly or anteriorly and posteriorly, but was barely detectable midway through the intestine.
N indicates numbers of animals analyzed in each category.

SKN-1 Accumulation in Intestinal Nuclei Following Inhibition of sgg-1 (GSK-3)

Figure 37:
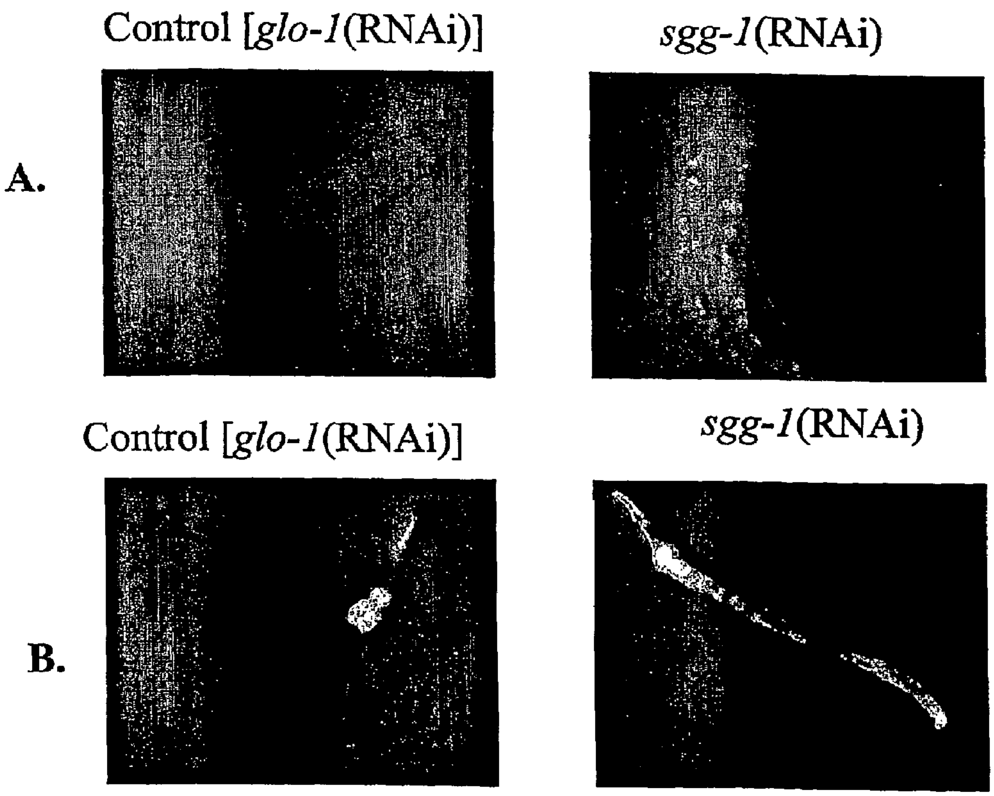
FIG. 37 is an image of (A) SKN-1::GFP localization and (B) GCS-1::GFP localization.

To determine the role of sgg-1 (GSK-3) in oxidative stress response, the effect of sgg-1 (GSK-3) inhibition on SKN-1 localization was investigated. When expression of sgg-1 (GSK-3) was reduced using sgg-1 (GSK-3) RNAi, SKN-1::GFP accumulated in intestinal nuclei (FIG. 37A). Further, GCS-1::GFP was induced moderately in sgg-1 (RNAi) worms (FIG. 37B). These findings indicate that sgg-1 (GSK-3) inhibits constitutive SKN-1 nuclear accumulation and induction of its target gene, gcs-1.

GSK-3 Directly Regulates SKN-1

Figure 38:
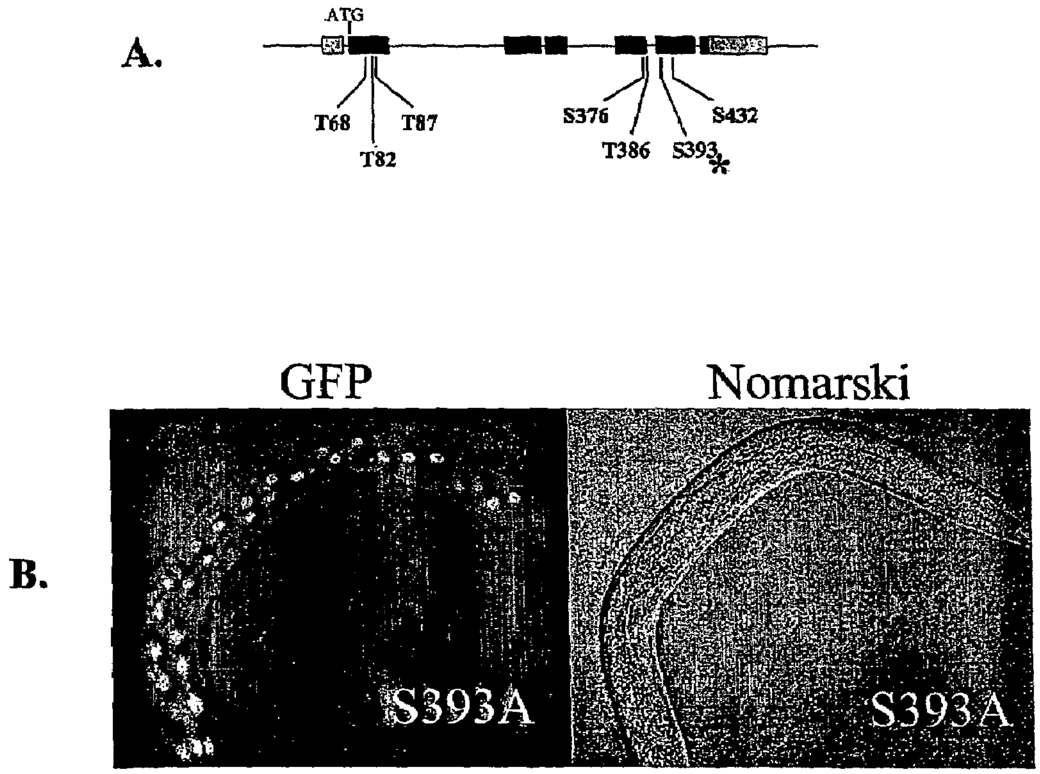
FIG. 38 is (A) a schematic of predicted phosphorylation sites in SKN-1 and (B) an image of mutant SKN-1::GFP localization.

To determine whether GSK-3 directly regulates SKN-1, seven predicted GSK-3 sites in SKN-1 were substituted with alanine (FIG. 38). Transgenic worms expressing alanine-substituted SKN-1 were analyzed for SKN-1::GFP localization. Alanine substitution resulted in nuclear accumulation of SKN-1, especially in transgenic worms expressing the SKN-1 mutant S393A.

Figure 39:
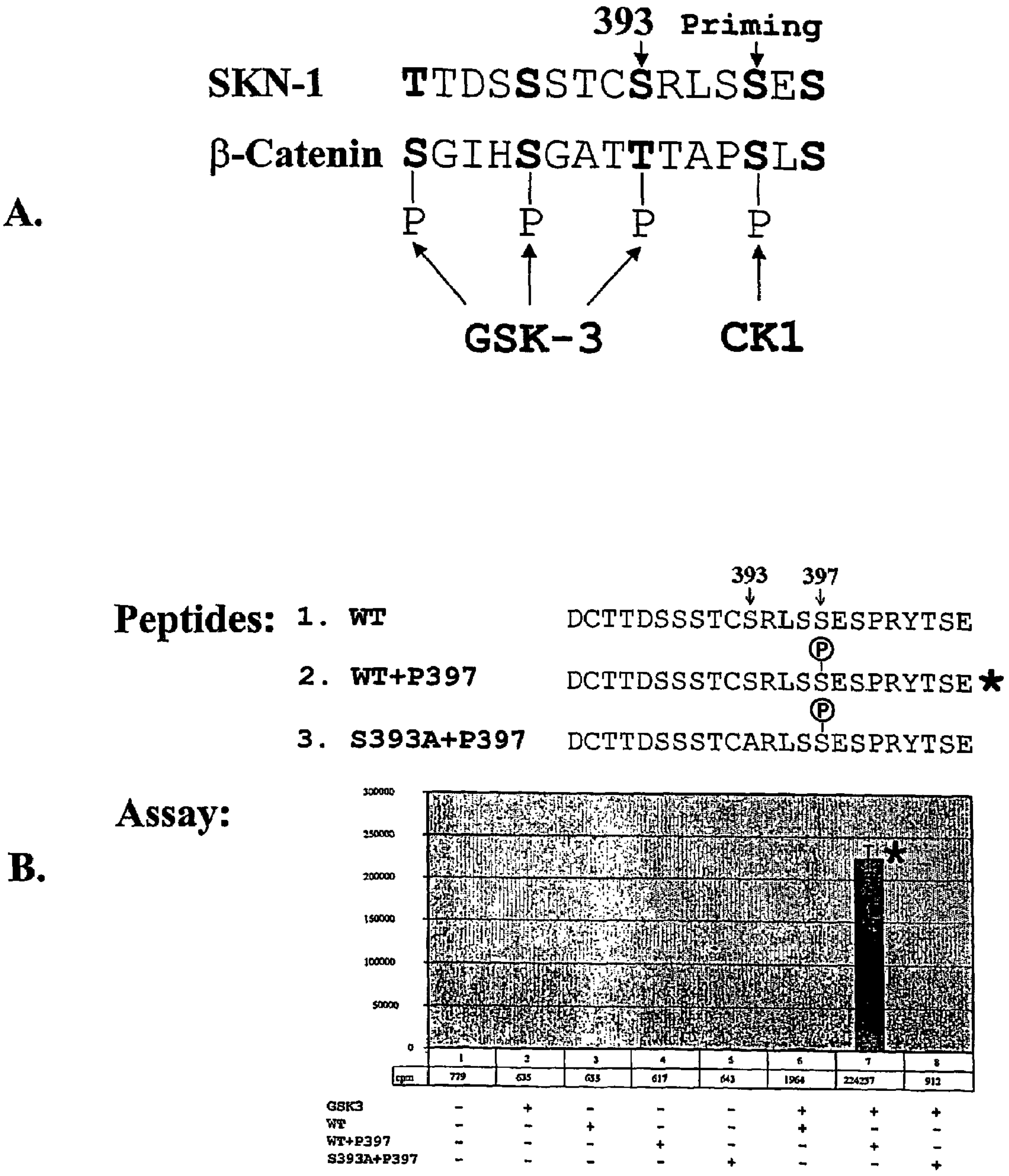
FIG. 39 is (A) a schematic of predicted phosphorylation sites (SEQ ID NO:51), (SEQ ID NO:52), (SEQ ID NO:53) and (SEQ ID NO:54) and (B) a graph of phosphorylation of various SKN-1 peptides by GSK-3.

Phosphorylation of SKN-1 by GSK-3 was also investigated. Phosphorylation by GSK-3 required priming phosphorylation at a serine or threonine residue located four positions carboxyl-terminal to the GSK-3 site (FIG. 39). GSK-3 then phosphorylates SKN-1 sequentially in the amino-terminal direction.

skn-1 Required for Oxidative Stress Resistance and Normal Longevity

Figures 6A, 6B:
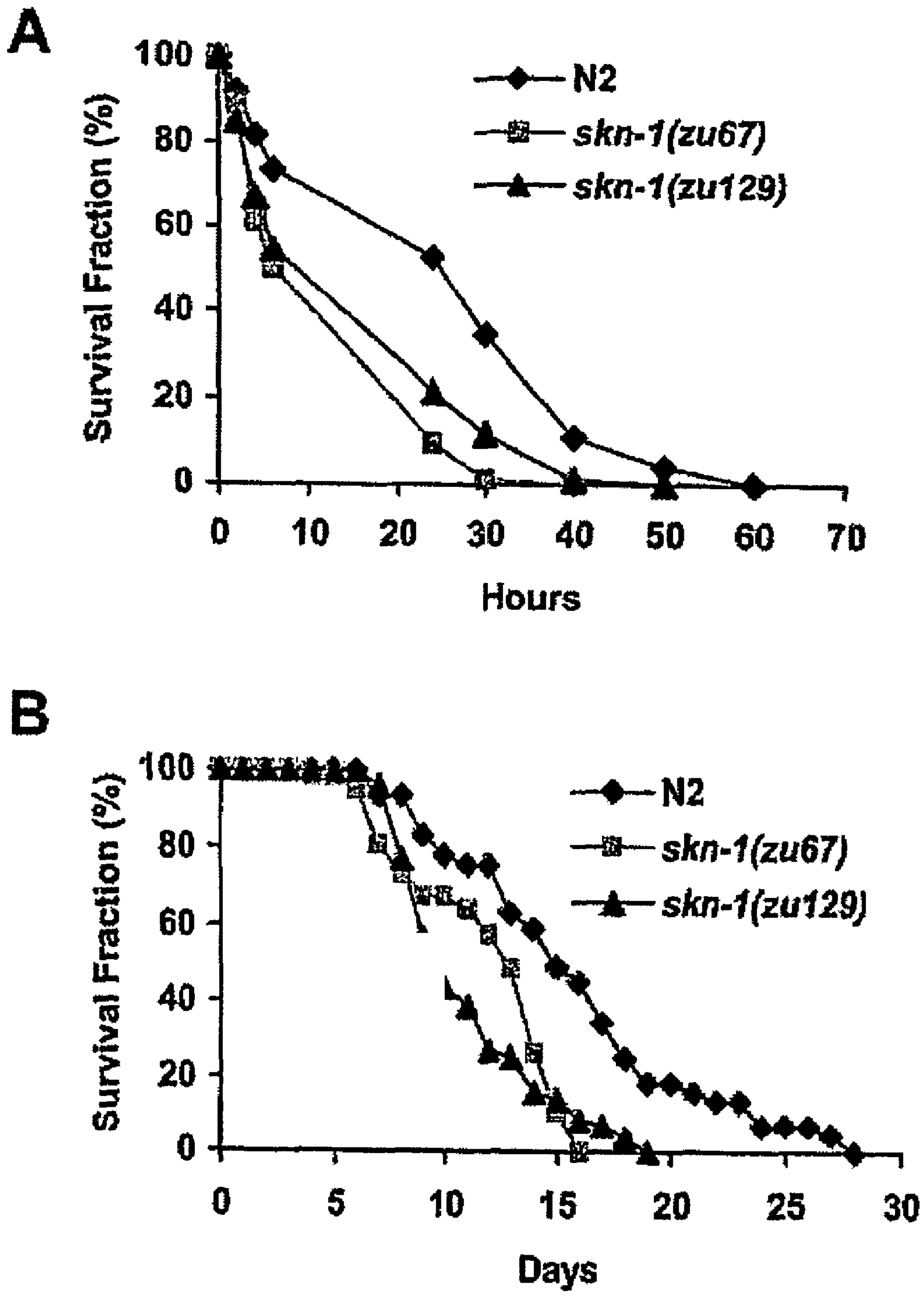
FIGS. 6A-6B: skn-1 mutants are sensitive to oxidative stress and have reduced lifespans. 6A: Paraquat sensitivity. Worms were scored for survival at the times shown after they had been placed in M9 that contained 100 mM paraquat. An average of three experiments involving 24 worms each is graphed. All wild type and skn-1 mutant worms survived a parallel control 72 hr. incubation in M9 alone (data not shown). 6B: Lifespan assay. Worms were maintained at 20° C. and scored for survival at the indicated time after the L4 stage. An average of three experiments involving 25-28 worms each is plotted. In wild type, skn-1(zu67), and skn-1 (zu129) strains, mean life spans were 15.9+2.2, 11.8+1.4, and 11.1+0.1 days, respectively. Mean maximum life spans were 24.3+3.5, 16.3+0.6, and 18.7+0.6 days, respectively.

Whether skn-1 mutants are abnormally sensitive to oxidative stress was investigated. skn-1(zu67) homozygotes produce normal numbers of offspring with normal timing, and as young adults are not obviously distinguishable in morphology from wild-type (data not shown). Two different skn-1 mutant alleles were associated with markedly decreased survival in the presence of paraquat however, indicating that skn-1 mutants are sensitive to oxidative stress (FIG. 6A).

Further, whether skn-1 homozygotes live as long as wild type was investigated. Both the mean and maximum lifespans of skn-1(zu67) and skn-1(zu129) homozygotes were reduced by 25-30% (FIG. 6B), indicating that SKN-1 is required for normal longevity.

A conserved Postembryonic Function for SKN-1 in Oxidative Stress Resistance

The *C. elegans* developmental specification protein SKN-1 also mediates a conserved response to oxidative stress. SKN-1 functions similarly to bZIP proteins that regulate Phase II detoxification genes in vertebrates (Nrf1, 2) and yeast (Yap1p, Pap1p). SKN-1 activates a conserved Phase II gene in the intestine and ASI neurons (FIGS. 2, 3, 5), SKN-1 binding sites flank *C. elegans* orthologs of additional Nrf target genes (Table 1), and skn-1 mutants are sensitive to oxidative stress (FIG. 6A). The accumulation of SKN-1 in intestinal nuclei in response to oxidative stress (FIG. 5G, and Table 3) may parallel nuclear accumulation of Nrf proteins, Yap1p, and Pap1p, under these conditions (Itoh et al. *Genes Dev* 13: 76-86 (1999); Toone et al. *Oncogene* 20: 2336-2346 (2001); and Delaunay et al., *Cell* 111: 471-81 (2002)). The intestinal abnormalities in skn-1(zu67)/nDf41 larvae (Bowerman et al. *Cell* 68: 1061-1075 (1992)) could involve oxidative stress, because 10-20% of gcs-1 (RNAi) animals also die as larvae with abnormal intestines (data not shown).

These parallels between SKN-1 and Nrf proteins are surprising because the mechanism through which SKN-1 binds DNA is both unique and highly divergent (Blackwell et al. *Science* 266: 621-628 (1994)). SKN-1 and Nrf proteins are most similar within the 14 amino acid DIDLID transactivation element (FIG. 1B) (Walker et al. *J. Biol. Chem.* 275: 22166-22171 (2000)).

While gcs-1 expression in the intestine is induced by SKN-1 in response to stress, presence of nuclear SKN-1 allows gcs-1 to be expressed constitutively in the ASI neurons, and gcs-1 expression is skn-1-independent in the pharynx (FIG. 2). In metazoans, Phase II genes thus can be activated through distinct pathways that may be important for functions of different tissues. For example, the finding that skn-1 functions constitutively in the ASI neurons, which inhibit dauer entry, suggests that although skn-1(zu67) homozygotes can enter the dauer stage (data not shown), skn-1 or oxidative stress might influence regulation of this process.

The lifespan reduction that observed in skn-1 mutants (25-30%, FIG. 6B) is comparable to that reported in daf-16 mutants (20%) Kenyon et al. *Nature* 366: 461-464 (1993); and Lee et al. *Curr Biol* 11: 1950-1957 (2001)). In *C. elegans*, aging involves pleiotropic changes that vary among individuals, and mutations that influence lifespan may affect aging of some tissues more than others (Garigan et al. *Genetics* 161: 1101-1112 (2002); and Herndon et al. *Nature* 419: 808-814 (2002). Just before death the anterior intestine and posterior pharynx degenerated more frequently in skn-1 animals than wild type (data not shown), a finding that may reflect aging but does not exclude the possibility of an additional defect. At one week after hatching, small cavities and apparent yolk droplets appeared in the heads of many skn-1 but not wild type animals (data not shown). These changes in the head region are typical of aging *C. elegans* (Garigan et al. *Genetics* 161: 1101-1112 (2002); Herndon et al. *Nature* 419: 808-814), suggesting that skn-1 mutants age prematurely. Some mechanisms that regulate *C. elegans* lifespan have been shown to influence lifespan in higher metazoans (Clancy et al. *Science* 292: 104-106 (2001); Finch et al. *Annu Rev Genomics Nature* 421: 182-187 (2003)). The observation that normal *C. elegans* longevity requires skn-1 is consistent with other associations between oxidative stress resistance and lifespan, and suggests that the conserved oxidative stress resistance pathway regulated by SKN-1 might influence longevity in other species.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for determining whether a test compound is a candidate SKiNhead 1 (SKN-1)-mediated oxidative stress response-activating compound, comprising:

(a) providing a first nematode capable of expressing a SKN-1 polypeptide and containing at least one reporter transgene comprising:

(i) an oxidative stress resistance gene promoter, wherein the promoter comprises a SKN-1 binding site and is effective at directing SKN-1-induced gene expression, and (ii) a reporter gene operably linked to the promoter;

(b) treating the first nematode with the test compound; and (c) determining whether expression of the reporter transgene is increased in the first treated nematode compared to a control nematode not treated with the test compound, wherein increased expression of the reporter transgene in the first treated nematode compared to the control nematode indicates that the test compound is a candidate SKN-1-mediated oxidative stress response-activating compound.

2. The method of claim 1, further comprising determining whether the candidate compound enhances SKN-1-mediated expression of an oxidative stress resistance gene in a cell.

3. A method for determining whether a test compound is a candidate SKN-1-mediated oxidative stress response-inhibiting compound, comprising:

(a) providing a first nematode capable of expressing a SKN-1 polypeptide and containing at least one reporter transgene comprising:

(i) an oxidative stress resistance gene promoter, wherein the promoter comprises a SKN-1 binding site and is effective at directing SKN-1-induced gene expression, and (ii) a reporter gene operably linked to the promoter;

(b) treating the first nematode with the test compound;

(c) before, during, or after step (b), subjecting the nematode to conditions that activate the SKN-1-mediated oxidative stress response in the absence of the test compound; and (d) determining whether expression of the reporter transgene is decreased or unchanged in the first treated nematode compared to a control nematode also subjected to conditions that activate SKN-1-mediated oxidative stress response but not treated with the test compound, wherein decreased or unchanged expression of the reporter transgene in the first treated nematode indicates that the test compound is a candidate SKN-1-mediated oxidative stress response-inhibiting compound.

4. The method of claim 3, further comprising determining whether the candidate compound is an inhibitor of SKN-1-mediated expression of an oxidative stress resistance gene in a cell.

5. The method of claim 1, wherein the promoter is a promoter of a gene encoding a protein selected from the group consisting of: γ-glutamine cysteine synthase heavy chain, glutathione synthetase, NADH quinone oxidoreductase, superoxide dismutase, catalase, and glutathione S-transferase.

6. The method of claim 1, wherein the reporter gene is a gene encoding a protein selected from the group consisting of: green fluorescent protein, chloramphenicol acetyl transferase, β glucuronidase, and luciferase.

7. The method of claim 1, wherein the nematode in step (a) is *Caenorhabditis elegans.*

8. The method of claim 1, wherein the control nematode is the test nematode before being contacted with the test compound.

9. The method of claim 3, wherein the control nematode is the test nematode subjected to conditions that activate the SKN-1-mediated oxidative stress response before being contacted with the test compound.

10. The method of claim 1, wherein the control nematode is a second nematode, not contacted with the test compound.

11. The method of claim 3, wherein the control nematode is a second nematode, subjected to the same conditions that activate the SKN-1-mediated oxidative stress response, in the absence of the test compound.

12. The method of claim 3, wherein the nematode in step (a) is *Caenorhabditis elegans.*

13. The method of claim 1, further comprising determining whether the compound increases NF-E2-related factor 1 (Nrf1)- or Nrf2 mediated expression of an oxidative stress resistance gene in an isolated mammalian cell, as compared to an isolated control cell.

14. The method of claim 3, further comprising determining whether the compound decreases Nrf1- or Nrf2-mediated expression of an oxidative stress resistance gene in an isolated mammalian cell, as compared to an isolated control cell.

* * * * *

UNITED STATES PATENT AND TRADEMARK OFFICE

CERTIFICATE OF CORRECTION

PATENT NO. : 7,572,949 B2
APPLICATION NO. : 10/560563
DATED : August 11, 2009
INVENTOR(S) : Blackwell et al.

It is certified that error appears in the above-identified patent and that said Letters Patent is hereby corrected as shown below:

On title page, Column 2 (“Other Publications”), line 30, delete “Caenohabditis” and insert --Caenorhabditis--;

At Column 118, line 18, in Claim 13, delete “Nrf2 mediated” and insert --Nrf2-mediated--.

Signed and Sealed this

Seventeenth Day of November, 2009

David J. Kappos
*Director of the United States Patent and Trademark Office*

UNITED STATES PATENT AND TRADEMARK OFFICE

CERTIFICATE OF CORRECTION

PATENT NO. : 7,572,949 B2
APPLICATION NO. : 10/560563
DATED : August 11, 2009
INVENTOR(S) : Blackwell et al.

It is certified that error appears in the above-identified patent and that said Letters Patent is hereby corrected as shown below:

On the Title page,

[*] Notice: Subject to any disclaimer, the term of this patent is extended or adjusted under 35 U.S.C. 154(b) by 150 days.

Delete the phrase “by 150 days” and insert -- by 391 days --

Signed and Sealed this

Twenty-second Day of June, 2010

David J. Kappos
*Director of the United States Patent and Trademark Office*

SEQUENCE LISTING

<160> NUMBER OF SEQ ID NOS: 57

<210> SEQ ID NO 1
<211> LENGTH: 85
<212> TYPE: PRT
<213> ORGANISM: Caenorhabditis elegans

<400> SEQUENCE: 1

```
Ala Ser Gly Gln Arg Lys Arg Gly Arg Gln Ser Lys Asp Glu Gln Leu
1               5                   10                  15

Ala Ser Asp Asn Glu Leu Pro Val Ser Ala Phe Gln Ile Ser Glu Met
            20                  25                  30

Ser Leu Ser Glu Leu Gln Gln Val Leu Lys Asn Glu Ser Leu Ser Glu
        35                  40                  45

Tyr Gln Arg Gln Leu Ile Arg Lys Ile Arg Arg Arg Gly Lys Asn Lys
    50                  55                  60

Val Ala Ala Arg Thr Cys Arg Gln Arg Arg Thr Asp Arg His Asp Lys
65                  70                  75                  80

Met Ser His Tyr Ile
                85
```

<210> SEQ ID NO 2
<211> LENGTH: 533
<212> TYPE: PRT
<213> ORGANISM: Caenorhabditis elegans

<400> SEQUENCE: 2

```
Met Tyr Thr Asp Ser Asn Asn Arg Asn Phe Asp Glu Val Asn His Gln
1               5                   10                  15

His Gln Gln Glu Gln Asp Phe Asn Gly Gln Ser Lys Tyr Asp Tyr Pro
            20                  25                  30

Gln Phe Asn Arg Pro Met Gly Leu Arg Trp Arg Asp Asp Gln Arg Met
        35                  40                  45

Met Glu Tyr Phe Met Ser Asn Gly Pro Val Glu Thr Val Pro Val Met
    50                  55                  60

Pro Ile Leu Thr Glu His Pro Pro Ala Ser Pro Phe Gly Arg Gly Pro
65                  70                  75                  80

Ser Thr Glu Arg Pro Thr Thr Ser Ser Arg Tyr Glu Tyr Ser Ser Pro
                85                  90                  95

Ser Leu Glu Asp Ile Asp Leu Ile Asp Val Leu Trp Arg Ser Asp Ile
            100                 105                 110

Ala Gly Glu Lys Gly Thr Arg Gln Val Ala Pro Ala Asp Gln Tyr Glu
        115                 120                 125

Cys Asp Leu Gln Thr Leu Thr Glu Lys Ser Thr Val Ala Pro Leu Thr
    130                 135                 140

Ala Glu Glu Asn Ala Arg Tyr Glu Asp Leu Ser Lys Gly Phe Tyr Asn
145                 150                 155                 160

Gly Phe Phe Glu Ser Phe Asn Asn Asn Gln Tyr Gln Gln Lys His Gln
                165                 170                 175

Gln Gln Gln Arg Glu Gln Ile Lys Thr Pro Thr Leu Glu His Pro Thr
            180                 185                 190

Gln Lys Ala Glu Leu Glu Asp Asp Leu Phe Asp Glu Asp Leu Ala Gln
        195                 200                 205

Leu Phe Glu Asp Val Ser Arg Glu Glu Gly Gln Leu Asn Gln Leu Phe
    210                 215                 220
```

-continued

```
Asp Asn Lys Gln Gln His Pro Val Ile Asn Asn Val Ser Leu Ser Glu
225                 230                 235                 240

Gly Ile Val Tyr Asn Gln Ala Asn Leu Thr Glu Met Gln Glu Met Arg
                245                 250                 255

Asp Ser Cys Asn Gln Val Ser Ile Ser Thr Ile Pro Thr Thr Ser Thr
            260                 265                 270

Ala Gln Pro Glu Thr Leu Phe Asn Val Thr Asp Ser Gln Thr Val Glu
        275                 280                 285

Gln Trp Leu Pro Thr Glu Val Val Pro Asn Asp Val Phe Pro Thr Ser
    290                 295                 300

Asn Tyr Ala Tyr Ile Gly Met Gln Asn Asp Ser Leu Gln Ala Val Val
305                 310                 315                 320

Ser Asn Gly Gln Ile Asp Tyr Asp His Ser Tyr Gln Ser Thr Gly Gln
                325                 330                 335

Thr Pro Leu Ser Pro Leu Ile Ile Gly Ser Ser Gly Arg Gln Gln Gln
            340                 345                 350

Thr Gln Thr Ser Pro Gly Ser Val Thr Val Thr Ala Thr Ala Thr Gln
        355                 360                 365

Ser Leu Phe Asp Pro Tyr His Ser Gln Arg His Ser Phe Ser Asp Cys
    370                 375                 380

Thr Thr Asp Ser Ser Ser Thr Cys Ser Arg Leu Ser Ser Glu Ser Pro
385                 390                 395                 400

Arg Tyr Thr Ser Glu Ser Ser Thr Gly Thr His Glu Ser Arg Phe Tyr
                405                 410                 415

Gly Lys Leu Ala Pro Ser Ser Gly Ser Arg Tyr Gln Arg Ser Ser Ser
            420                 425                 430

Pro Arg Ser Ser Gln Ser Ser Ile Lys Ile Ala Arg Val Val Pro Leu
        435                 440                 445

Ala Ser Gly Gln Arg Lys Arg Gly Arg Gln Ser Lys Asp Glu Gln Leu
    450                 455                 460

Ala Ser Asp Asn Glu Leu Pro Val Ser Ala Phe Gln Ile Ser Glu Met
465                 470                 475                 480

Ser Leu Ser Glu Leu Gln Gln Val Leu Lys Asn Glu Ser Leu Ser Glu
                485                 490                 495

Tyr Gln Arg Gln Leu Ile Arg Lys Ile Arg Arg Arg Gly Lys Asn Lys
            500                 505                 510

Val Ala Ala Arg Thr Cys Arg Gln Arg Arg Thr Asp Arg His Asp Lys
        515                 520                 525

Met Ser His Tyr Ile
    530
```

<210> SEQ ID NO 3
<211> LENGTH: 1602
<212> TYPE: DNA
<213> ORGANISM: Caenorhabditis elegans

<400> SEQUENCE: 3

```
atgtacacgg acagcaataa taggaacttt gatgaagtca accatcagca tcaacaagaa      60

caagatttca atggccaatc caaatatgat tatccacaat tcaaccgtcc aatgggtctc     120

cgttggcgtg atgatcaacg gatgatggag tatttcatgt cgaatggtcc agtagaaact     180

gttccagtta tgccaatact caccgagcat ccaccagcat ctccattcgg tagaggacca     240

tctacagaac gtccaaccac atcatctcga tacgagtaca gttcgccttc tctcgaggat     300
```

-continued

```
atcgacttga ttgatgtgct atggagaagt gatattgctg gagagaaggg cacacgacaa     360

gtggctcctg ctgatcagta cgaatgtgat ttgcagacgt tgacagagaa atcgacagta     420

gcgccactca ctgccgaaga gaatgctcga tatgaagatc tttcgaaagg attctataat     480

ggattcttcg agtcgttcaa taacaatcaa tatcagcaga aacatcagca acaacaacga     540

gaacaaataa agacaccaac tcttgaacat ccaactcaaa aagccgaatt ggaagatgat     600

ctgtttgatg aagatcttgc tcagcttttc gaggatgttt caagagaaga aggacaattg     660

aatcaacttt ttgataataa gcaacaacat ccagttatca ataatgtttc tctgtcggaa     720

ggaattgttt ataatcaggc aaatttgacc gagatgcaag agatgcgtga ttcctgcaat     780

caagtttcca tttcaacaat tccaacaaca tcgactgctc aaccagagac tttgttcaat     840

gtaaccgatt cacagactgt cgaacagtgg cttccaacag aagttgtacc aaacgatgtg     900

ttcccaacat ccaactacgc ctacattgga atgcaaaacg acagtcttca agcagttgta     960

tcaaatggac agattgacta tgatcattcc tatcaatcca ctggtcagac tccactgtct    1020

cctctcatca ttggatcttc aggacgtcaa cagcagactc aaacgagccc aggaagcgtc    1080

acagtgactg caacagctac tcaatcgttg ttcgatccat atcactcaca gagacactcg    1140

tttagtgatt gcactactga ttcgtcatca acgtgctctc gcctctcttc ggaatctcca    1200

cgatacacgt cagagagctc aaccggaact cacgagtctc gtttctacgg aaagttggct    1260

ccatccagtg gatcacgcta ccaacgatca tcgtctccac gttcatcaca atcttcgatt    1320

aagatcgcga gagttgttcc actggccagc ggacaacgga agcgtggacg tcaatccaag    1380

gatgagcagc tcgccagtga caacgagctt ccagtgtcgg cgttccagat ttcggagatg    1440

tcattaagcg agttgcaaca agtgttgaag aacgagagtc tcagcgagta tcaaagacag    1500

ttgattcgca agattcgtcg acgcggaaag aacaaggttg ctgcccgcac ttgccgtcaa    1560

agacgcacgg atcgtcacga caagatgtcc cattacatct ga                       1602
```

```
<210> SEQ ID NO 4
<211> LENGTH: 2615
<212> TYPE: DNA
<213> ORGANISM: Caenorhabditis elegans

<400> SEQUENCE: 4

aatcgttctt cttcttattt tctacagctg atgatgtttg atgaaggttt tattttcctt      60

gctttttcca ccctgttaat attattttcg atattcccaa aaataattcc aaattttcag     120

tccatattca tctggatact tgcaacatca tcactgattt tggtgatcag ttcaccatcg     180

tccaacacct caatccaatc atcgtcatac gatcggatca cgacaaaaca tcttctggac     240

aatatatcac cgacatttag tgagtatgac ttgaaaagtg catctgatca cttttcgagc     300

cgttttgtcg ctagggactt tttaatgaat cagatgtact tttcgaattt tttagagcaa     360

aagcagtagt tgcacttttg aaacttaaat taatatacaa aactatgata tatattttca     420

gaaatgtaca cggacagcaa taataggaac tttgatgaag tcaaccatca gcatcaacaa     480

gaacaagatt tcaatggcca atccaaatat gattatccac aattcaaccg tccaatgggt     540

ctccgttggc gtgatgatca acggatgatg gagtatttca tgtcgaatgg tccagtagaa     600

actgttccag ttatgccaat actcaccgag catccaccag catctccatt cggtagagga     660

ccatctacag aacgtccaac cacatcatct cgatacgagt acagttcgcc ttctctcgag     720

gatatcgact tgattgatgt gctatggaga agtgatattg ctggagagaa gggcacacga     780

caagtggctc ctgctgatca gtacgaatgt gatttgcaga cgttgacaga gaaatcgaca     840
```

-continued

```
gtagcgccac tcactgccga agagaatgct cgatatgaag atctttcgaa aggattctat    900

aatggattct tcgagtcgtt caataacaat caatatcagc agaaacatca gcaacaacaa    960

cgagaacaaa taaagacacc aactcttgaa catccaactc aaaaagccga attggaagat   1020

gatctgtttg atgaagatct tgctcagctt ttcgaggatg tttcaagaga agaaggacaa   1080

ttgaatcaac tttttgataa taagcaacaa catccagtta tcaataatgt ttctctgtcg   1140

gaaggaattg tttataatca ggcaaatttg accgagatgc aagagatgcg tgattcctgc   1200

aatcaagttt ccatttcaac aattccaaca acatcgactg ctcaaccaga gactttgttc   1260

aatgtaaccg attcacagac tgtcgaacag tggcttccaa cagaagttgt accaaacgat   1320

gtgttcccaa catccaacta cgcctacatt ggaatgcaaa acgacagtct tcaagcagtt   1380

gtatcaaatg gacagattga ctatgatcat tcctatcaat ccactggtca gactccactg   1440

tctcctctca tcattggatc ttcaggacgt caacagcaga ctcaaacgag cccaggaagc   1500

gtcacagtga ctgcaacagc tactcaatcg ttgttcgatc catatcactc acagagacac   1560

tcgtttagtg attgcactac tgattcgtca tcaacgtgct ctcgcctctc ttcggaatct   1620

ccacgataca cgtcagagag ctcaaccgga actcacgagt ctcgtttcta cggaaagttg   1680

gctccatcca gtggatcacg ctaccaacga tcatcgtctc cacgttcatc acaatcttcg   1740

attaagatcg cgagagttgt tccactggcc agcggacaac ggaagcgtgg acgtcaatcc   1800

aaggatgagc agctcgccag tgacaacgag cttccagtgt cggcgttcca gatttcggag   1860

atgtcattaa gcgagttgca acaagtgttg aagaacgaga gtctcagcga gtatcaaaga   1920

cagttgattc gcaagattcg tcgacgcgga aagaacaagg ttgctgcccg cacttgccgt   1980

caaagacgca cggatcgtca cgacaagatg tcccattaca tctgagaagc cctcttttat   2040

cacataaaat ctcggtcgaa accttattaa agccacataa ttaaagataa ttaattccgc   2100

cacaataatc gttttttct tctttgccgt gtctcatttc attttgatct actctttcct   2160

cccttcggat tctttgattt cccagtgaaa tacctcaccc acttcaatcc ccacaaagtg   2220

agcaacccct atcttgcaac agttttatca tctcttcatc atacccagtt tgataattta   2280

ttatctgatc cccatcccct tgtcgcctct cattagtatc ctagtttttc atttgagccc   2340

ggagctcaga ctacatctcc gaatcatcat acaaatagat agaaacgggt ctcgtgacga   2400

aagaatacgt gcaccacacg acccccccat cctgttcacc cccatacacc tgaaaaatat   2460

gatctttaca gttatttcta ttatatcctc aaatctctcg taatatcgta tcaatttcct   2520

cttctttttt gtcattttca atttttctca aatttctcag atctattctt tttcttgtat   2580

ttttggaact tgtatccctc ctccatcccc agact                              2615
```

<210> SEQ ID NO 5
<211> LENGTH: 23
<212> TYPE: PRT
<213> ORGANISM: Caenorhabditis elegans

<400> SEQUENCE: 5

```
Phe Ser Asp Cys Thr Thr Asp Ser Ser Ser Thr Cys Ser Arg Leu Ser
1               5                   10                  15

Ser Glu Ser Pro Arg Tyr Thr
            20
```

<210> SEQ ID NO 6
<211> LENGTH: 933
<212> TYPE: DNA

-continued

<213> ORGANISM: Caenorhabditis elegans

<400> SEQUENCE: 6
atgtcacttc catctgattt tgcctcctct cttctggcat cctctaccac caccaacacc 60
accaacaccg ctccagcagc tgtcaactct tttgacgaac aagaagaaga atccaagaag 120
atactgaaca tgtaccttca aatgttcaat caacaacagg tggatcaaca cggccatcat 180
caccaacatc catacgccta ttcaggagtc tcgagcactt ttgacagagt gttcccaaca 240
tccaactacg cctacattgg aatgcaaaac gacagtcttc aagcagttgt atcaaatgga 300
cagattgact atgatcattc ctatcaatcc actggtcaga ctccactgtc tcctctcatc 360
attggatctt caggacgtca acagcagact caaacgagcc caggaagcgt cacagtgact 420
gcaacagcta ctcaatcgtt gttcgatcca tatcactcac agagacactc gtttagtgat 480
tgcactactg attcgtcatc aacgtgctct cgcctctctt cggaatctcc acgatacacg 540
tcagagagct caaccggaac tcacgagtct cgtttctacg gaaagttggc tccatccagt 600
ggatcacgct accaacgatc atcgtctcca cgttcatcac aatcttcgat taagatcgcg 660
agagttgttc cactggccag cggacaacgg aagcgtggac gtcaatccaa ggatgagcag 720
ctcgccagtg acaacgagct tccagtgtcg gcgttccaga tttcggagat gtcattaagc 780
gagttgcaac aagtgttgaa gaacgagagt ctcagcgagt atcaaagaca gttgattcgc 840
aagattcgtc gacgcggaaa gaacaaggtt gctgcccgca cttgccgtca aagacgcacg 900
gatcgtcacg acaagatgtc ccattacatc tga 933

<210> SEQ ID NO 7
<211> LENGTH: 310
<212> TYPE: PRT
<213> ORGANISM: Caenorhabditis elegans

<400> SEQUENCE: 7

Met Ser Leu Pro Ser Asp Phe Ala Ser Ser Leu Leu Ala Ser Ser Thr
1 5 10 15

Thr Thr Asn Thr Thr Asn Thr Ala Pro Ala Ala Val Asn Ser Phe Asp
20 25 30

Glu Gln Glu Glu Glu Ser Lys Lys Ile Leu Asn Met Tyr Leu Gln Met
35 40 45

Phe Asn Gln Gln Gln Val Asp Gln His Gly His His His Gln His Pro
50 55 60

Tyr Ala Tyr Ser Gly Val Ser Ser Thr Phe Asp Arg Val Phe Pro Thr
65 70 75 80

Ser Asn Tyr Ala Tyr Ile Gly Met Gln Asn Asp Ser Leu Gln Ala Val
85 90 95

Val Ser Asn Gly Gln Ile Asp Tyr Asp His Ser Tyr Gln Ser Thr Gly
100 105 110

Gln Thr Pro Leu Ser Pro Leu Ile Ile Gly Ser Ser Gly Arg Gln Gln
115 120 125

Gln Thr Gln Thr Ser Pro Gly Ser Val Thr Val Thr Ala Thr Ala Thr
130 135 140

Gln Ser Leu Phe Asp Pro Tyr His Ser Gln Arg His Ser Phe Ser Asp
145 150 155 160

Cys Thr Thr Asp Ser Ser Ser Thr Cys Ser Arg Leu Ser Ser Glu Ser
165 170 175

Pro Arg Tyr Thr Ser Glu Ser Ser Thr Gly Thr His Glu Ser Arg Phe
180 185 190

-continued

```
Tyr Gly Lys Leu Ala Pro Ser Ser Gly Ser Arg Tyr Gln Arg Ser Ser
        195                 200                 205

Ser Pro Arg Ser Ser Gln Ser Ser Ile Lys Ile Ala Arg Val Val Pro
    210                 215                 220

Leu Ala Ser Gly Gln Arg Lys Arg Gly Arg Gln Ser Lys Asp Glu Gln
225                 230                 235                 240

Leu Ala Ser Asp Asn Glu Leu Pro Val Ser Ala Phe Gln Ile Ser Glu
                245                 250                 255

Met Ser Leu Ser Glu Leu Gln Gln Val Leu Lys Asn Glu Ser Leu Ser
            260                 265                 270

Glu Tyr Gln Arg Gln Leu Ile Arg Lys Ile Arg Arg Arg Gly Lys Asn
        275                 280                 285

Lys Val Ala Ala Arg Thr Cys Arg Gln Arg Arg Thr Asp Arg His Asp
    290                 295                 300

Lys Met Ser His Tyr Ile
305                 310


<210> SEQ ID NO 8
<211> LENGTH: 1590
<212> TYPE: DNA
<213> ORGANISM: Caenorhabditis elegans

<400> SEQUENCE: 8

gaatgtcact tccatctgat tttgcctcct ctcttctggc atcctctacc accaccaaca     60

ccaccaacac cgctccagca gctgtcaact cttttgacga acaagaagaa gaatccaaga    120

agatactgaa catgtacctt caaatgttca atcaacaaca ggtggatcaa cacggccatc    180

atcaccaaca tccatacgcc tattcaggag tctcgagcac ttttgacaga gtgttcccaa    240

catccaacta cgcctacatt ggaatgcaaa acgacagtct tcaagcagtt gtatcaaatg    300

gacagattga ctatgatcat tcctatcaat ccactggtca gactccactg tctcctctca    360

tcattggatc ttcaggacgt caacagcaga ctcaaacgag cccaggaagc gtcacagtga    420

ctgcaacagc tactcaatcg ttgttcgatc catatcactc acagagacac tcgtttagtg    480

attgcactac tgattcgtca tcaacgtgct ctcgcctctc ttcggaatct ccacgataca    540

cgtcagagag ctcaaccgga actcacgagt ctcgtttcta cggaaagttg gctccatcca    600

gtggatcacg ctaccaacga tcatcgtctc cacgttcatc acaatcttcg attaagatcg    660

cgagagttgt tccactggcc agcggacaac ggaagcgtgg acgtcaatcc aaggatgagc    720

agctcgccag tgacaacgag cttccagtgt cggcgttcca gatttcggag atgtcattaa    780

gcgagttgca acaagtgttg aagaacgaga gtctcagcga gtatcaaaga cagttgattc    840

gcaagattcg tcgacgcgga aagaacaagg ttgctgcccg cacttgccgt caaagacgca    900

cggatcgtca cgacaagatg tcccattaca tctgagaagc cctcttttat cacataaaat    960

ctcggtcgaa accttattaa agccacataa ttaaagataa ttaattccgc cacaataatc   1020

gttttttct tctttgccgt gtctcatttc attttgatct actctttcct cccttcggat   1080

tctttgattt cccagtgaaa tacctcaccc acttcaatcc ccacaaagtg agcaacccct   1140

atcttgcaac agttttatca tctcttcatc atacccagtt tgataattta ttatctgatc   1200

cccatcccct tgtcgcctct cattagtatc ctagtttttc atttgagccc ggagctcaga   1260

ctacatctcc gaatcatcat acaaatagat agaaacgggt ctcgtgacga aagaatacgt   1320

gcaccacacg acccccccat cctgttcacc cccatacacc tgaaaaatat gatctttaca   1380
```

-continued

```
gttatttcta ttatatcctc aaatctctcg taatatcgta tcaatttcct cttctttttt   1440

gtcattttca atttttctca aatttctcag atctattctt tttcttgtat ttttggaact   1500

tgtatccctc ctccatcccc agacttcccc ttcccagtta ctcttgtaca ttttcatata   1560

tgtccatata tcgtttgaat ctctcattta                                     1590


<210> SEQ ID NO 9
<211> LENGTH: 1872
<212> TYPE: DNA
<213> ORGANISM: Caenorhabditis elegans

<400> SEQUENCE: 9

atgggcggtt catcacgccg tcagcgaagt acgtcggcga cgagacgaga cgataaacga     60

agacgaagac agtgcttctc ttcggtagcc gacgacgaag aagagacgac gtcaatttat    120

ggagtgtcgt ccatattcat ctggatactt gcaacatcat cactgatttt ggtgatcagt    180

tcaccatcgt ccaacacctc aatccaatca tcgtcatacg atcggatcac gacaaaacat    240

cttctggaca atatatcacc gacatttaaa atgtacacgg acagcaataa taggaacttt    300

gatgaagtca accatcagca tcaacaagaa caagatttca atggccaatc caaatatgat    360

tatccacaat tcaaccgtcc aatgggtctc cgttggcgtg atgatcaacg gatgatggag    420

tatttcatgt cgaatggtcc agtagaaact gttccagtta tgccaatact caccgagcat    480

ccaccagcat ctccattcgg tagaggacca tctacagaac gtccaaccac atcatctcga    540

tacgagtaca gttcgccttc tctcgaggat atcgacttga ttgatgtgct atggagaagt    600

gatattgctg gagagaaggg cacacgacaa gtggctcctg ctgatcagta cgaatgtgat    660

ttgcagacgt tgacagagaa atcgacagta gcgccactca ctgccgaaga gaatgctcga    720

tatgaagatc tttcgaaagg attctataat ggattcttcg agtcgttcaa taacaatcaa    780

tatcagcaga aacatcagca acaacaacga gaacaaataa agacaccaac tcttgaacat    840

ccaactcaaa aagccgaatt ggaagatgat ctgtttgatg aagatcttgc tcagcttttc    900

gaggatgttt caagagaaga aggacaattg aatcaacttt ttgataataa gcaacaacat    960

ccagttatca ataatgtttc tctgtcggaa ggaattgttt ataatcaggc aaatttgacc   1020

gagatgcaag agatgcgtga ttcctgcaat caagtttcca tttcaacaat tccaacaaca   1080

tcgactgctc aaccagagac tttgttcaat gtaaccgatt cacagactgt cgaacagtgg   1140

cttccaacag aagttgtacc aaacgatgtg ttcccaacat ccaactacgc ctacattgga   1200

atgcaaaacg acagtcttca agcagttgta tcaaatggac agattgacta tgatcattcc   1260

tatcaatcca ctggtcagac tccactgtct cctctcatca ttggatcttc aggacgtcaa   1320

cagcagactc aaacgagccc aggaagcgtc acagtgactg caacagctac tcaatcgttg   1380

ttcgatccat atcactcaca gagacactcg tttagtgatt gcactactga ttcgtcatca   1440

acgtgctctc gcctctcttc ggaatctcca cgatacacgt cagagagctc aaccggaact   1500

cacgagtctc gtttctacgg aaagttggct ccatccagtg gatcacgcta ccaacgatca   1560

tcgtctccac gttcatcaca atcttcgatt aagatcgcga gagttgttcc actggccagc   1620

ggacaacgga agcgtggacg tcaatccaag gatgagcagc tcgccagtga caacgagctt   1680

ccagtgtcgg cgttccagat ttcggagatg tcattaagcg agttgcaaca agtgttgaag   1740

aacgagagtc tcagcgagta tcaaagacag ttgattcgca agattcgtcg acgcggaaag   1800

aacaaggttg ctgcccgcac ttgccgtcaa agacgcacgg atcgtcacga caagatgtcc   1860

cattacatct ga                                                       1872
```

-continued

<210> SEQ ID NO 10
<211> LENGTH: 623
<212> TYPE: PRT
<213> ORGANISM: Caenorhabditis elegans

<400> SEQUENCE: 10

```
Met Gly Gly Ser Ser Arg Arg Gln Arg Ser Thr Ser Ala Thr Arg Arg
1               5                   10                  15

Asp Asp Lys Arg Arg Arg Arg Gln Cys Phe Ser Ser Val Ala Asp Asp
            20                  25                  30

Glu Glu Glu Thr Thr Ser Ile Tyr Gly Val Ser Ser Ile Phe Ile Trp
        35                  40                  45

Ile Leu Ala Thr Ser Ser Leu Ile Leu Val Ile Ser Ser Pro Ser Ser
    50                  55                  60

Asn Thr Ser Ile Gln Ser Ser Ser Tyr Asp Arg Ile Thr Thr Lys His
65                  70                  75                  80

Leu Leu Asp Asn Ile Ser Pro Thr Phe Lys Met Tyr Thr Asp Ser Asn
                85                  90                  95

Asn Arg Asn Phe Asp Glu Val Asn His Gln His Gln Gln Glu Gln Asp
            100                 105                 110

Phe Asn Gly Gln Ser Lys Tyr Asp Tyr Pro Gln Phe Asn Arg Pro Met
        115                 120                 125

Gly Leu Arg Trp Arg Asp Asp Gln Arg Met Met Glu Tyr Phe Met Ser
    130                 135                 140

Asn Gly Pro Val Glu Thr Val Pro Val Met Pro Ile Leu Thr Glu His
145                 150                 155                 160

Pro Pro Ala Ser Pro Phe Gly Arg Gly Pro Ser Thr Glu Arg Pro Thr
                165                 170                 175

Thr Ser Ser Arg Tyr Glu Tyr Ser Ser Pro Ser Leu Glu Asp Ile Asp
            180                 185                 190

Leu Ile Asp Val Leu Trp Arg Ser Asp Ile Ala Gly Glu Lys Gly Thr
        195                 200                 205

Arg Gln Val Ala Pro Ala Asp Gln Tyr Glu Cys Asp Leu Gln Thr Leu
    210                 215                 220

Thr Glu Lys Ser Thr Val Ala Pro Leu Thr Ala Glu Glu Asn Ala Arg
225                 230                 235                 240

Tyr Glu Asp Leu Ser Lys Gly Phe Tyr Asn Gly Phe Phe Glu Ser Phe
                245                 250                 255

Asn Asn Asn Gln Tyr Gln Gln Lys His Gln Gln Gln Gln Arg Glu Gln
            260                 265                 270

Ile Lys Thr Pro Thr Leu Glu His Pro Thr Gln Lys Ala Glu Leu Glu
        275                 280                 285

Asp Asp Leu Phe Asp Glu Asp Leu Ala Gln Leu Phe Glu Asp Val Ser
    290                 295                 300

Arg Glu Glu Gly Gln Leu Asn Gln Leu Phe Asp Asn Lys Gln Gln His
305                 310                 315                 320

Pro Val Ile Asn Asn Val Ser Leu Ser Glu Gly Ile Val Tyr Asn Gln
                325                 330                 335

Ala Asn Leu Thr Glu Met Gln Glu Met Arg Asp Ser Cys Asn Gln Val
            340                 345                 350

Ser Ile Ser Thr Ile Pro Thr Thr Ser Thr Ala Gln Pro Glu Thr Leu
        355                 360                 365

Phe Asn Val Thr Asp Ser Gln Thr Val Glu Gln Trp Leu Pro Thr Glu
```

-continued

```
    370                 375                 380

Val Val Pro Asn Asp Val Phe Pro Thr Ser Asn Tyr Ala Tyr Ile Gly
385                 390                 395                 400

Met Gln Asn Asp Ser Leu Gln Ala Val Val Ser Asn Gly Gln Ile Asp
                405                 410                 415

Tyr Asp His Ser Tyr Gln Ser Thr Gly Gln Thr Pro Leu Ser Pro Leu
            420                 425                 430

Ile Ile Gly Ser Ser Gly Arg Gln Gln Gln Thr Gln Thr Ser Pro Gly
        435                 440                 445

Ser Val Thr Val Thr Ala Thr Ala Thr Gln Ser Leu Phe Asp Pro Tyr
    450                 455                 460

His Ser Gln Arg His Ser Phe Ser Asp Cys Thr Thr Asp Ser Ser Ser
465                 470                 475                 480

Thr Cys Ser Arg Leu Ser Ser Glu Ser Pro Arg Tyr Thr Ser Glu Ser
                485                 490                 495

Ser Thr Gly Thr His Glu Ser Arg Phe Tyr Gly Lys Leu Ala Pro Ser
            500                 505                 510

Ser Gly Ser Arg Tyr Gln Arg Ser Ser Ser Pro Arg Ser Ser Gln Ser
        515                 520                 525

Ser Ile Lys Ile Ala Arg Val Val Pro Leu Ala Ser Gly Gln Arg Lys
    530                 535                 540

Arg Gly Arg Gln Ser Lys Asp Glu Gln Leu Ala Ser Asp Asn Glu Leu
545                 550                 555                 560

Pro Val Ser Ala Phe Gln Ile Ser Glu Met Ser Leu Ser Glu Leu Gln
                565                 570                 575

Gln Val Leu Lys Asn Glu Ser Leu Ser Glu Tyr Gln Arg Gln Leu Ile
            580                 585                 590

Arg Lys Ile Arg Arg Arg Gly Lys Asn Lys Val Ala Ala Arg Thr Cys
        595                 600                 605

Arg Gln Arg Arg Thr Asp Arg His Asp Lys Met Ser His Tyr Ile
    610                 615                 620
```

<210> SEQ ID NO 11
<211> LENGTH: 23
<212> TYPE: PRT
<213> ORGANISM: Caenorhabditis elegans

<400> SEQUENCE: 11

```
Asp Cys Thr Thr Asp Ser Ser Ser Thr Cys Ser Arg Leu Ser Ser Glu
1               5                   10                  15

Ser Pro Arg Tyr Thr Ser Glu
            20
```

<210> SEQ ID NO 12
<211> LENGTH: 2549
<212> TYPE: DNA
<213> ORGANISM: Caenorhabditis elegans

<400> SEQUENCE: 12

```
atgggcggtt catcacgccg tcagcgaagt acgtcggcga cgagacgaga cgataaacga      60

agacgaagac agtgcttctc ttcggtagcc gacgacgaag aagagacgac gtcaatttat     120

ggagtgtcgt ccatattcat ctggatactt gcaacatcat cactgatttt ggtgatcagt     180

tcaccatcgt ccaacacctc aatccaatca tcgtcatacg atcggatcac gacaaaaacat     240

cttctggaca atatatcacc gacatttaaa atgtacacgg acagcaataa taggaacttt     300
```

-continued

```
gatgaagtca accatcagca tcaacaagaa caagatttca atggccaatc caaatatgat    360
tatccacaat tcaaccgtcc aatgggtctc cgttggcgtg atgatcaacg gatgatggag    420
tatttcatgt cgaatggtcc agtagaaact gttccagtta tgccaatact caccgagcat    480
ccaccagcat ctccattcgg tagaggacca tctacagaac gtccaaccac atcatctcga    540
tacgagtaca gttcgccttc tctcgaggat atcgacttga ttgatgtgct atggagaagt    600
gatattgctg gagagaaggg cacacgacaa gtggctcctg ctgatcagta cgaatgtgat    660
ttgcagacgt tgacagagaa atcgacagta gcgccactca ctgccgaaga gaatgctcga    720
tatgaagatc tttcgaaagg attctataat ggattcttcg agtcgttcaa taacaatcaa    780
tatcagcaga aacatcagca acaacaacga gaacaaataa agacaccaac tcttgaacat    840
ccaactcaaa aagccgaatt ggaagatgat ctgtttgatg aagatcttgc tcagcttttc    900
gaggatgttt caagagaaga aggacaattg aatcaacttt ttgataataa gcaacaacat    960
ccagttatca ataatgtttc tctgtcggaa ggaattgttt ataatcaggc aaatttgacc   1020
gagatgcaag agatgcgtga ttcctgcaat caagtttcca tttcaacaat tccaacaaca   1080
tcgactgctc aaccagagac tttgttcaat gtaaccgatt cacagactgt cgaacagtgg   1140
cttccaacag aagttgtacc aaacgatgtg ttcccaacat ccaactacgc ctacattgga   1200
atgcaaaacg acagtcttca agcagttgta tcaaatggac agattgacta tgatcattcc   1260
tatcaatcca ctggtcagac tccactgtct cctctcatca ttggatcttc aggacgtcaa   1320
cagcagactc aaacgagccc aggaagcgtc acagtgactg caacagctac tcaatcgttg   1380
ttcgatccat atcactcaca gagacactcg tttagtgatt gcactactga ttcgtcatca   1440
acgtgctctc gcctctcttc ggaatctcca cgatacacgt cagagagctc aaccggaact   1500
cacgagtctc gtttctacgg aaagttggct ccatccagtg gatcacgcta ccaacgatca   1560
tcgtctccac gttcatcaca atcttcgatt aagatcgcga gagttgttcc actggccagc   1620
ggacaacgga agcgtggacg tcaatccaag gatgagcagc tcgccagtga caacgagctt   1680
ccagtgtcgg cgttccagat ttcggagatg tcattaagcg agttgcaaca agtgttgaag   1740
aacgagagtc tcagcgagta tcaaagacag ttgattcgca agattcgtcg acgcggaaag   1800
aacaaggttg ctgcccgcac ttgccgtcaa agacgcacgg atcgtcacga caagatgtcc   1860
cattacatct gagaagccct cttttatcac ataaaatctc ggtcgaaacc ttattaaagc   1920
cacataatta aagataatta attccgccac aataatcgtt tttttcttct ttgccgtgtc   1980
tcatttcatt ttgatctact ctttcctccc ttcggattct ttgatttccc agtgaaatac   2040
ctcacccact tcaatcccca caaagtgagc aacccctatc ttgcaacagt tttatcatct   2100
cttcatcata cccagtttga taatttatta tctgatcccc atccccttgt cgcctctcat   2160
tagtatccta gtttttcatt tgagcccgga gctcagacta catctccgaa tcatcataca   2220
aatagataga aacgggtctc gtgacgaaag aatacgtgca ccacacgacc cccccatcct   2280
gttcaccccc atacacctga aaaatatgat ctttacagtt atttctatta tatcctcaaa   2340
tctctcgtaa tatcgtatca atttcctctt cttttttgtc attttcaatt tttctcaaat   2400
ttctcagatc tattcttttt cttgtatttt tggaacttgt atccctcctc catccccaga   2460
cttccccttc ccagttactc ttgtacattt tcatatatgt ccatatatcg tttgaatctc   2520
tcatttatgg aaataaattt gaaaaaatc                                     2549
```

<210> SEQ ID NO 13
<211> LENGTH: 420

-continued

<212> TYPE: PRT
<213> ORGANISM: Homo sapiens

<400> SEQUENCE: 13

Met Ser Gly Arg Pro Arg Thr Thr Ser Phe Ala Glu Ser Cys Lys Pro
1 5 10 15

Val Gln Gln Pro Ser Ala Phe Gly Ser Met Lys Val Ser Arg Asp Lys
20 25 30

Asp Gly Ser Lys Val Thr Thr Val Val Ala Thr Pro Gly Gln Gly Pro
35 40 45

Asp Arg Pro Gln Glu Val Ser Tyr Thr Asp Thr Lys Val Ile Gly Asn
50 55 60

Gly Ser Phe Gly Val Val Tyr Gln Ala Lys Leu Cys Asp Ser Gly Glu
65 70 75 80

Leu Val Ala Ile Lys Lys Val Leu Gln Asp Lys Arg Phe Lys Asn Arg
85 90 95

Glu Leu Gln Ile Met Arg Lys Leu Asp His Cys Asn Ile Val Arg Leu
100 105 110

Arg Tyr Phe Phe Tyr Ser Ser Gly Glu Lys Lys Asp Glu Val Tyr Leu
115 120 125

Asn Leu Val Leu Asp Tyr Val Pro Glu Thr Val Tyr Arg Val Ala Arg
130 135 140

His Tyr Ser Arg Ala Lys Gln Thr Leu Pro Val Ile Tyr Val Lys Leu
145 150 155 160

Tyr Met Tyr Gln Leu Phe Arg Ser Leu Ala Tyr Ile His Ser Phe Gly
165 170 175

Ile Cys His Arg Asp Ile Lys Pro Gln Asn Leu Leu Leu Asp Pro Asp
180 185 190

Thr Ala Val Leu Lys Leu Cys Asp Phe Gly Ser Ala Lys Gln Leu Val
195 200 205

Arg Gly Glu Pro Asn Val Ser Tyr Ile Cys Ser Arg Tyr Tyr Arg Ala
210 215 220

Pro Glu Leu Ile Phe Gly Ala Thr Asp Tyr Thr Ser Ser Ile Asp Val
225 230 235 240

Trp Ser Ala Gly Cys Val Leu Ala Glu Leu Leu Leu Gly Gln Pro Ile
245 250 255

Phe Pro Gly Asp Ser Gly Val Asp Gln Leu Val Glu Ile Ile Lys Val
260 265 270

Leu Gly Thr Pro Thr Arg Glu Gln Ile Arg Glu Met Asn Pro Asn Tyr
275 280 285

Thr Glu Phe Lys Phe Pro Gln Ile Lys Ala His Pro Trp Thr Lys Val
290 295 300

Phe Arg Pro Arg Thr Pro Pro Glu Ala Ile Ala Leu Cys Ser Arg Leu
305 310 315 320

Leu Glu Tyr Thr Pro Thr Ala Arg Leu Thr Pro Leu Glu Ala Cys Ala
325 330 335

His Ser Phe Phe Asp Glu Leu Arg Asp Pro Asn Val Lys Leu Pro Asn
340 345 350

Gly Arg Asp Thr Pro Ala Leu Phe Asn Phe Thr Thr Gln Glu Leu Ser
355 360 365

Ser Asn Pro Pro Leu Ala Thr Ile Leu Ile Pro Pro His Ala Arg Ile
370 375 380

Gln Ala Ala Ala Ser Thr Pro Thr Asn Ala Thr Ala Ala Ser Asp Ala
385 390 395 400

-continued

```
Asn Thr Gly Asp Arg Gly Gln Thr Asn Asn Ala Ala Ser Ala Ser Ala
                405                 410                 415

Ser Asn Ser Thr
            420


<210> SEQ ID NO 14
<211> LENGTH: 483
<212> TYPE: PRT
<213> ORGANISM: Homo sapiens

<400> SEQUENCE: 14

Met Ser Gly Gly Gly Pro Ser Gly Gly Gly Pro Gly Gly Ser Gly Arg
1               5                   10                  15

Ala Arg Thr Ser Ser Phe Ala Glu Pro Gly Gly Gly Gly Gly Gly Gly
            20                  25                  30

Gly Gly Gly Pro Gly Gly Ser Ala Ser Gly Pro Gly Gly Thr Gly Gly
        35                  40                  45

Gly Lys Ala Ser Val Gly Ala Met Gly Gly Gly Val Gly Ala Ser Ser
    50                  55                  60

Ser Gly Gly Gly Pro Gly Gly Ser Gly Gly Gly Gly Ser Gly Gly Pro
65                  70                  75                  80

Gly Ala Gly Thr Ser Phe Pro Pro Pro Gly Val Lys Leu Gly Arg Asp
                85                  90                  95

Ser Gly Lys Val Thr Thr Val Val Ala Thr Leu Gly Gln Gly Pro Glu
            100                 105                 110

Arg Ser Gln Glu Val Ala Tyr Thr Asp Ile Lys Val Ile Gly Asn Gly
        115                 120                 125

Ser Phe Gly Val Val Tyr Gln Ala Arg Leu Ala Glu Thr Arg Glu Leu
    130                 135                 140

Val Ala Ile Lys Lys Val Leu Gln Asp Lys Arg Phe Lys Asn Arg Glu
145                 150                 155                 160

Leu Gln Ile Met Arg Lys Leu Asp His Cys Asn Ile Val Arg Leu Arg
                165                 170                 175

Tyr Phe Phe Tyr Ser Ser Gly Glu Lys Lys Asp Glu Leu Tyr Leu Asn
            180                 185                 190

Leu Val Leu Glu Tyr Val Pro Glu Thr Val Tyr Arg Val Ala Arg His
        195                 200                 205

Phe Thr Lys Ala Lys Leu Thr Ile Pro Ile Leu Tyr Val Lys Val Tyr
    210                 215                 220

Met Tyr Gln Leu Phe Arg Ser Leu Ala Tyr Ile His Ser Gln Gly Val
225                 230                 235                 240

Cys His Arg Asp Ile Lys Pro Gln Asn Leu Leu Val Asp Pro Asp Thr
                245                 250                 255

Ala Val Leu Lys Leu Cys Asp Phe Gly Ser Ala Lys Gln Leu Val Arg
            260                 265                 270

Gly Glu Pro Asn Val Ser Tyr Ile Cys Ser Arg Tyr Tyr Arg Ala Pro
        275                 280                 285

Glu Leu Ile Phe Gly Ala Thr Asp Tyr Thr Ser Ser Ile Asp Val Trp
    290                 295                 300

Ser Ala Gly Cys Val Leu Ala Glu Leu Leu Leu Gly Gln Pro Ile Phe
305                 310                 315                 320

Pro Gly Asp Ser Gly Val Asp Gln Leu Val Glu Ile Ile Lys Val Leu
                325                 330                 335

Gly Thr Pro Thr Arg Glu Gln Ile Arg Glu Met Asn Pro Asn Tyr Thr
```

-continued

```
            340                 345                 350

Glu Phe Lys Phe Pro Gln Ile Lys Ala His Pro Trp Thr Lys Val Phe
        355                 360                 365

Lys Ser Arg Thr Pro Pro Glu Ala Ile Ala Leu Cys Ser Ser Leu Leu
    370                 375                 380

Glu Tyr Thr Pro Ser Ser Arg Leu Ser Pro Leu Glu Ala Cys Ala His
385                 390                 395                 400

Ser Phe Phe Asp Glu Leu Arg Cys Leu Gly Thr Gln Leu Pro Asn Asn
                405                 410                 415

Arg Pro Leu Pro Pro Leu Phe Asn Phe Ser Ala Gly Glu Leu Ser Ile
            420                 425                 430

Gln Pro Ser Leu Asn Ala Ile Leu Ile Pro Pro His Leu Arg Ser Pro
        435                 440                 445

Ala Gly Thr Thr Thr Leu Thr Pro Ser Ser Gln Ala Leu Thr Glu Thr
    450                 455                 460

Pro Thr Ser Ser Asp Trp Gln Ser Thr Asp Ala Thr Pro Thr Leu Thr
465                 470                 475                 480

Asn Ser Ser


<210> SEQ ID NO 15
<211> LENGTH: 420
<212> TYPE: PRT
<213> ORGANISM: Mus musculus

<400> SEQUENCE: 15

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
```

-continued 225 230 235 240

Trp Ser Ala Gly Cys Val Leu Ala Glu Leu Leu Leu Gly Gln Pro Ile
245 250 255

Phe Pro Gly Asp Ser Gly Val Asp Gln Leu Val Glu Ile Ile Lys Val
260 265 270

Leu Gly Thr Pro Thr Arg Glu Gln Ile Arg Glu Met Asn Pro Asn Tyr
275 280 285

Thr Glu Phe Lys Phe Pro Gln Ile Lys Ala His Pro Trp Thr Lys Val
290 295 300

Phe Arg Pro Arg Thr Pro Pro Glu Ala Ile Ala Leu Cys Ser Arg Leu
305 310 315 320

Leu Glu Tyr Thr Pro Thr Ala Arg Leu Thr Pro Leu Glu Ala Cys Ala
325 330 335

His Ser Phe Phe Asp Glu Leu Arg Asp Pro Asn Val Lys Leu Pro Asn
340 345 350

Gly Arg Asp Thr Pro Ala Leu Phe Asn Phe Thr Thr Gln Glu Leu Ser
355 360 365

Ser Asn Pro Pro Leu Ala Thr Ile Leu Ile Pro Pro His Ala Arg Ile
370 375 380

Gln Ala Ala Ala Ser Pro Pro Ala Asn Ala Thr Ala Ala Ser Asp Thr
385 390 395 400

Asn Ala Gly Asp Arg Gly Gln Thr Asn Asn Ala Ala Ser Ala Ser Ala
405 410 415

Ser Asn Ser Thr
420

<210> SEQ ID NO 16
<211> LENGTH: 447
<212> TYPE: PRT
<213> ORGANISM: Mus musculus
<220> FEATURE:
<221> NAME/KEY: VARIANT
<222> LOCATION: 227, 308
<223> OTHER INFORMATION: Xaa = Any Amino Acid

<400> SEQUENCE: 16

Met Ala Ser Thr Thr Ala Met Asp Val Leu Glu Glu Leu Ser Ser Asp
1 5 10 15

Ser Ser Glu Lys Gln Arg Ser Val Asn Ile Leu Asp Ser Phe Val Lys
20 25 30

Asp Met Phe Glu Arg Ile Ala Ser Glu Ala Ser Phe Leu Ala Arg Gln
35 40 45

Ala Arg Asn Ser Thr Ile Asn Ser Arg Glu Ile Gln Thr Ala Ile Arg
50 55 60

Leu Leu Leu Pro Gly Glu Leu Cys Arg Arg Gly Thr Gly Cys Gly Lys
65 70 75 80

Ala Ser Val Trp Ala Met Gly Gly Gly Val Gly Ala Ser Ser Ser Gly
85 90 95

Val Gly Gly Gly Ser Gly Gly Pro Gly Ser Thr Ser Phe Leu Gln Pro
100 105 110

Gly Val Lys Leu Gly His Asp Ser Arg Lys Val Thr Thr Val Val Ala
115 120 125

Thr Val Gly Gln Asp Pro Glu Arg Ser Gln Glu Val Ala Cys Thr Asp
130 135 140

Ile Lys Val Ile Gly Asn Gly Ser Phe Gly Val Val Tyr Gln Glu Trp
145 150 155 160

-continued

```
Leu Ala Asp Thr Arg Glu Leu Val Ala Ile Lys Lys Val Leu Gln Asp
                165                 170                 175

Lys Arg Phe Lys Tyr Arg Glu Leu Gln Ile Met Cys Lys Leu Asp His
            180                 185                 190

Cys Asn Ile Val Arg Leu Gln Tyr Phe Phe Tyr Ser Ser Gly Glu Lys
        195                 200                 205

Lys Asp Asp Leu Tyr Leu Asn Leu Val Leu Glu Tyr Val Pro Glu Thr
    210                 215                 220

Val Tyr Xaa Val Ala Arg His Phe Thr Lys Ala Lys Leu Ile Ile Pro
225                 230                 235                 240

Ile Ile Tyr Val Lys Val Tyr Met Tyr Gln Leu Phe Arg Ser Leu Ala
                245                 250                 255

Tyr Ile His Ser Gln Gly Val Cys His Arg Asp Ile Asn Leu Leu Val
            260                 265                 270

Asp Pro Asp Thr Ala Ile Leu Lys Leu Cys Asp Phe Gly Ser Ala Lys
        275                 280                 285

Gln Leu Val Leu Gly Thr Thr Val Ala Pro Glu Leu Tyr Thr Ser Ser
    290                 295                 300

Ile Asp Val Xaa Ser Ala Gly Cys Val Leu Ala Glu Leu Leu Leu Ser
305                 310                 315                 320

Gln Pro Ile Phe Pro Gly Asp Asn Gly Val Asp Gln Leu Val Glu Ile
                325                 330                 335

Ile Lys Val Leu Gly Thr Pro Thr Arg Glu Gln Ile Arg Glu Met Asn
            340                 345                 350

Pro Lys Tyr Thr Glu Phe Lys Phe Pro Gln Ile Lys Ala His Pro Trp
        355                 360                 365

Thr Lys Val Phe Lys Ser Arg Thr Ala Pro Arg Pro Leu His Ser Ala
    370                 375                 380

Leu Ala Cys Trp Ser Thr His His Thr Gln Gly Ser Pro His Leu Arg
385                 390                 395                 400

Leu Val Pro Thr Ala Ser Leu Met Asn Cys Gly Val Ser Gly Pro Ala
                405                 410                 415

Pro Gln Arg Pro Pro Thr Ser Pro Cys Ser Thr Ser Val Leu Val Ile
            420                 425                 430

Cys Pro Ser Asn His Leu Ser Met Pro Phe Ser Ser Leu Leu Thr
        435                 440                 445


<210> SEQ ID NO 17
<211> LENGTH: 362
<212> TYPE: PRT
<213> ORGANISM: Caenorhabditis elegans

<400> SEQUENCE: 17

Met Asn Lys Gln Leu Leu Ser Cys Ser Leu Lys Ser Gly Lys Gln Val
1               5                   10                  15

Thr Met Val Val Ala Ser Val Ala Thr Asp Gly Val Asp Gln Gln Val
            20                  25                  30

Glu Ile Ser Tyr Tyr Asp Gln Lys Val Ile Gly Asn Gly Ser Phe Gly
        35                  40                  45

Val Val Phe Leu Ala Lys Leu Ser Thr Thr Asn Glu Met Val Ala Ile
    50                  55                  60

Lys Lys Val Leu Gln Asp Lys Arg Phe Lys Asn Arg Glu Leu Gln Ile
65                  70                  75                  80

Met Arg Lys Leu Asn His Pro Asn Ile Val Lys Leu Lys Tyr Phe Phe
```

85                  90                  95
Tyr Ser Ser Gly Glu Lys Lys Asp Glu Leu Tyr Leu Asn Leu Ile Leu
                100                 105                 110

Glu Tyr Val Pro Glu Thr Val Tyr Arg Val Ala Arg His Tyr Ser Lys
            115                 120                 125

Gln Arg Gln Gln Ile Pro Met Ile Tyr Val Lys Leu Tyr Met Tyr Gln
        130                 135                 140

Leu Leu Arg Ser Leu Ala Tyr Ile His Ser Ile Gly Ile Cys His Arg
145                 150                 155                 160

Asp Ile Lys Pro Gln Asn Leu Leu Ile Asp Pro Glu Ser Gly Val Leu
                165                 170                 175

Lys Leu Cys Asp Phe Gly Ser Ala Lys Tyr Leu Val Arg Asn Glu Pro
            180                 185                 190

Asn Val Ser Tyr Ile Cys Ser Arg Tyr Tyr Arg Ala Pro Glu Leu Ile
        195                 200                 205

Phe Gly Ala Thr Asn Tyr Thr Asn Ser Ile Asp Val Trp Ser Ala Gly
    210                 215                 220

Thr Val Met Ala Glu Leu Leu Leu Gly Gln Pro Ile Phe Pro Gly Asp
225                 230                 235                 240

Ser Gly Val Asp Gln Leu Val Glu Ile Ile Lys Val Leu Gly Thr Pro
                245                 250                 255

Thr Arg Glu Gln Ile Gln Ser Met Asn Pro Asn Tyr Lys Glu Phe Lys
            260                 265                 270

Phe Pro Gln Ile Lys Ala His Pro Trp Asn Lys Val Phe Arg Val His
        275                 280                 285

Thr Pro Ala Glu Ala Ile Asp Leu Ile Ser Lys Ile Ile Glu Tyr Thr
    290                 295                 300

Pro Thr Ser Arg Pro Thr Pro Gln Ala Ala Cys Gln His Ala Phe Phe
305                 310                 315                 320

Asp Glu Leu Arg Asn Pro Asp Ala Arg Leu Pro Ser Gly Arg Pro Leu
                325                 330                 335

Pro Thr Leu Glu Met Asp Gly Pro Met Gly Thr Gly Glu Ile Ser Pro
            340                 345                 350

Thr Ser Gly Asp Val Ala Gly Pro Ser Ala
        355                 360

<210> SEQ ID NO 18
<211> LENGTH: 586
<212> TYPE: DNA
<213> ORGANISM: Caenorhabditis elegans

<400> SEQUENCE: 18
gacaattatc gattaataaa agtttaaaca gacacgagaa attaaatata aaaaattgaa      60
ttgtttattt gttgttttgt gtgtagaaaa ataattttga tagaaacaaa aaattagcgt     120
aaaataaata gctagcgcaa tactcgtgca cgagatgtgc gccagcagct ccttgacgca     180
aaacgtgacg tttagcacca aaatgatttt tgctctttga gttctttgtt ttcgggagca     240
aatttcatgc caatcccttt ctttttttca aattttcctg ttaaattcat gtaataacta     300
ttattcatgt caattacaac aaataagcat ccaagatttt atcataaact cgttcaaacc     360
tccttttacc actcgaaaag caatatctcc gacttccttc aaagagaaat gatgacaaaa     420
catagaaacc tcacgttata cgttttgtca tcacgatttc agtgctcact tttctcattt     480
cattctcgct taatttcatt tttgtcactc tcgcgtcatg ttttgcattt ttcgaaagca     540

-continued tttatttaaa actgaaaaaa taattcgtaa tttttcaaga atggct 586

<210> SEQ ID NO 19
<211> LENGTH: 1584
<212> TYPE: DNA
<213> ORGANISM: Caenorhabditis elegans

<400> SEQUENCE: 19
aaagaatggc tcaaaaagat gaccggattt tgctgttgaa tgctccaagg ctcccgctcg 60
aagatgataa gctcaacgag ctcaccgctg atcttcacga ttgggctcat gctaatgggc 120
ttgtcatgcg tctatcaacc gacaagttga gcagcgaagt ttgtcaaact actccattaa 180
cacttcttcc atctccattc ccgaaaaatg tttttgaaga agcagttcat attcagaacc 240
ttttcgcaag tctttatcac ttcatagctt atgaatttga ttttctaatc gatattcata 300
aaaatgtcgt gaaaactgat gatttcacac ggaatatggt tgagatcttg aagaaagtca 360
aagcccaagg actcaagcaa ccagtcactc tcgcgattca acgatctgat tatatgtgtc 420
ataaggatca atattcagcg gaatatggac tgaaacaaat tgaaataaac aatatcgcct 480
cgtcaatggg agcacatgct ctacggctca ccgaatggca tatcagagtt cttaaagcgt 540
tgaacatttc cgatgacgtc attcaaagag caattccaga aaacaagcca attccaatga 600
tcgctgaagc tttattcaag gcctggtccc acttttcgaa cccagcagct gtggttcttg 660
tcgttgtaga aaacgtcaat caaaatcaga ttgatcaacg ccacgtggaa tatgaacttg 720
aaaagttagg agtaccgatg acatgtatta ttagaagaaa tttaacacaa tgctatgaac 780
aattatcatt gaatgataga agcgatttga tgattgatgg gcgtcaagta gcaattgttt 840
acttcagagc aggatactca cctgatcatt atccatctac aaaagaatgg gaagcacgtg 900
agcgtatgga actttccacc gctatcaaaa ctccatggat cggctacag gtggcaaata 960 ctaagaagac ccagcaggtt ctttctgaag atggagtact cgaaagattc atcggaaaac 1020
cacgagaagc tcgcgatatt cgagcttcat tcgcaggaat gtgggctttg gagaacactg 1080
atgaagtgac tatgaaagtc gtggctggag ctcaaaaaca tccagaagcg tttgttctga 1140
agccacaaac tgaaggtgga gccgcattgc acaccggtga tgagatggtt caaatgctcc 1200
gagaacttcc ggaagaagag cgtggagctt tcattttgat ggagaaactg aaaccgatga 1260
ttattgaaaa ctacctggtt cttgcaaaga agccgatcac atttgctaag gctgttagtg 1320
aacttggagt gtatggttat gcatttggaa ggaaggatgc acctgagctt aagactgctg 1380
ggcatttgct ccgaacgaaa ccggaatcca cagctatggg tggagtagcc gccggacatg 1440
ctgttgtcga caccccattc ctctacgaat ttatttgatt tcgaacataa tcagaaaact 1500
caacaaaaat gctgtgatat gaaaccattt gctatttaga tctttttgtg tttgtaaatt 1560
taatcattgt aatttattga atgt 1584

<210> SEQ ID NO 20
<211> LENGTH: 490
<212> TYPE: PRT
<213> ORGANISM: Caenorhabditis elegans

<400> SEQUENCE: 20

Met Ala Gln Lys Asp Asp Arg Ile Leu Leu Leu Asn Ala Pro Arg Leu
1 5 10 15

Pro Leu Glu Asp Asp Lys Leu Asn Glu Leu Thr Ala Asp Leu His Asp
20 25 30

Trp Ala His Ala Asn Gly Leu Val Met Arg Leu Ser Thr Asp Lys Leu

-continued

```
        35                  40                  45

Ser Ser Glu Val Cys Gln Thr Thr Pro Leu Thr Leu Leu Pro Ser Pro
    50                  55                  60

Phe Pro Lys Asn Val Phe Glu Glu Ala Val His Ile Gln Asn Leu Phe
65                  70                  75                  80

Ala Ser Leu Tyr His Phe Ile Ala Tyr Glu Phe Asp Phe Leu Ile Asp
                85                  90                  95

Ile His Lys Asn Val Val Lys Thr Asp Asp Phe Thr Arg Asn Met Val
            100                 105                 110

Glu Ile Leu Lys Lys Val Lys Ala Gln Gly Leu Lys Gln Pro Val Thr
        115                 120                 125

Leu Ala Ile Gln Arg Ser Asp Tyr Met Cys His Lys Asp Gln Tyr Ser
    130                 135                 140

Ala Glu Tyr Gly Leu Lys Gln Ile Glu Ile Asn Asn Ile Ala Ser Ser
145                 150                 155                 160

Met Gly Ala His Ala Leu Arg Leu Thr Glu Trp His Ile Arg Val Leu
                165                 170                 175

Lys Ala Leu Asn Ile Ser Asp Asp Val Ile Gln Arg Ala Ile Pro Glu
            180                 185                 190

Asn Lys Pro Ile Pro Met Ile Ala Glu Ala Leu Phe Lys Ala Trp Ser
        195                 200                 205

His Phe Ser Asn Pro Ala Ala Val Val Leu Val Val Val Glu Asn Val
    210                 215                 220

Asn Gln Asn Gln Ile Asp Gln Arg His Val Glu Tyr Glu Leu Glu Lys
225                 230                 235                 240

Leu Gly Val Pro Met Thr Cys Ile Ile Arg Arg Asn Leu Thr Gln Cys
                245                 250                 255

Tyr Glu Gln Leu Ser Leu Asn Asp Arg Ser Asp Leu Met Ile Asp Gly
            260                 265                 270

Arg Gln Val Ala Ile Val Tyr Phe Arg Ala Gly Tyr Ser Pro Asp His
        275                 280                 285

Tyr Pro Ser Thr Lys Glu Trp Glu Ala Arg Glu Arg Met Glu Leu Ser
    290                 295                 300

Thr Ala Ile Lys Thr Pro Trp Ile Gly Leu Gln Val Ala Asn Thr Lys
305                 310                 315                 320

Lys Thr Gln Gln Val Leu Ser Glu Asp Gly Val Leu Glu Arg Phe Ile
                325                 330                 335

Gly Lys Pro Arg Glu Ala Arg Asp Ile Arg Ala Ser Phe Ala Gly Met
            340                 345                 350

Trp Ala Leu Glu Asn Thr Asp Glu Val Thr Met Lys Val Val Ala Gly
        355                 360                 365

Ala Gln Lys His Pro Glu Ala Phe Val Leu Lys Pro Gln Thr Glu Gly
    370                 375                 380

Gly Ala Ala Leu His Thr Gly Asp Glu Met Val Gln Met Leu Arg Glu
385                 390                 395                 400

Leu Pro Glu Glu Glu Arg Gly Ala Phe Ile Leu Met Glu Lys Leu Lys
                405                 410                 415

Pro Met Ile Ile Glu Asn Tyr Leu Val Leu Ala Lys Lys Pro Ile Thr
            420                 425                 430

Phe Ala Lys Ala Val Ser Glu Leu Gly Val Tyr Gly Tyr Ala Phe Gly
        435                 440                 445

Arg Lys Asp Ala Pro Glu Leu Lys Thr Ala Gly His Leu Leu Arg Thr
    450                 455                 460
```

-continued

```
Lys Pro Glu Ser Thr Ala Met Gly Gly Val Ala Ala Gly His Ala Val
465                 470                 475                 480

Val Asp Thr Pro Phe Leu Tyr Glu Phe Ile
                485                 490
```

```
<210> SEQ ID NO 21
<211> LENGTH: 794
<212> TYPE: DNA
<213> ORGANISM: Caenorhabditis elegans

<400> SEQUENCE: 21

cattttgaaa gtgcccaagt tgctggaacg ctgaaaattg aaattattaa caaagaaatt      60

tgctttaaaa tccgaaaaat caagaaaaaa tcgataattt cgtcggacaa tccgcctgct     120

agcacggctt gacgctcgtt tgccgcgcgc tcattcgatt tgtgtgagtg cccagtggag     180

cgcgtttgct aaggctaact gtgtagtcct ctcggacaag atctgtgaac attgaaatga     240

aacacttggg ttcaataaaa tcacaagaaa atgatgacaa ttttgtttgc gaccgaaaaa     300

aaattataaa aattgaatat tggttatcat cgtttcaatc tttgttttgt attaaaggca     360

cagctgctaa aaattgtttt ttttttttca attttgctaa aagaaaatca attttctgat     420

tttttgttga gttcccgtgc aaatcaatgt cctagctttt taaaattgtt ttttgttatg     480

taattctaat caaattttgt cgaattttca gagattttct gctaaaacac taaaaatagt     540

ctaaaagtcg ataatttgat aaacatttac tcaaaccttt tacggaaaaa tgaaacaaaa     600

gttgcaaaaa tatagtaatt tcgcaatttt ctgaacgcgt acttaaaggt acacggtttg     660

attcggattg gtcccgccac aaagtgttac cataacattt ttctcgctgc gagacccatc     720

cgaataaatc cgtgcgccta atcagtgcga gtacgcattt catattactg ataagtgcca     780

tttttagaac aatg                                                       794
```

```
<210> SEQ ID NO 22
<211> LENGTH: 1017
<212> TYPE: DNA
<213> ORGANISM: Caenorhabditis elegans

<400> SEQUENCE: 22

atgagcaaat cgatttgcaa atcaagcatg cgcgcagctg tagtccgacg attcggagca      60

cctgatgtca tagaagccgt cgagagtgat atgcccaggc ttgaaaaaaa ccaggttctc     120

gttcggaatt acgctgccgg tgtcaatcca gttgacacat atattcgtgc tggtcagtat     180

ggaaaactac caaatcttcc atatgtacca ggaaaagatg gagccggatt cgtcgaactt     240

gtgggagaaa gcgttaaaaa tgtgaaagtc ggcgatcgag tctggtatgg atcagaagcg     300

gacagtacag cagagtatgt tgcggtgaat cgaccattcg agttgccgga aggagtttcg     360

tttgaggaag gagcttctct cggagtgcct tatcttaccg cttatcgtgc attgtttcat     420

cttgctggtg caaagactgg cgacgttata cttgtacacg gagcatctgg tggagtggga     480

agtgcactga tgcagctggc tgcctggagg aacattgaag ctgttggcac tgctggatct     540

gctgatggga tccggttcgt gaagagtctt ggtgcacgga atgtctataa tcattcggat     600

aagcaatatg tgtcgaaaat gaaaaatgat tatccaggag gcttcaacca cattttcgaa     660

atggctgctc acacaaatct gaacacggac ctcggattgc tggctccacg tggtagagtt     720

gcagtaattg gaaatcgcgc cgagaccacg atcaacgcaa gacaacttat ggttacagaa     780

ggagctgttt acggtgtagc attgggaatg tcttccgagg ctgagctctt ggactttggc     840
```

-continued

```
atcaacattg tctcattctt gaaggaaacc gagtttcgtc cacttataaa caaattgtat    900

cgtctcgagc aattaggact ggctcatgag gaaattatga acaacaaggg agcgaaagga    960

aatcttgtag tgcaaatcga acattaattc attattttaa cacgccattt aaaggaa      1017


<210> SEQ ID NO 23
<211> LENGTH: 328
<212> TYPE: PRT
<213> ORGANISM: Caenorhabditis elegans

<400> SEQUENCE: 23

Met Ser Lys Ser Ile Cys Lys Ser Ser Met Arg Ala Ala Val Val Arg
1               5                   10                  15

Arg Phe Gly Ala Pro Asp Val Ile Glu Ala Val Glu Ser Asp Met Pro
            20                  25                  30

Arg Leu Glu Lys Asn Gln Val Leu Val Arg Asn Tyr Ala Ala Gly Val
        35                  40                  45

Asn Pro Val Asp Thr Tyr Ile Arg Ala Gly Gln Tyr Gly Lys Leu Pro
    50                  55                  60

Asn Leu Pro Tyr Val Pro Gly Lys Asp Gly Ala Gly Phe Val Glu Leu
65                  70                  75                  80

Val Gly Glu Ser Val Lys Asn Val Lys Val Gly Asp Arg Val Trp Tyr
                85                  90                  95

Gly Ser Glu Ala Asp Ser Thr Ala Glu Tyr Val Ala Val Asn Arg Pro
            100                 105                 110

Phe Glu Leu Pro Glu Gly Val Ser Phe Glu Glu Gly Ala Ser Leu Gly
        115                 120                 125

Val Pro Tyr Leu Thr Ala Tyr Arg Ala Leu Phe His Leu Ala Gly Ala
    130                 135                 140

Lys Thr Gly Asp Val Ile Leu Val His Gly Ala Ser Gly Gly Val Gly
145                 150                 155                 160

Ser Ala Leu Met Gln Leu Ala Ala Trp Arg Asn Ile Glu Ala Val Gly
                165                 170                 175

Thr Ala Gly Ser Ala Asp Gly Ile Arg Phe Val Lys Ser Leu Gly Ala
            180                 185                 190

Arg Asn Val Tyr Asn His Ser Asp Lys Gln Tyr Val Ser Lys Met Lys
        195                 200                 205

Asn Asp Tyr Pro Gly Gly Phe Asn His Ile Phe Glu Met Ala Ala His
    210                 215                 220

Thr Asn Leu Asn Thr Asp Leu Gly Leu Leu Ala Pro Arg Gly Arg Val
225                 230                 235                 240

Ala Val Ile Gly Asn Arg Ala Glu Thr Thr Ile Asn Ala Arg Gln Leu
                245                 250                 255

Met Val Thr Glu Gly Ala Val Tyr Gly Val Ala Leu Gly Met Ser Ser
            260                 265                 270

Glu Ala Glu Leu Leu Asp Phe Gly Ile Asn Ile Val Ser Phe Leu Lys
        275                 280                 285

Glu Thr Glu Phe Arg Pro Leu Ile Asn Lys Leu Tyr Arg Leu Glu Gln
    290                 295                 300

Leu Gly Leu Ala His Glu Glu Ile Met Asn Asn Lys Gly Ala Lys Gly
305                 310                 315                 320

Asn Leu Val Val Gln Ile Glu His
                325


<210> SEQ ID NO 24
```

-continued

<211> LENGTH: 1234
<212> TYPE: DNA
<213> ORGANISM: Caenorhabditis elegans

<400> SEQUENCE: 24
agaacttttc gagaagtcta ccgttgtagt tttcgaaata gtaatttatt tagtgacgtt 60
tataaaggtt tacatgattt ggtttggaaa ttttttagga gtttattcat aaaaacaaag 120
taaccatgga cattccagaa gtctatagta cacgcgatcc taccgtaccc ttcagtattt 180
ctatcagatt gatagctttc ggtagtcagg tacagcctaa aaaattcctg cttgcctttt 240
tgcctacatg tctgcctacc ttcagtcata atgcctacat aatgattttt tccaattgaa 300
acttgcagac agaaattcaa atggcaaaaa gaaacaaaca ccgaaacatt aatcacattt 360
cttttcatat cagttttcct gtcaaagcac atttctggag tctgtgtgta tttttttgtg 420
tctttatgtg atcggtgttg tgaaatttgt agttgatgtt gataacatac ttttttttga 480
aacaaaaagt gattgattag gcttgaattc agagatatgt tcgtgatact ttgcgattct 540
cgagccaaaa acacggtatc cggtctcgac acgacaactt tttcgcaaaa tacaagctga 600
tgtgcgcctt gaaagagtac tgtaatttca acctttcgtt gttgcggaat tttcatagtt 660
tctcgttcaa aatatatgta tttattaaac aaaaaactaa aacaaaacaa ttgagaacac 720
ataaattgtg aaaaatcaat gagaccacag caaaaaattt tgtatctaca gtactcttta 780
aaggcgcaca tccgttctta ttttcagcaa aaatgtcgct tcgagaccgg gtaccgtatt 840
tttttttgtg caaaacttta ggtctaggta atattaaaaa aaaattccac aaaactagaa 900
tctagagctt tccattaaat tttttgatga catttgaaaa ttcatgatga ttttttttcca 960 acaatttcga aatatccctc ttttcacctg gtccactgaa ttctctttcc gaaagaccac 1020
cacaatttca gggctccgcc catttcgtgg tttgtagcct tcccgaccct acgtttttga 1080
tgacaattgt gagagaagtg agaggttcag acacaaaaag cgacgtggtc gaatgagtat 1140
aaatagagag tgaagtttcc aatttccctc acaattgttt gtttgcaatc cactttccaa 1200
aaaaacacaa cttcaatcaa aaatcattat ggtt 1234

<210> SEQ ID NO 25
<211> LENGTH: 664
<212> TYPE: DNA
<213> ORGANISM: Caenorhabditis elegans

<400> SEQUENCE: 25
atggtttcct acaagttgac ctacttcaat ggacgtggcg ctggagaagt gtctcgtcag 60
attttcgcct atgccggaca acaatacgag gataatagag tcactcagga acaatggcca 120
gcattgaaag aaacctgcgc tgctccattc ggacaacttc cattcctcga agtcgacggt 180
aagaagcttg ctcaatccca cgcgattgct cgtttcttgg ctcgtgagtt caagctcaac 240
ggaaaaaccg cctgggaaga ggctcaagtg aactctcttg ccgatcaata caaggattat 300
tcaagtgagg ctcgtccata tttctacgct gtcatgggat tcggtccagg agacgttgaa 360
actttgaaga aagacatctt ccttccagca tttgaaaagt tctacggatt cttggtcaac 420
ttcttgaagg cttcgggatc cggattcctt gtcggagact ctttgacctg gattgacttg 480
gctattgccc aacattcagc tgatttgatt gccaagggag gtgatttcag caagttccca 540
gagctcaagg ctcatgccga gaagatccag gcgattccac aaatcaagaa atggatcgag 600
acccgtccag tcacaccatt ctaaatagct gtataaaatc tgcaaataaa tatttttttt 660
tttt 664

-continued

<210> SEQ ID NO 26
<211> LENGTH: 207
<212> TYPE: PRT
<213> ORGANISM: Caenorhabditis elegans

<400> SEQUENCE: 26

```
Met Val Ser Tyr Lys Leu Thr Tyr Phe Asn Gly Arg Gly Ala Gly Glu
1               5                   10                  15

Val Ser Arg Gln Ile Phe Ala Tyr Ala Gly Gln Gln Tyr Glu Asp Asn
            20                  25                  30

Arg Val Thr Gln Glu Gln Trp Pro Ala Leu Lys Glu Thr Cys Ala Ala
        35                  40                  45

Pro Phe Gly Gln Leu Pro Phe Leu Glu Val Asp Gly Lys Lys Leu Ala
    50                  55                  60

Gln Ser His Ala Ile Ala Arg Phe Leu Ala Arg Glu Phe Lys Leu Asn
65                  70                  75                  80

Gly Lys Thr Ala Trp Glu Glu Ala Gln Val Asn Ser Leu Ala Asp Gln
                85                  90                  95

Tyr Lys Asp Tyr Ser Ser Glu Ala Arg Pro Tyr Phe Tyr Ala Val Met
            100                 105                 110

Gly Phe Gly Pro Gly Asp Val Glu Thr Leu Lys Lys Asp Ile Phe Leu
        115                 120                 125

Pro Ala Phe Glu Lys Phe Tyr Gly Phe Leu Val Asn Phe Leu Lys Ala
    130                 135                 140

Ser Gly Ser Gly Phe Leu Val Gly Asp Ser Leu Thr Trp Ile Asp Leu
145                 150                 155                 160

Ala Ile Ala Gln His Ser Ala Asp Leu Ile Ala Lys Gly Gly Asp Phe
                165                 170                 175

Ser Lys Phe Pro Glu Leu Lys Ala His Ala Glu Lys Ile Gln Ala Ile
            180                 185                 190

Pro Gln Ile Lys Lys Trp Ile Glu Thr Arg Pro Val Thr Pro Phe
        195                 200                 205
```

<210> SEQ ID NO 27
<211> LENGTH: 404
<212> TYPE: DNA
<213> ORGANISM: Caenorhabditis elegans

<400> SEQUENCE: 27

```
tctcattctc ttcaagacat aacacaacgg gctgacgacc atatcatcaa cgacgatttt      60

ttaggaactg tactttatct gtgtctgacc aacacgtgtg aatgaagttt caactggaaa     120

atttgtttga aacactgcaa agaatttcga attttgatga taattttaaa tgccattatc     180

agttttaata cgccactcta gtctttgatt ctttgcacac acacacacac acacacacac     240

acacacacac tcacaaacac gcctgaaatt tcgcaatatg ctgatttaac gagaaaacat     300

ttgatgacaa taaacttggc gtattaatat aaaagggaaa attcaattca gattctcaac     360

ggtttatttt ctgtcacaac tcttcctaat attcaccatg gttt                      404
```

<210> SEQ ID NO 28
<211> LENGTH: 630
<212> TYPE: DNA
<213> ORGANISM: Caenorhabditis elegans

<400> SEQUENCE: 28

```
atggtttcct acaagcttac ctacttcgat ggacgcggag ccggagagct ctgccgtcaa      60
```

-continued

```
atctttgctg ccgccgagca gaaatatgaa gataacagac ttaccgatga ggagtgggag    120

aagttcaaag cggccggaaa aaccccatac aaccagcttc caatgctcga ggtagatggc    180

aaaccactcg ctcagtccca cgcgatggct cgttatcttg ctcgggaatt cgggttcaac    240

ggaaagagca gatgggaaga agctcaagtc aactccttgg ccgaccagta caaagactat    300

tacgcggagg ctcgtccata cctcgctgtg aagcttggtt acacagaagg agacgcggag    360

gctctttaca caagcgtcta tcttccagtt ttcaagaaac actatggatt ctttgtcaat    420

gctttgaagg ccagcgggtc aggattcttg gttggaaatt ccttgacttt tattgatttg    480

cttgttgctc agcattcagc tgatttgctg ggacgtgaaa agtcggatct tttcaatgat    540

gtcccagaga tgaaggcaca ttccgaaaaa gttcagtcaa ttcctcagat caagaaatgg    600

attgagactc gtccagcgag tgactggtaa                                      630
```

```
<210> SEQ ID NO 29
<211> LENGTH: 209
<212> TYPE: PRT
<213> ORGANISM: Caenorhabditis elegans

<400> SEQUENCE: 29

Met Val Ser Tyr Lys Leu Thr Tyr Phe Asp Gly Arg Gly Ala Gly Glu
1               5                   10                  15

Leu Cys Arg Gln Ile Phe Ala Ala Ala Glu Gln Lys Tyr Glu Asp Asn
            20                  25                  30

Arg Leu Thr Asp Glu Glu Trp Glu Lys Phe Lys Ala Ala Gly Lys Thr
        35                  40                  45

Pro Tyr Asn Gln Leu Pro Met Leu Glu Val Asp Gly Lys Pro Leu Ala
    50                  55                  60

Gln Ser His Ala Met Ala Arg Tyr Leu Ala Arg Glu Phe Gly Phe Asn
65                  70                  75                  80

Gly Lys Ser Arg Trp Glu Glu Ala Gln Val Asn Ser Leu Ala Asp Gln
                85                  90                  95

Tyr Lys Asp Tyr Tyr Ala Glu Ala Arg Pro Tyr Leu Ala Val Lys Leu
            100                 105                 110

Gly Tyr Thr Glu Gly Asp Ala Glu Ala Leu Tyr Thr Ser Val Tyr Leu
        115                 120                 125

Pro Val Phe Lys Lys His Tyr Gly Phe Phe Val Asn Ala Leu Lys Ala
    130                 135                 140

Ser Gly Ser Gly Phe Leu Val Gly Asn Ser Leu Thr Phe Ile Asp Leu
145                 150                 155                 160

Leu Val Ala Gln His Ser Ala Asp Leu Leu Gly Arg Glu Lys Ser Asp
                165                 170                 175

Leu Phe Asn Asp Val Pro Glu Met Lys Ala His Ser Glu Lys Val Gln
            180                 185                 190

Ser Ile Pro Gln Ile Lys Lys Trp Ile Glu Thr Arg Pro Ala Ser Asp
        195                 200                 205

Trp
```

```
<210> SEQ ID NO 30
<211> LENGTH: 1137
<212> TYPE: DNA
<213> ORGANISM: Caenorhabditis elegans

<400> SEQUENCE: 30

aattgaaatg agtttgcaat tttgtattat tttttaattc atatttcaag aagcaatttt      60
```

-continued

```
ttgctaattt gttttaatgg aaatcgatgt ttctaaaata tcttgaatga attgttcttt    120

taaaaatttt atggtaaagt tttcagcagg atgtttctat agaagctttt tgcattgcaa    180

gagtgttgaa atatacagga tatttacaaa agcctgggaa gtaggcatgc ttttaggtac    240

aaatcagacc tacaccgcct tcctttgtgg tttaccatca tagctaaaac tttccgaaca    300

ttccctggtg agacacaatg ttcaaagcac aaaaccaatc acgtcataat gttaatttga    360

cttttattgt caaaaattac aaaagcgtcg ttttctggaa catgaacata ataagaattt    420

tcaaatttcg gtgggcacaa taaatatgta atcttttatt tatttttgga ggatagtctt    480

ttcaaaggca ggtgtataac cctcaaaaga aagcacgttt gtgtttcaaa gtgagactta    540

aattatttca aagacaaatt ccataggaaa tcattgttca tcaggcacct tcccagaaat    600

taggctgtag gcaggcacgt aggctgcggt aaatgcctac gcctcttttg cgcgagatta    660

tgaaattgtg ttgtactgtc ggaaaaattt cagaaacaaa aaaaaatatt ttttgtgact    720

ttttgtgtca gttatagtag tttcttatca tggtatcttc aataataatg gcaagcgtaa    780

caagatgatt gatgccatgg gtttatattt gtgagtagtc acaaattgtg acacaacatt    840

cccttcgaaa gatctggaaa agtcacaaaa ccttgcatat atttttttca accaatatta    900

ttttgaccta ctctgttcat cgtaacattg caacaacaaa aaacgatgac tacactttat    960

gatttctagt caacaacgtg cgcgcaatgt gtagagcaaa tgatgacaaa ctacagaata   1020

tggtgagtgg agagacgaca gacatttgag aaatgggtat aaatagagac ggccggcatt   1080

cagtgttcaa cccttctcat cgaccactcg atttcttgct tggttatttc aacaatg      1137
```

<210> SEQ ID NO 31
<211> LENGTH: 665
<212> TYPE: DNA
<213> ORGANISM: Caenorhabditis elegans

<400> SEQUENCE: 31

```
cgaccactcg atttcttgct tggttatttc aacaatggtc cactacaagg tatcgtactt     60

cccaattcgt ggagctggag agattgctcg tcagatcttg gcctacgctg gacaagactt    120

cgaggacaac agaatcccaa aggaggaatg gccagctgtc aagccaagca ctccattcgg    180

acagcttcca ctccttgaag ttgacggaaa ggttcttgcc caatctcatg ctatcgcccg    240

ttacttggct cgtcagttcg gaatcaatgg aaagtgtgca tgggaggagg ctcaagtcaa    300

ctcggttgct gatcaattca aggattacct caacgaagtt cgtccatact tcatggtgaa    360

gatgggattt gctgaaggag atctcgatgc tcttgccaag gacgtcttcc ttccaggatt    420

caagaagcac tatggattct ttgctaactt cctcaagtcg gctggatccg gatacttggt    480

tggagactct ttgacctttg tcgacttgct cgtcgctcag cacactgctg atcttctggc    540

tgccaacgca gctcttctcg atgaattccc acaattcaag gctcatcagg aaaaggttca    600

ctcgaatgcc aacatcaaga agtggttgga gactcgtcca gttactccat tctaaatgat    660

ttcca                                                                665
```

<210> SEQ ID NO 32
<211> LENGTH: 206
<212> TYPE: PRT
<213> ORGANISM: Caenorhabditis elegans

<400> SEQUENCE: 32

```
Met Val His Tyr Lys Val Ser Tyr Phe Pro Ile Arg Gly Ala Gly Glu
1               5                   10                  15
```

-continued

```
Ile Ala Arg Gln Ile Leu Ala Tyr Ala Gly Gln Asp Phe Glu Asp Asn
            20                  25                  30

Arg Ile Pro Lys Glu Glu Trp Pro Ala Val Lys Pro Ser Thr Pro Phe
        35                  40                  45

Gly Gln Leu Pro Leu Leu Glu Val Asp Gly Lys Val Leu Ala Gln Ser
    50                  55                  60

His Ala Ile Ala Arg Tyr Leu Ala Arg Gln Phe Gly Ile Asn Gly Lys
65                  70                  75                  80

Cys Ala Trp Glu Glu Ala Gln Val Asn Ser Val Ala Asp Gln Phe Lys
                85                  90                  95

Asp Tyr Leu Asn Glu Val Arg Pro Tyr Phe Met Val Lys Met Gly Phe
            100                 105                 110

Ala Glu Gly Asp Leu Asp Ala Leu Ala Lys Asp Val Phe Leu Pro Gly
        115                 120                 125

Phe Lys Lys His Tyr Gly Phe Phe Ala Asn Phe Leu Lys Ser Ala Gly
    130                 135                 140

Ser Gly Tyr Leu Val Gly Asp Ser Leu Thr Phe Val Asp Leu Leu Val
145                 150                 155                 160

Ala Gln His Thr Ala Asp Leu Leu Ala Ala Asn Ala Ala Leu Leu Asp
                165                 170                 175

Glu Phe Pro Gln Phe Lys Ala His Gln Glu Lys Val His Ser Asn Ala
            180                 185                 190

Asn Ile Lys Lys Trp Leu Glu Thr Arg Pro Val Thr Pro Phe
        195                 200                 205
```

<210> SEQ ID NO 33
<211> LENGTH: 420
<212> TYPE: DNA
<213> ORGANISM: Caenorhabditis elegans

<400> SEQUENCE: 33

```
attatccaaa aagattagaa gttggcaaac cttgggcaag aatttccaga gattgcacta     60

aagttgtagc caagtttgat ccaactttat ccaatctttt actaaaatta tccttaagac    120

tatttaaatt ttagatagag aattggcgag agttagatcc cacttggata tgacttatag    180

ttagcctaac ctgaagctat tgcttgcttg atcatttggt ttatcgcttt gctacttgga    240

taaccagctc caatagttgt tatttttgct tttgtcatca tttttccacg atttacactc    300

tcaagtgaaa ccaactgttc tttgatgcca gacgatgaca ttacacttga taagaaaata    360

tatataaact ggaattaaaa acaattgata catcgattca attactgaat tctaattatg    420
```

<210> SEQ ID NO 34
<211> LENGTH: 716
<212> TYPE: DNA
<213> ORGANISM: Caenorhabditis elegans

<400> SEQUENCE: 34

```
atgccaaact ataagctatt gtattttgat gctcgtgctc ttgctgagcc aatccgtatc     60

atgtttgcaa tgctcaatgt gccttacgag gattatagag tttcagtgga agaatggtca    120

aagctgaagc caacgactcc atttggccag cttcccattt tacaagtcga tggagaacaa    180

ttcggtcagt caatgtctat cacaagatac ttggcaagaa aatttggact cgctggaaaa    240

actgcagagg aagaagctta cgctgattca attgtagatc aatacagaga tttcatattc    300

tttttccgtc aattcacttc ttccgttttc tatggaagtg acgctgatca tattaacaaa    360
```

-continued

```
gtacgttttg aagttgttga accagcccgt gatgatttct tggcaataat caataagttc    420

ctggccaaga gtaaatcagg attcctcgtt ggagactcat tgacttgggc tgatattgtg    480

attgctgaca atttgacaag tctcctgaag aatggattct tagatttcaa caaagaaaag    540

aagttggaag agttctataa caagattcat tcaattccag aaattaagaa ttacgtggca    600

acaagaaagg atagtattgt ttaaaatcga attatttaag tctgaattat gtatgtagta    660

aaataatatc gttcctatca cgtctcccag agagcgtaat aaattattat tatgtg        716


<210> SEQ ID NO 35
<211> LENGTH: 207
<212> TYPE: PRT
<213> ORGANISM: Caenorhabditis elegans

<400> SEQUENCE: 35

Met Pro Asn Tyr Lys Leu Leu Tyr Phe Asp Ala Arg Ala Leu Ala Glu
1               5                   10                  15

Pro Ile Arg Ile Met Phe Ala Met Leu Asn Val Pro Tyr Glu Asp Tyr
            20                  25                  30

Arg Val Ser Val Glu Glu Trp Ser Lys Leu Lys Pro Thr Thr Pro Phe
        35                  40                  45

Gly Gln Leu Pro Ile Leu Gln Val Asp Gly Glu Gln Phe Gly Gln Ser
    50                  55                  60

Met Ser Ile Thr Arg Tyr Leu Ala Arg Lys Phe Gly Leu Ala Gly Lys
65                  70                  75                  80

Thr Ala Glu Glu Glu Ala Tyr Ala Asp Ser Ile Val Asp Gln Tyr Arg
                85                  90                  95

Asp Phe Ile Phe Phe Phe Arg Gln Phe Thr Ser Ser Val Phe Tyr Gly
            100                 105                 110

Ser Asp Ala Asp His Ile Asn Lys Val Arg Phe Glu Val Val Glu Pro
        115                 120                 125

Ala Arg Asp Asp Phe Leu Ala Ile Ile Asn Lys Phe Leu Ala Lys Ser
    130                 135                 140

Lys Ser Gly Phe Leu Val Gly Asp Ser Leu Thr Trp Ala Asp Ile Val
145                 150                 155                 160

Ile Ala Asp Asn Leu Thr Ser Leu Leu Lys Asn Gly Phe Leu Asp Phe
                165                 170                 175

Asn Lys Glu Lys Lys Leu Glu Glu Phe Tyr Asn Lys Ile His Ser Ile
            180                 185                 190

Pro Glu Ile Lys Asn Tyr Val Ala Thr Arg Lys Asp Ser Ile Val
        195                 200                 205


<210> SEQ ID NO 36
<211> LENGTH: 603
<212> TYPE: DNA
<213> ORGANISM: Caenorhabditis elegans

<400> SEQUENCE: 36

attccgcaac cccgtcaaat ttaagaagag aaagaaaaaa aacacaacgt gtttgcacct     60

gtaaggtagt tttttttgt tgccttcggc gttttgattc acatgaaagt ttctacggaa    120

aaactttcat tgcataacga tcttcatatc ttgtttctgg aaacgaaaat ttccaacatg    180

aaagaaaccc gacgctattt attctcgcaa cacaaaaatt tcacatttaa ataaccgcgg    240

tttttctcga acagcatatt tgacgcgcat tgctcgtcaa gtttgatgcg tgcacactat    300

tttgctgttg tttttttctt ttttctctaa attttcttta cgctttcgta gtttctatag    360
```

-continued

```
aaacgattct ccactcccgg ttttcttccg attctcaaaa ttaattaaaa tttagttatt    420

aaaaatcctt tttcttgaaa taatcgttca atttcgagtt ttcaagagtg gagacgttga    480

atttgtgagc cgcttatttt ttctgtgttt ttgttttgtg gtttttaatc agtgtcataa    540

tcatactttc cattgtttct ttattattca aagttgtaga ttcagtattt tagatcggtg    600

atg                                                                  603
```

<210> SEQ ID NO 37
<211> LENGTH: 718
<212> TYPE: DNA
<213> ORGANISM: Caenorhabditis elegans

<400> SEQUENCE: 37

```
tttagatcgg tgatgtttat gaatcttctc actcaggtct ccaacgcgat tttccgcag      60

gtcgaagccg ctcaaaaaat gtcgaaccgt gctgtcgctg ttcttcgtgg agaaactgtt    120

accggtacta tctggatcac acagaagtcc gaaaatgacc aggcagttat tgaaggagaa    180

atcaagggac ttactcccgg tcttcatgga ttccacgttc accaatatgg tgattccacc    240

aacggatgca tttctgccgg tccacacttc aatccatttg gaaagactca tggtggacca    300

aaatccgaga tccgtcacgt aggcgatcta ggaaatgtgg aagctggagc cgatggagtg    360

gcaaaaatca agctcaccga cacgctcgtc acgctttacg gtccaaacac tgtcgttggc    420

cgatctatgg ttgttcatgc cggacaagac gacctcggcg agggagtcgg agacaaggca    480

gaagagtcca agaagactgg aaacgccgga gctcgtgctg cctgcggtgt cattgctctc    540

gctgctcccc agtgactacc tgaatcgcgt ctctgaatct ccacacaatt cctactaaag    600

acaatttttc atttcttgct ttgtcgttat attcttaaga atcccgttgt tcctactcct    660

actactgtat attttcacat aaaatttctt caaaatttca aataaaggtt gtagtttc      718
```

<210> SEQ ID NO 38
<211> LENGTH: 180
<212> TYPE: PRT
<213> ORGANISM: Caenorhabditis elegans

<400> SEQUENCE: 38

```
Met Phe Met Asn Leu Leu Thr Gln Val Ser Asn Ala Ile Phe Pro Gln
1               5                   10                  15

Val Glu Ala Ala Gln Lys Met Ser Asn Arg Ala Val Ala Val Leu Arg
            20                  25                  30

Gly Glu Thr Val Thr Gly Thr Ile Trp Ile Thr Gln Lys Ser Glu Asn
        35                  40                  45

Asp Gln Ala Val Ile Glu Gly Glu Ile Lys Gly Leu Thr Pro Gly Leu
    50                  55                  60

His Gly Phe His Val His Gln Tyr Gly Asp Ser Thr Asn Gly Cys Ile
65                  70                  75                  80

Ser Ala Gly Pro His Phe Asn Pro Phe Gly Lys Thr His Gly Gly Pro
                85                  90                  95

Lys Ser Glu Ile Arg His Val Gly Asp Leu Gly Asn Val Glu Ala Gly
            100                 105                 110

Ala Asp Gly Val Ala Lys Ile Lys Leu Thr Asp Thr Leu Val Thr Leu
        115                 120                 125

Tyr Gly Pro Asn Thr Val Val Gly Arg Ser Met Val Val His Ala Gly
130                 135                 140

Gln Asp Asp Leu Gly Glu Gly Val Gly Asp Lys Ala Glu Glu Ser Lys
145                 150                 155                 160
```

-continued

Lys Thr Gly Asn Ala Gly Ala Arg Ala Ala Cys Gly Val Ile Ala Leu
165 170 175

Ala Ala Pro Gln
180

<210> SEQ ID NO 39
<211> LENGTH: 1577
<212> TYPE: DNA
<213> ORGANISM: Caenorhabditis elegans

<400> SEQUENCE: 39
tgaataaaaa cgttgaaccc aacggacatc aaagtatcaa agtaagtaag taagtaagta 60
acctgaataa aaacgttgca tataaaaaat ctactcgaaa attaagtgag aattgaagga 120
ttgctttccg aagagaaaat gacaattata gggtatacta aaacatcaaa aatgtatatt 180
agactaccat aaatataaaa catcagtgct gctctccaag ctattctgac ggattgcgac 240
aacgagctcg ctggagttgg catcagtgtg gaaggcagac acataagaag actcgaattt 300
gcggatgacg tagtcctgac atgttccaca ccgggagaag ttcaagaacg actggaaatt 360
ttggaccgaa taagttctaa ttacggactc aagatcaatc agtcaaagac tgttcttctg 420
aagaacaagt tttgccggag ccaagacgtc cttttcaacg gatcccccat cattcccgtg 480
cctggttgcc gctatctggg tcgctggatc gacatttctg gctcaattga cgaagagatc 540
tcgaggagaa taagagcagg ttggggtgct ctggttggaa tcaaagaagt cttgagaatc 600
atgccaaaca aggaaagaat catcctcttc aagcaaaatg tgctaccagc tctcctgtat 660
gctagtgaaa cttggacttg taatgctgga tccacgttga gactcaaaag aactgtcacc 720
ggtctcatcg acgctgcaga aattcgaggc tggaacttca acttggaacg ttacctcctt 780
gcaaaacaat caagatttgc aggacacatt ctacggagag atccaaaccg atggacaaaa 840
atctgcacgg aatgggaccc gagccacaac aaaaaattgga aacgtgccgt tggaggacag 900
aagaagagat gggctaagga catcgacgaa gaatacgcaa aattccacca caattccgcc 960
atgtcgggac aagtcgttgt tgggagaaga agactaggaa tgctcactcc gaaggctcca 1020
tggctgtcca tcgcacgaac cgaccgtgaa aaatggaaag agtttgtccg cagttgcctc 1080
gcaacttgaa cccaacggac atcaaagtat caaagtaagt aagtaagtaa gtaacctgaa 1140
taaaaacgtt gcaattaaaa aatctactcg aaaattaagt gagaattgaa ggattgcttt 1200
ccgaagagaa aatgacaatt atagggtata ctaaaacatc aaaaatgtat attagactac 1260
cataaatatt acgataattt aaaaattact agaaacacgc aattcggctc aaaaagcaac 1320
aatttagact gaaaacgagc taaaagaata ttattcaaaa accactttgc tcggtaaatc 1380
tggtgtatca tgttccgcaa acactgtctt ttgttttgcg tactttgttt acgcgcattc 1440
gaatttcagt gttcgcgctt tttgtttact tttttatttt tcatccaaaa atcgtatttt 1500
cagcttgata tgtttctgcg aattgtaaaa atttatattt gactattgaa tattttaatt 1560
atttgcagcc gaaaatg 1577

<210> SEQ ID NO 40
<211> LENGTH: 813
<212> TYPE: DNA
<213> ORGANISM: Caenorhabditis elegans

<400> SEQUENCE: 40
tttgcagccg aaaatgcttc aaaacaccgt tcgctgtgtc tcaaagcttg ttcaaccgat 60

-continued

```
cacaggagtc gctgctgttc gctcgaagca ctcgctgcca gatttaccat acgactatgc    120

tgatttggag cctgtaatca gtcacgagat tatgcaactt catcatcaaa agcatcatgc    180

cacttatgtg aacaatctca accaaattga ggaaaagctt cacgaggcgg tctccaaagg    240

aaacgtcaaa gaagctatcg ctcttcagcc agctctcaag ttcaatggag gaggacatat    300

caaccactcc atcttctgga ctaatttggc aaaggacgga ggagaaccat cggcggagtt    360

gctcaccgca attaagagcg acttcggatc tctggataat cttcaaaaac agctttcggc    420

atcaactgtc gctgttcaag gatcaggatg gggatggttg ggatactgtc caaagggaaa    480

gatcttgaag gttgccacat gtgccaatca ggatccactt gaggcaacaa ctggacttgt    540

tccactgttc ggaattgacg tctgggagca cgcttactac ttgcagtaca agaatgttcg    600

accagattat gtcaatgcta tttggaagat cgccaactgg aagaacgtca gcgagcgttt    660

tgcaaaggca cagcaataaa tgagctgaat cacaagaatt aatcgtcaaa tgtagcagta    720

gaagttgact cccattgttt tgtaactatt tttgtttctt aattatttcg aaatgtaaat    780

tttcaaacct tttcaaatga aaagttttca ccg                                 813
```

<210> SEQ ID NO 41
<211> LENGTH: 221
<212> TYPE: PRT
<213> ORGANISM: Caenorhabditis elegans

<400> SEQUENCE: 41

```
Met Leu Gln Asn Thr Val Arg Cys Val Ser Lys Leu Val Gln Pro Ile
1               5                   10                  15

Thr Gly Val Ala Ala Val Arg Ser Lys His Ser Leu Pro Asp Leu Pro
            20                  25                  30

Tyr Asp Tyr Ala Asp Leu Glu Pro Val Ile Ser His Glu Ile Met Gln
        35                  40                  45

Leu His His Gln Lys His His Ala Thr Tyr Val Asn Asn Leu Asn Gln
    50                  55                  60

Ile Glu Glu Lys Leu His Glu Ala Val Ser Lys Gly Asn Val Lys Glu
65                  70                  75                  80

Ala Ile Ala Leu Gln Pro Ala Leu Lys Phe Asn Gly Gly Gly His Ile
                85                  90                  95

Asn His Ser Ile Phe Trp Thr Asn Leu Ala Lys Asp Gly Gly Glu Pro
            100                 105                 110

Ser Ala Glu Leu Leu Thr Ala Ile Lys Ser Asp Phe Gly Ser Leu Asp
        115                 120                 125

Asn Leu Gln Lys Gln Leu Ser Ala Ser Thr Val Ala Val Gln Gly Ser
    130                 135                 140

Gly Trp Gly Trp Leu Gly Tyr Cys Pro Lys Gly Lys Ile Leu Lys Val
145                 150                 155                 160

Ala Thr Cys Ala Asn Gln Asp Pro Leu Glu Ala Thr Thr Gly Leu Val
                165                 170                 175

Pro Leu Phe Gly Ile Asp Val Trp Glu His Ala Tyr Tyr Leu Gln Tyr
            180                 185                 190

Lys Asn Val Arg Pro Asp Tyr Val Asn Ala Ile Trp Lys Ile Ala Asn
        195                 200                 205

Trp Lys Asn Val Ser Glu Arg Phe Ala Lys Ala Gln Gln
    210                 215                 220
```

<210> SEQ ID NO 42
<211> LENGTH: 1162

-continued

<212> TYPE: DNA
<213> ORGANISM: Caenorhabditis elegans

<400> SEQUENCE: 42
aaaaaaaaat cgataaaaaa tccgcgtcaa cgaaagttta aagttacagt atttgtcgtt 60
tcgagaccgg gtaccgtagt ttttggtgaa aacattgcaa aatttggtca acaatttcat 120
cgctgcgaga ccgacacaac actttatttt atttttgggt ttcccttatc gcttatcata 180
aacatgtgac gtcatcatct cttgtacaga gcaccgcgac tgggagtata agaatcgccg 240
gaaaacatca ataatcagtt cggtagaagt gaaaattgag cgtaaaatat gatcattttt 300
cgatgcacca tatttgacgc gcaatacttc tacaagccgc tgtgtactgc tcgtggacaa 360
ctttggatta ttttttgttt ttaaaattca aaatagtcaa tatattgctt atttatagcg 420 cgccttttttg acagtaagtt tgtcaaattt gcgcgtaagt tatggtgttt gcacatatgc 480
accatacagc aacaccccgc ggcccggcta gtggtacatc catgcaaatg cgctctactg 540
ataatttgag tttaaccagg tttaggcgca agataagaaa aaagctttgg accaaaaaat 600
ttagagttta ttttttttcgg acatttttta tatacatcac aaaaatattg ggccactcgt 660
ttttgataaa aacgacaagc ccaaaagttc aggtatacgg tagacaaatt gcgtacaggt 720
accacttttc cacgtagtgc caggttgtcc cattacgctt tgatctatga aaaatgcggg 780
aatttttcgt ccagaaaaat gtgacgtcag cacgttctca accatgcgaa atcagttgaa 840
aactctgcgt ctattctccc gcattttttg tagatctgta gatttgtaga tcaatccatt 900
ccccgtatac cctgacccat aatcaatacc tacctaattt ttgtctttcc ccctactttt 960
ttgcctgtcc aaaataagcg agactatgcc gtagtctggt gtccaacaac atgttcctta 1020
tcagtgataa cgctacaatc ttctttcttt tttctctgtt tctcttgtct ctcccaaccc 1080
atattccgta ttacacctcg tcgtggtcat ttttttgttc agagttttat ttaattctaa 1140
atttcctaac taaaatttca ga 1162

<210> SEQ ID NO 43
<211> LENGTH: 1500
<212> TYPE: DNA
<213> ORGANISM: Caenorhabditis elegans

<400> SEQUENCE: 43
aaaatgccaa acgatccatc ggataatcaa ctgaaaacct acaaggagac gtatccaaaa 60
ccccaagtga tcacaacttc aaatggagct ccgatctact cgaagaccgc cgtgctcacc 120
gccgggcggc gtggcccaat gctcatgcaa gatgtagttt atatggatga gatggctcat 180
ttcgatcgtg aacgtatccc cgagcgtgtc gttcatgcca agggagccgg agcccatgga 240
tacttcgagg tcacccatga catcaccaag tactgtaagg ccgatatgtt caacaaggtc 300
ggaaaacaga caccacttct cgttcgtttt tcaacggtcg ctggagaatc gggatccgct 360
gatactgtcc gcgatccacg tggattctct ctcaaattct ataccgagga gggtaactgg 420
gatctggttg gaaataacac tccgatcttc ttcattcgtg acgcaatcca ctttccgaat 480
ttcattcatg ccctgaagcg caatccacag actcacatga gggatccgaa tgcgctcttc 540
gatttctgga tgaatcgccc tgaatccatt catcaggtga tgttcctcta ctcggatcgt 600
ggaattcctg atggattccg ttttatgaat ggatacggag cgcatacttt caagatggtc 660
aacaaggagg gaaatccgat ttattgtaaa ttccatttca agcctgctca aggttccaag 720
aatctcgatc caactgacgc tggaaagctc gcctcttcgg atccagacta tgcgatccgc 780

-continued

```
gacctgttca atgccattga gtcaagaaat ttcccggaat ggaagatgtt cattcaagtg    840

atgacattcg aacaagctga gaaatgggag ttcaatccat ttgatgtcac taaagtttgg    900

ccacacggtg attacccact gatcgaggtc ggcaagatgg tgctgaacag gaatgtgaag    960

aattatttcg ctgaggtcga acaagccgcc ttctgcccgg cccacatcgt cccaggaatc   1020

gagttctcgc cagacaagat gctccaaggg cgtatcttct cctacacgga cacgcattac   1080

catcgccttg gaccaaacta cattcagctt ccagtcaact gcccgtaccg ctcccgtgct   1140

cataccactc aacgcgatgg tgcaatggct tatgaaagcc agggagatgc gccgaattac   1200

ttcccgaaca gtttccgcgg ataccgtact cgtgatgatg tgaaggagtc gacatttcag   1260

acgactggag atgttgatcg ttatgagact ggagacgatc acaactacga gcagccacgt   1320

cagttctggg agaaagtgct caaggaggag gagagagatc ggctcgttgg gaatttggct   1380

agtgatttgg gtggctgttt ggaggaaatt caaaatggaa tggtcaaaga gttcacgaaa   1440

gttcatccgg atttcggaaa tgctcttcgc catcagctct gccagaagaa gcattaaatt   1500
```

<210> SEQ ID NO 44
<211> LENGTH: 497
<212> TYPE: PRT
<213> ORGANISM: Caenorhabditis elegans

<400> SEQUENCE: 44

```
Met Pro Asn Asp Pro Ser Asp Asn Gln Leu Lys Thr Tyr Lys Glu Thr
1               5                   10                  15

Tyr Pro Lys Pro Gln Val Ile Thr Thr Ser Asn Gly Ala Pro Ile Tyr
            20                  25                  30

Ser Lys Thr Ala Val Leu Thr Ala Gly Arg Arg Gly Pro Met Leu Met
        35                  40                  45

Gln Asp Val Val Tyr Met Asp Glu Met Ala His Phe Asp Arg Glu Arg
    50                  55                  60

Ile Pro Glu Arg Val Val His Ala Lys Gly Ala Gly Ala His Gly Tyr
65                  70                  75                  80

Phe Glu Val Thr His Asp Ile Thr Lys Tyr Cys Lys Ala Asp Met Phe
                85                  90                  95

Asn Lys Val Gly Lys Gln Thr Pro Leu Leu Val Arg Phe Ser Thr Val
            100                 105                 110

Ala Gly Glu Ser Gly Ser Ala Asp Thr Val Arg Asp Pro Arg Gly Phe
        115                 120                 125

Ser Leu Lys Phe Tyr Thr Glu Glu Gly Asn Trp Asp Leu Val Gly Asn
    130                 135                 140

Asn Thr Pro Ile Phe Phe Ile Arg Asp Ala Ile His Phe Pro Asn Phe
145                 150                 155                 160

Ile His Ala Leu Lys Arg Asn Pro Gln Thr His Met Arg Asp Pro Asn
                165                 170                 175

Ala Leu Phe Asp Phe Trp Met Asn Arg Pro Glu Ser Ile His Gln Val
            180                 185                 190

Met Phe Leu Tyr Ser Asp Arg Gly Ile Pro Asp Gly Phe Arg Phe Met
        195                 200                 205

Asn Gly Tyr Gly Ala His Thr Phe Lys Met Val Asn Lys Glu Gly Asn
    210                 215                 220

Pro Ile Tyr Cys Lys Phe His Phe Lys Pro Ala Gln Gly Ser Lys Asn
225                 230                 235                 240

Leu Asp Pro Thr Asp Ala Gly Lys Leu Ala Ser Ser Asp Pro Asp Tyr
                245                 250                 255
```

-continued

```
Ala Ile Arg Asp Leu Phe Asn Ala Ile Glu Ser Arg Asn Phe Pro Glu
            260                 265                 270

Trp Lys Met Phe Ile Gln Val Met Thr Phe Glu Gln Ala Glu Lys Trp
        275                 280                 285

Glu Phe Asn Pro Phe Asp Val Thr Lys Val Trp Pro His Gly Asp Tyr
    290                 295                 300

Pro Leu Ile Glu Val Gly Lys Met Val Leu Asn Arg Asn Val Lys Asn
305                 310                 315                 320

Tyr Phe Ala Glu Val Glu Gln Ala Ala Phe Cys Pro Ala His Ile Val
                325                 330                 335

Pro Gly Ile Glu Phe Ser Pro Asp Lys Met Leu Gln Gly Arg Ile Phe
            340                 345                 350

Ser Tyr Thr Asp Thr His Tyr His Arg Leu Gly Pro Asn Tyr Ile Gln
        355                 360                 365

Leu Pro Val Asn Cys Pro Tyr Arg Ser Arg Ala His Thr Thr Gln Arg
    370                 375                 380

Asp Gly Ala Met Ala Tyr Glu Ser Gln Gly Asp Ala Pro Asn Tyr Phe
385                 390                 395                 400

Pro Asn Ser Phe Arg Gly Tyr Arg Thr Arg Asp Asp Val Lys Glu Ser
                405                 410                 415

Thr Phe Gln Thr Thr Gly Asp Val Asp Arg Tyr Glu Thr Gly Asp Asp
            420                 425                 430

His Asn Tyr Glu Gln Pro Arg Gln Phe Trp Glu Lys Val Leu Lys Glu
        435                 440                 445

Glu Glu Arg Asp Arg Leu Val Gly Asn Leu Ala Ser Asp Leu Gly Gly
    450                 455                 460

Cys Leu Glu Glu Ile Gln Asn Gly Met Val Lys Glu Phe Thr Lys Val
465                 470                 475                 480

His Pro Asp Phe Gly Asn Ala Leu Arg His Gln Leu Cys Gln Lys Lys
                485                 490                 495

His
```

<210> SEQ ID NO 45
<211> LENGTH: 1062
<212> TYPE: DNA
<213> ORGANISM: Caenorhabditis elegans

<400> SEQUENCE: 45

```
tattcgcaga aaaaagtcgt tgcaaacatt cgtttttata tgtttttctt tgagaaagcg     60

tggttcattt ttgaaagtga aaaatatttg cttaaaactt ccaaatttaa atctgcagtg    120

attcagagag gttgagaatt attttcaaaa acattcaatg ttttcccttg gagtgactat    180

gcaaatatga aaatgttttc caaaaatatt tggatgccct gataaaaagt aggtgaaatt    240

tcgcagggga acatcatatt aaaatgttga atttttagaa gaaatggaaa tgtttgtcgg    300

tggtatgctc gaatatttga gatattatat atttactgtt aaatccgaaa tttttgacaa    360

acggaaaaaa tttgtgtcga aatactacat tttcgataac acaaaggtac ttccataaca    420

cttataaaaa ctgtttgact atcttatttc aggaaaaaaa aatccaagaa taaacatttt    480

tcagaatttg aactttctaa tggctgatta ataaaacaaa gttatacaac tattcaaagc    540

agttgctcaa tctggcattt tcttgtgttt ttttttgaat atttcatcag caagatgttg    600

ataattttgt gttaattcta attgttttct acaatttttc aaaccgaaaa ttgacctttg    660

actttgttta ctttgttctc gtgggttaac tgttcactga tttctattgc tgttgatgag    720
```

-continued

```
gtctttgatc aaatttgtat tgtttttata ctgcatattg cttcaattct aaatcatcta    780

atatattgtc aaacaacttc ttgttttttt tttcattcaa aacttctgca aaaacgttct    840

cttaacaaag gttcacacaa caactctcct ctccatctct ttctctcaac aacaatgtgc    900

tggccttgca tgtttgccag tgcgggttgt ttacgcgttt tcaagatttt tggtctccta    960

tctaacgtcc cgaaatgcat tttttccttt catttggttt ttttctgttc gagaaaagtg   1020

accgtttgtc aaatcttcta attttcagtg aataaaatgc tg                      1062
```

<210> SEQ ID NO 46
<211> LENGTH: 815
<212> TYPE: DNA
<213> ORGANISM: Caenorhabditis elegans

<400> SEQUENCE: 46

```
cgtttgtcaa atcttctaat tttcagtgaa taaaatgctg caatctactg ctcgcactgc     60

ttcaaagctt gttcaaccgg ttgcgggagt tctcgccgtc cgctccaagc acactctccc    120

agatctccca ttcgactatg cagatttgga acctgtaatc agccatgaaa tcatgcagct    180

tcatcatcaa aagcatcatg ccacctacgt gaacaatctc aatcagatcg aggagaaact    240

tcacgaggct gtttcgaaag ggaatctaaa agaagcaatt gctctccaac cagcgctgaa    300

attcaatggt ggtggacaca tcaatcattc tatcttctgg accaacttgg ctaaggatgg    360

tggagaacct tcaaaggagc tgatggacac tattaagcgc gacttcggtt ccctggataa    420

cttgcaaaaa cgtctttctg acatcactat tgcggttcaa ggctctggct ggggatggtt    480

gggatattgc aagaaagaca aaatcttgaa gatcgccacc tgtgcaaacc aggatccttt    540

ggaaggaatg gtcccacttt ttggaattga cgtttgggag cacgcctact acttgcagta    600

caaaaatgtc cgcccagact atgtccatgc tatttggaag attgccaact ggaagaatat    660

cagcgagaga tttgccaatg ctcgacaata aaagcaggaa atattggaat tttcggtttt    720

acgaaaatat tgaagataat tcagatgtag tttaaaacgc tgagaatttg tatttttgta    780

attgtttaaa taaaagaacg cacagttttt tctta                               815
```

<210> SEQ ID NO 47
<211> LENGTH: 218
<212> TYPE: PRT
<213> ORGANISM: Caenorhabditis elegans

<400> SEQUENCE: 47

```
Met Leu Gln Ser Thr Ala Arg Thr Ala Ser Lys Leu Val Gln Pro Val
1               5                   10                  15

Ala Gly Val Leu Ala Val Arg Ser Lys His Thr Leu Pro Asp Leu Pro
            20                  25                  30

Phe Asp Tyr Ala Asp Leu Glu Pro Val Ile Ser His Glu Ile Met Gln
        35                  40                  45

Leu His His Gln Lys His His Ala Thr Tyr Val Asn Asn Leu Asn Gln
    50                  55                  60

Ile Glu Glu Lys Leu His Glu Ala Val Ser Lys Gly Asn Leu Lys Glu
65                  70                  75                  80

Ala Ile Ala Leu Gln Pro Ala Leu Lys Phe Asn Gly Gly Gly His Ile
                85                  90                  95

Asn His Ser Ile Phe Trp Thr Asn Leu Ala Lys Asp Gly Gly Glu Pro
            100                 105                 110

Ser Lys Glu Leu Met Asp Thr Ile Lys Arg Asp Phe Gly Ser Leu Asp
```

-continued

```
        115                 120                 125

Asn Leu Gln Lys Arg Leu Ser Asp Ile Thr Ile Ala Val Gln Gly Ser
    130                 135                 140

Gly Trp Gly Trp Leu Gly Tyr Cys Lys Lys Asp Lys Ile Leu Lys Ile
145                 150                 155                 160

Ala Thr Cys Ala Asn Gln Asp Pro Leu Glu Gly Met Val Pro Leu Phe
                165                 170                 175

Gly Ile Asp Val Trp Glu His Ala Tyr Tyr Leu Gln Tyr Lys Asn Val
            180                 185                 190

Arg Pro Asp Tyr Val His Ala Ile Trp Lys Ile Ala Asn Trp Lys Asn
        195                 200                 205

Ile Ser Glu Arg Phe Ala Asn Ala Arg Gln
    210                 215


<210> SEQ ID NO 48
<211> LENGTH: 851
<212> TYPE: DNA
<213> ORGANISM: Caenorhabditis elegans

<400> SEQUENCE: 48

ttatcaacca ctaggttccg tcttaatcgt ccaaatattg atccgctcgc tcgtgttttc     60

tcaacttctt tatttgctgt gtttttctgt ttctatagtt ctccattttc catctcctct    120

tcgcttgttg aatggacttt attttgataa gttcatttta atttttctaa caatctcatc    180

actagctcat gatgacaatt gcaaagaaat tcgtcatata gaggggaaaa atgctgacaa    240

atattgaaaa gccttcagga gagatgtaga gacgtaggag tagagacaga acataaattt    300

gagaagcttg tagggagaat agacatagag ttaccatggg aaaaacgctc gcattttcca    360

tttaacgaga ttttctagat cacaacattt tgtgatccgt tgtgcgaaaa tcaagctttt    420

tatcaaactt ttatcgtctg ttcattcttt ctgacaatct ttattatctt attaaacttg    480

actaattgta ttgaaagtat ttttttagat gcgaacgaag ttccattttt catgacttaa    540

catctcttaa cgttagtgaa atttttgaat tccaattagg actacggtag gagttctgta    600

gttgatttcc tgaacacttg ttttgtaacc tttctgaacg gattttaata tttctaaaat    660

tttaaattgc aaatctgagt cctattaaaa gatgtttcat ccgtaaaacc aacaaacaaa    720

atatcacttt atcatcatga gatttaatgt ttccttttga ttttctgaat tgttgtactt    780

tccttcaaac gacttattga actgatgtaa ctttccttct aatgttatca tttgtatttt    840

tttgcagaat g                                                         851


<210> SEQ ID NO 49
<211> LENGTH: 2297
<212> TYPE: DNA
<213> ORGANISM: Caenorhabditis elegans

<400> SEQUENCE: 49

tttgcagaat gggtcttttg acgaaaggta gtccgttgac gtgggcagaa accgtaccgc     60

acattgatta tatcaagaag cacggaattg ctcaattcat caatctctac catcgtctga    120

aatcaagaca cggagatcaa ttgaaatggg gagatgagat tgaatacact attgtaaaat    180

ttgatgacgc aaacaagaaa gttcgcgtgt cgtgcaaagc tgaagagctt cttaataagt    240

tacaagccga agagcaggtg aatgcgatgc ttggaactgc caatcgattc ctttggagac    300

cagaattcgg atcctacatg atcgagggaa cccccggaat gccttacgga ggtctcatcg    360

cttgcttcaa cattgtcgag gcaaacatga aattgcgcag acaggtcgtc aaaaagttat    420
```

-continued

```
taaagaagga tgaaacatgt ctatcgatat cgttcccatc tcttggagta cctggattca    480

cattcccgga agtagcagct gatagaaaga atgatgatgc agctaatagc gttttctggc    540

cagaacaagc tgtattcttg ggccatccac gtttcaagaa tcttaccaaa aatattaaag    600

gtcgcagagg aagtaaagta gctatcaacg tcccgatatt caaggatacg aacacccccca    660

gtccattcgt tgaagattta tctgcacttg gaggtcctga tgatactcgt gatgcgaaac    720

ctgatcacat ttatatggat catatgggat tcggaatggg gtgctgttgt cttcaagtca    780

ctttccaggc tgtgaacgtc gatgaagcca gatggttgta cgatcagctg acaccgatta    840

caccgattct actggcactc tctgccgcca caccaatctt ccgtggaaaa ttatccaatg    900

tcgattctag atgggatatc attagtgcaa gtgtcgacga tcgtacaccg gaggaaagag    960

gattggaacc tctcaagaat tcgaaatggg ttattgataa gagtcgctac gactccacgg   1020

actgttacat ttatccatgt tctgttggct acaatgatat tcctcttcaa tacgacgaaa   1080

ccatatataa acaactaatt gatggaaata ttgatgagcc actggcaaaa catattgcgc   1140

atatgttcat tcgtgatcca catcaagttt tccgtgagcg tatcgaacag gacgatgaga   1200

aaagcagtga acactttgaa acaattcaat catcgaattg gatgaacatg cgattcaagc   1260

caccaccacc agatgctcca gaaatcggat ggagagtcga attccggcca actgaagttc   1320

aactgaccga ctttgaaaat gcagcatact gttgcttcgt tgtattgctc accagaatga   1380

tgatctcctt caggctgaca tatttgatgc caatttcaat ggttactgaa aatatgaagc   1440

gtgctcagca aaaagatgca gttctcaatc agaaattcct gttcagaaaa ggattggctg   1500

agtgcaaatc tgctcccgaa aatttgaaag gatcggagaa atgtggacca cctagtcaag   1560

atattgaaga aatgtcgatt gatgagatta tcaatggaaa gaaaaatgga ttcccaggtc   1620

tcatttcact tattcgccaa tttctagatt ctgctgatgt tgatgtggat actcggtgta   1680

cgatttctca atatttgaac tttatttcga aacgagcaac tggagagatt aatactttgg   1740

ctcactggac acgtggattc gtacaatctc atcctgcata caaacatgac agtgatgtaa   1800

atgataatat agtttacgat cttttgaaaa agatggatgc catctcaaac ggagaagatc   1860

actgtgagaa gctgctcgga tgctaccgct ctaaaaccga tcatgccatt tctgctgctg   1920

ttcgcaaagc tgaagagcac atgatcgtgt ccagccaaaa acgtgcacat taggcgataa   1980

ttgattgatt atgtgatttt aatttattta tgttctatac gtcgtgtttc ccattccttc   2040

taggccttcc atgattcaca atttttcgat gccatatcaa tttagttggc catctacatt   2100

aaattactga tatgttgatg ctattttcta gtaagcagat gtcagtgttt agtaattcaa   2160

aaatttaaac tctgaatttc taaatgcttg tttttttgagt agtaggaatc agtacgaatg   2220

gtacattaat ctgaaaataa tttcatattt atgtacaatg ctcccctgaa tccatcatat   2280

aattattatc cgtgttg                                                  2297
```

<210> SEQ ID NO 50
<211> LENGTH: 654
<212> TYPE: PRT
<213> ORGANISM: Caenorhabditis elegans

<400> SEQUENCE: 50

```
Met Gly Leu Leu Thr Lys Gly Ser Pro Leu Thr Trp Ala Glu Thr Val
1               5                   10                  15

Pro His Ile Asp Tyr Ile Lys Lys His Gly Ile Ala Gln Phe Ile Asn
            20                  25                  30
```

-continued

```
Leu Tyr His Arg Leu Lys Ser Arg His Gly Asp Gln Leu Lys Trp Gly
        35                  40                  45

Asp Glu Ile Glu Tyr Thr Ile Val Lys Phe Asp Asp Ala Asn Lys Lys
    50                  55                  60

Val Arg Val Ser Cys Lys Ala Glu Glu Leu Leu Asn Lys Leu Gln Ala
65                  70                  75                  80

Glu Glu Gln Val Asn Ala Met Leu Gly Thr Ala Asn Arg Phe Leu Trp
                85                  90                  95

Arg Pro Glu Phe Gly Ser Tyr Met Ile Glu Gly Thr Pro Gly Met Pro
            100                 105                 110

Tyr Gly Gly Leu Ile Ala Cys Phe Asn Ile Val Glu Ala Asn Met Lys
        115                 120                 125

Leu Arg Arg Gln Val Val Lys Lys Leu Leu Lys Lys Asp Glu Thr Cys
    130                 135                 140

Leu Ser Ile Ser Phe Pro Ser Leu Gly Val Pro Gly Phe Thr Phe Pro
145                 150                 155                 160

Glu Val Ala Ala Asp Arg Lys Asn Asp Asp Ala Ala Asn Ser Val Phe
                165                 170                 175

Trp Pro Glu Gln Ala Val Phe Leu Gly His Pro Arg Phe Lys Asn Leu
            180                 185                 190

Thr Lys Asn Ile Lys Gly Arg Arg Gly Ser Lys Val Ala Ile Asn Val
        195                 200                 205

Pro Ile Phe Lys Asp Thr Asn Thr Pro Ser Pro Phe Val Glu Asp Leu
    210                 215                 220

Ser Ala Leu Gly Gly Pro Asp Asp Thr Arg Asp Ala Lys Pro Asp His
225                 230                 235                 240

Ile Tyr Met Asp His Met Gly Phe Gly Met Gly Cys Cys Cys Leu Gln
                245                 250                 255

Val Thr Phe Gln Ala Val Asn Val Asp Glu Ala Arg Trp Leu Tyr Asp
            260                 265                 270

Gln Leu Thr Pro Ile Thr Pro Ile Leu Leu Ala Leu Ser Ala Ala Thr
        275                 280                 285

Pro Ile Phe Arg Gly Lys Leu Ser Asn Val Asp Ser Arg Trp Asp Ile
    290                 295                 300

Ile Ser Ala Ser Val Asp Asp Arg Thr Pro Glu Glu Arg Gly Leu Glu
305                 310                 315                 320

Pro Leu Lys Asn Ser Lys Trp Val Ile Asp Lys Ser Arg Tyr Asp Ser
                325                 330                 335

Thr Asp Cys Tyr Ile Tyr Pro Cys Ser Val Gly Tyr Asn Asp Ile Pro
            340                 345                 350

Leu Gln Tyr Asp Glu Thr Ile Tyr Lys Gln Leu Ile Asp Gly Asn Ile
        355                 360                 365

Asp Glu Pro Leu Ala Lys His Ile Ala His Met Phe Ile Arg Asp Pro
    370                 375                 380

His Gln Val Phe Arg Glu Arg Ile Glu Gln Asp Asp Glu Lys Ser Ser
385                 390                 395                 400

Glu His Phe Glu Thr Ile Gln Ser Ser Asn Trp Met Asn Met Arg Phe
                405                 410                 415

Lys Pro Pro Pro Pro Asp Ala Pro Glu Ile Gly Trp Arg Val Glu Phe
            420                 425                 430

Arg Pro Thr Glu Val Gln Leu Thr Asp Phe Glu Asn Ala Ala Tyr Cys
        435                 440                 445

Cys Phe Val Val Leu Leu Thr Arg Met Met Ile Ser Phe Arg Leu Thr
```

-continued

```
    450                 455                 460

Tyr Leu Met Pro Ile Ser Met Val Thr Glu Asn Met Lys Arg Ala Gln
465                 470                 475                 480

Gln Lys Asp Ala Val Leu Asn Gln Lys Phe Leu Phe Arg Lys Gly Leu
                485                 490                 495

Ala Glu Cys Lys Ser Ala Pro Glu Asn Leu Lys Gly Ser Glu Lys Cys
            500                 505                 510

Gly Pro Pro Ser Gln Asp Ile Glu Glu Met Ser Ile Asp Glu Ile Ile
        515                 520                 525

Asn Gly Lys Lys Asn Gly Phe Pro Gly Leu Ile Ser Leu Ile Arg Gln
    530                 535                 540

Phe Leu Asp Ser Ala Asp Val Asp Val Asp Thr Arg Cys Thr Ile Ser
545                 550                 555                 560

Gln Tyr Leu Asn Phe Ile Ser Lys Arg Ala Thr Gly Glu Ile Asn Thr
                565                 570                 575

Leu Ala His Trp Thr Arg Gly Phe Val Gln Ser His Pro Ala Tyr Lys
            580                 585                 590

His Asp Ser Asp Val Asn Asp Asn Ile Val Tyr Asp Leu Leu Lys Lys
        595                 600                 605

Met Asp Ala Ile Ser Asn Gly Glu Asp His Cys Glu Lys Leu Leu Gly
    610                 615                 620

Cys Tyr Arg Ser Lys Thr Asp His Ala Ile Ser Ala Ala Val Arg Lys
625                 630                 635                 640

Ala Glu Glu His Met Ile Val Ser Ser Gln Lys Arg Ala His
                645                 650


<210> SEQ ID NO 51
<211> LENGTH: 15
<212> TYPE: PRT
<213> ORGANISM: Caenorhabditis elegans

<400> SEQUENCE: 51

Thr Thr Asp Ser Ser Ser Thr Cys Ser Arg Leu Ser Ser Glu Ser
1               5                   10                  15


<210> SEQ ID NO 52
<211> LENGTH: 15
<212> TYPE: PRT
<213> ORGANISM: Homo sapiens
<220> FEATURE:
<221> NAME/KEY: PHOSPHORYLATION
<222> LOCATION: 1, 5, 9, 13
<223> OTHER INFORMATION: Can be phosporylated

<400> SEQUENCE: 52

Ser Gly Ile His Ser Gly Ala Thr Thr Thr Ala Pro Ser Leu Ser
1               5                   10                  15


<210> SEQ ID NO 53
<211> LENGTH: 23
<212> TYPE: PRT
<213> ORGANISM: Caenorhabditis elegans
<220> FEATURE:
<221> NAME/KEY: PHOSPHORYLATION
<222> LOCATION: 15
<223> OTHER INFORMATION: Can be phosporylated

<400> SEQUENCE: 53

Asp Cys Thr Thr Asp Ser Ser Ser Thr Cys Ser Arg Leu Ser Ser Glu
1               5                   10                  15
```

-continued

```
Ser Pro Arg Tyr Thr Ser Glu
            20


<210> SEQ ID NO 54
<211> LENGTH: 23
<212> TYPE: PRT
<213> ORGANISM: Caenorhabditis elegans
<220> FEATURE:
<221> NAME/KEY: PHOSPHORYLATION
<222> LOCATION: 15
<223> OTHER INFORMATION: Can be phosporylated

<400> SEQUENCE: 54

Asp Cys Thr Thr Asp Ser Ser Ser Thr Cys Ala Arg Leu Ser Ser Glu
1               5                   10                  15

Ser Pro Arg Tyr Thr Ser Glu
            20


<210> SEQ ID NO 55
<211> LENGTH: 42
<212> TYPE: DNA
<213> ORGANISM: Caenorhabditis elegans

<400> SEQUENCE: 55

actttatca tcatgagatt taatgtttcc ttttgatttt ct                      42


<210> SEQ ID NO 56
<211> LENGTH: 45
<212> TYPE: DNA
<213> ORGANISM: Caenorhabditis elegans

<400> SEQUENCE: 56

cacctctgtc atcatgatga tttttggagc attatcatca tttct                  45


<210> SEQ ID NO 57
<211> LENGTH: 45
<212> TYPE: DNA
<213> ORGANISM: Caenorhabditis elegans

<400> SEQUENCE: 57

cacctctgtc atcatgatga tttttagagc attatcatca tttct                  45
```